US010047149B2

(12) United States Patent
Schneewind et al.

(10) Patent No.: US 10,047,149 B2
(45) Date of Patent: Aug. 14, 2018

(54) COMPOSITIONS AND METHODS RELATED TO ANTIBODIES TO STAPHYLOCOCCAL PROTEIN A

(71) Applicant: The University of Chicago, Chicago, IL (US)

(72) Inventors: Olaf Schneewind, Chicago, IL (US); Dominique M. Missiakas, Chicago, IL (US); Hwan Keun Kim, Naperville, IL (US); Carla Emolo, Chicago, IL (US); Andrea DeDent, Chicago, IL (US)

(73) Assignee: The University of Chicago, Chicago, IL (US)

( * ) Notice: Subject to any disclaimer, the term of this patent is extended or adjusted under 35 U.S.C. 154(b) by 25 days.

(21) Appl. No.: 15/377,050

(22) Filed: Dec. 13, 2016

(65) Prior Publication Data

US 2017/0218055 A1 Aug. 3, 2017

Related U.S. Application Data

(62) Division of application No. 14/238,811, filed as application No. PCT/US2012/050991 on Aug. 15, 2012, now Pat. No. 9,556,281.

(60) Provisional application No. 61/523,751, filed on Aug. 15, 2011, provisional application No. 61/615,083, filed on Mar. 23, 2012, provisional application No. 61/618,417, filed on Mar. 30, 2012, provisional application No. 61/674,135, filed on Jul. 20, 2012.

(51) Int. Cl.
| A61K 39/00 | (2006.01) |
| A61K 39/395 | (2006.01) |
| A61K 39/40 | (2006.01) |
| C07K 16/12 | (2006.01) |
| A61K 45/06 | (2006.01) |
| G01N 33/68 | (2006.01) |

(52) U.S. Cl.
CPC .......... *C07K 16/1271* (2013.01); *A61K 39/40* (2013.01); *A61K 45/06* (2013.01); *G01N 33/6854* (2013.01); *A61K 2039/505* (2013.01); *A61K 2039/545* (2013.01); *C07K 2317/14* (2013.01); *C07K 2317/21* (2013.01); *C07K 2317/51* (2013.01); *C07K 2317/515* (2013.01); *C07K 2317/56* (2013.01); *C07K 2317/565* (2013.01); *C07K 2317/569* (2013.01); *C07K 2317/76* (2013.01); *C07K 2317/92* (2013.01); *G01N 2333/31* (2013.01); *G01N 2500/04* (2013.01)

(58) Field of Classification Search
CPC .............. A61K 2039/505; A61K 38/00; C07K 2317/24
See application file for complete search history.

(56) References Cited

U.S. PATENT DOCUMENTS

| 5,648,240 A | 7/1997 | Hook et al. ................. 435/69.3 |
| 5,801,234 A | 9/1998 | Hodgson et al. ........... 536/23.7 |
| 5,840,846 A | 11/1998 | Hook et al. ................. 530/350 |
| 6,008,341 A | 12/1999 | Foster et al. ............... 536/23.7 |
| 6,288,214 B1 | 9/2001 | Hook et al. ................ 530/387.1 |
| 6,627,730 B1 | 9/2003 | Burnie ........................ 530/326 |
| 7,488,807 B2 | 2/2009 | Mach et al. ............... 530/388.4 |
| 2002/0169288 A1 | 11/2002 | Hook et al. ................. 530/350 |
| 2006/0205016 A1 | 9/2006 | Silverman .................... 435/7.1 |
| 2006/0246083 A1 | 11/2006 | Dale .......................... 424/184.1 |
| 2006/0263792 A1 | 11/2006 | Mohamed et al. ............ 435/6 |
| 2007/0166281 A1 | 7/2007 | Kosak ........................ 424/85.1 |
| 2008/0118937 A1 | 5/2008 | Mach ......................... 435/7.33 |
| 2009/0162902 A1 | 6/2009 | Mach et al. ................. 435/69.6 |
| 2009/0252729 A1 | 10/2009 | Farrington et al. ........ 424/135.1 |
| 2010/0047252 A1 | 2/2010 | Mach ......................... 424/150.1 |
| 2010/0063256 A1 | 3/2010 | Spector ..................... 530/387.1 |
| 2010/0233173 A1 | 9/2010 | Wu et al. .................. 424/136.1 |
| 2011/0002932 A1 | 1/2011 | Pier et al. .................. 424/137.1 |
| 2011/0117099 A1 | 5/2011 | Arrecubieta et al. ...... 424/139.1 |
| 2011/0177523 A1 | 7/2011 | Bommarito et al. .......... 435/7.1 |

FOREIGN PATENT DOCUMENTS

| WO | WO 98/57994 | 12/1998 |
| WO | WO 00/02523 | 1/2000 |
| WO | WO 00/12132 | 3/2000 |
| WO | WO 00/12689 | 3/2000 |
| WO | WO 00/15238 | 3/2000 |
| WO | WO 01/60852 | 8/2001 |
| WO | WO 2006/032472 | 3/2006 |
| WO | WO 2006/032475 | 3/2006 |
| WO | WO 2006/032500 | 3/2006 |
| WO | WO 2007/113222 | 10/2007 |
| WO | WO 2007/113223 | 10/2007 |

(Continued)

OTHER PUBLICATIONS

Atkins et al., "*S. aureus* IgG-binding proteins SpA and Sbi: host specificity and mechanisms of immune complex formation", *Mol. Immunol*, 45(6):1600-1611, 2008.
Baba et al., "Genome and virulence determinants of high virulence community-acquired MRSA", *Lancet*, 359(9320):1819-1827, 2002.
Bendig M. M. *Methods: A Companion to Methods in Enzymology*, 1995; 8: 83-93.
Berberian et al, "A VH clonal deficit in human immunodeficiency virus-positive individuals reflects a B-cell maturational arrest", *Blood*, 78(1):175-179, 1991.
Berberian et al., "Immunoglobulin VH3 gene products: natural ligands for HIV gp120", *Science*, 261(5128):1588-1591, 1993.

(Continued)

*Primary Examiner* — Gary B Nickol
*Assistant Examiner* — Lakia J Jackson-Tongue
(74) *Attorney, Agent, or Firm* — Norton Rose Fulbright US LLP

(57) ABSTRACT

Embodiments concern methods and compositions for treating or preventing a bacterial infection, particularly infection by a *Staphylococcus* bacterium. Aspects include methods and compositions for providing a passive immune response against the bacteria. In certain embodiments, the methods and compositions involve an antibody that binds Staphylococcal protein A (SpA).

16 Claims, 12 Drawing Sheets

(56) References Cited

FOREIGN PATENT DOCUMENTS

| WO | WO 2008/140487 | 11/2008 |
|---|---|---|
| WO | WO 2010/042481 | 4/2010 |
| WO | WO 2011/005341 | 1/2011 |
| WO | WO 2012/003474 | 1/2012 |

OTHER PUBLICATIONS

Boucher and Corey, "Epidemiology of methicillin-resistant *Staphylococcus aureus*", *Clin Infect Dis.*, 46(Suppl 5):S344-S349, 2008.
Burman et al., "Interaction of human complement with Sbi, a staphylococcal immunoglobulin-binding protein: indications of a novel mechanism of complement evasion by *Staphylococcus aureus*", *J. Biol. Chem*, 283(25):17579-17593, 2008.
Cary et al., "The murine clan V(H) III related 7183, J606 and S107 and DNA4 families commonly encode for binding to a bacterial B cell superantigen", *Mol Immunol.*, 36(11-12):769-776, 1999.
Casset et al., *Biochemical and Biophysical Research Communications*, 2003; 307: 198-205.
Cheng et al., "Genetic requirements for *Staphylococcus aureus* abscess formation and persistence in host tissues", *FASEB J* 23(10):3393-3404, 2009.
Claro et al., "*Staphylococcus aureus* Protein A Binds to Osteoblasts and Triggers Signals That Weaken Bone in Osteomyelitis", *PLoS One*, 6(4):e18748, 2011.
Colman P. M. *Research in Immunology*, 1994; 145: 35-36.
DeDent et al., "Exploring *Staphylococcus aureus* pathways to disease for vaccine development", *Semin Immunopathol*, 34(2):317-333, 2012.
Diep et al., "Complete genome sequence of USA300, an epidemic clone of community-acquired meticillin-resistant *Staphylococcus aureus*", *Lancet*, 367(9512):731-739, 2006.
Fischetti, "Streptococcal M protein: molecular design and biological behavior", *Clin Microbiol Rev*, 2(3):285-314, 1989.
Forsgren et al., "Lymphocyte stimulation by protein A of *Staphylococcus aureus*", *Eur. J. Immunol.*, 6(3):207-213, 1976.
Goodyear and Silverman, "Death by a B cell superantigen: In vivo VH-targeted apoptotic supraclonal B cell deletion by a Staphylococcal Toxin", *J Exp Med*, 197(9):1125-1139, 2003.
Goodyear and Silverman, "Staphylococcal toxin induced preferential and prolonged in vivo deletion of innate-like B lymphocytes", *Proc Natl Acad Sci USA*, 101(31):11392-11397, 2004.
Graille et al., "Crystal structure of *Staphylococcus aureus* protein A domain complexed with the Fab fragment of a human IgM antibody: structural basis for recognition of B-cell receptors and superantigen activity", *Proc Natl Acad Sci USA*, 97(10):5399-5404, 2000.
Haupt et al., "The *Staphylococcus aureus* protein Sbi acts as a complement inhibitor and forms a tripartite complex with host complement Factor H and C3b", *PLoS Pathog*, 4(12):e1000250, 2008.
Hollingshead et al., "A highly conserved region present in transcripts encoding heterologous M proteins of group A streptococci", *Infect Immun*, 55(12):3237-3239, 1987.
Huang et al., "Immunoglobulin heavy chain gene expression in peripheral blood B lymphocytes", *J Clin Invest*, 89(4):1331-1343, 1992.
International Search Report and Written Opinion issued in PCT/US2012/050991, dated Feb. 25, 2013.
Jones and Fischetti, "The importance of the location of antibody binding on the M6 protein for opsonization and phagocytosis of group A M6 streptococci", *J Exp Med*, 167(3):1114-1123, 1988.
Jones et al., "Immunochemical localization and amino acide sequences of crossreactive epitopes within the group A streptococcal M6 protein", *J Exp. Med.*, 164(4):1226-1238, 1986.
Kennedy et al., "Epidemic recent clonal expansion community-associated methicillin-resistant *Staphylococcus aureus*: recent clonal expansion and diversification", *Proc Natl Acad Sci USA*, 105(4):1327-1332, 2008.

Kim et al., "Identifying protective antigens of *Staphylococcus aureus*, a pathogen that suppresses host immune responses", *FASEB J*, 25(10):3605-3612, 2011.
Kim et al., "IsdA and IsdB antibodies protect mice against *Staphylococcus aureus* abscess formation and lethal challenge", *Vaccine*, 28(38):6382-6392, 2010b.
Kim et al., "Nontoxigenic protein A vaccine for methicillin-resistant *Staphylococcus aureus* infections in mice", *J Exp Med*, 207(9):1863-1870, 2010a.
Kim et al., "Protein A-specific monoclonal antibodies and prevention of *Staphylococcus aureus* disease in mice", *Infect Immun*, 80(10)3460-3470, 2012a.
Kim et al., "Recurrent infections and immune evasion strategies of *Staphylococcus aureus*", *Curr Opin Microbiol*, 15(1):92-99, 2012b.
Klevens et al., "Invasive methicillin-resistant *Staphylococcus aureus* infections in the United States", *JAMA*, 298(15):1763-1771, 2007.
Kronvall et al., "Protein A reactivity with mouse immunoglobulins. Structural relationship between some mouse a reactivity and human immunoglobulins", *J Immunol*, 105(5):116-1123, 1970.
Lancefield, "Current knowledge of type-specific M antigens of group A streptococcia", *J Immunol*, 89:307-313, 1962.
Lee, "The prospects for developing a vaccine against *Staphylococcus aureus*", *Trends Microbiol.*, 4(4):162-166, 1996.
MacCallum et al., *J. Mol. Biol.* 1996; 262: 732-745.
Mazmanian et al., "*Staphylococcus aureus* sortase, an enzyme that anchors surface proteins to the cell wall", *Science*, 285(5428):760-763, 1999.
McCarthy and Lindsay, "Genetic variation in *Staphylococcus aureus* surface and immune evasion genes is lineage associated: implications for vaccine design and host-pathogen interactions", *BMC Microbiol.*, 10:173, 2010.
Mohamed et al., "Heteropolymers: A New Class of Therapeutics for Treating Lethal Bacterial and Viral Infections", Nov. 17, 2004 DTIC Online Accession No. ADA449597.
Moks et al., "Staphylococcal protein A consists of five IgG-binding domains", *Eur. J. Biochem*, 156(3):637-643, 1986.
Paul, William E. *Fundamental Immunology*, 3$^{rd}$ ed. Raven Press, New York: 1993, 292-295.
Perry et al., "Anchoring of surface proteins to the cell wall of *Staphylococcus aureus*. III. Lipid II is an in vivo peptidoglycan substrate for sortase-catalyzed surface protein anchoring", *J. Biol Chem*, 277(18):1241-16248, 2002.
Phillips et al., "Streptococcal M protein: alpha-helical coiled-coil structure and arrangement on cell surface", *Proc Natl Acad Sci USA*, 78(8):4689-4693, 1981.
Robbins and Schneerson, "Haemophilus influenzae type b: the search for a vaccine", *Pediatr Infect Dis J.*, 6(8):791-794, 1987.
Robbins and Schneerson, "Polysaccharide-protein conjugates: a new generation of vaccines", *J. Infect. Dis.*, 161(5):821-832, 1990.
Robbins et al., "Hypothesis: how licensed vaccines confer protective immunity", *Adv Exp Med Biol*, 397:169-182, 1996.
Rudikoff et al., *Proc. Natl. Acad. Sci. USA*, 1982; 79(6): 1979-1983.
Sasso et al., "Human IgM molecules that bind staphylococcal protein A contain VHIII H chains", *J Immunol.*, 142(8):2778-2783, 1989.
Scott et al., "Conversion containing an M6 of an M- group a streptococcus to M+ by transfer of a plasmid gene", *J Exp Med.*, 164(5):1641-1651, 1986.
Silverman and Goodyear, "Confounding B-cell defences: lessons from a staphylococcal superantigen", *Nat Rev Immunol*, 6(6):465-475, 2006.
Sjodahl, "Repetitive sequences in protein A from *Staphylococcus aureus*. Arrangement of five regions within the protein, four being highly homologous and Fc-binding",*Eur J Biochem*, 73(2):343-351, 1977.
Sjoquist et al., "Protein A isolated from *Staphylococcus aureus* after digestion with lysostaphin", Eur. J. Biochem, 29(3):572-578, 1972.
Smith et al., "The immune evasion protein Sbi of *Staphylococcus aureus* occurs both extracellularly and anchored to the cell envelope by binding lipoteichoic acid", *Mol Microbiol*, 83(4):789-804, 2012.
Spellberg and Daum, "Development of a vaccine against *Staphylococcus aureus*", *Semin Immunopathol*, 34(2):335-348, 2012.

(56) References Cited

OTHER PUBLICATIONS

Stahlenheim et al., "Protein A From *Staphylococcus aureus*", *J. Immunol.*, 103:467-473, 1970.
Staph Infections Overview, Mayo Clinic, http://www.mayoclinic.org/diseases-conditions/staph-infections/basics/definition/con-20031418; pp. 1-8 accessed Jun. 24, 2015.
Staph Infections Prevention, Mayo Clinic, http://www.mayoclinic.org/diseases-conditions/staph-infections/basics/prevention/con-20031418; 1 page accessed Jun. 25, 2015.
Stranger-Jones et al., "Vaccine assembly from surface proteins of *Staphylococcus aureus*", *Proc natl Acad Sci USA*, 103(45):16942-16947, 2006.
Zhang et al., "A second IgG-binding protein in *Staphylococcus aureus*", *Microbiology*, 144(pt 4):985-991, 1998.
Zhang et al., "*Staphylococcus aureus* expresses a cell surface protein that binds both IgG and beta2-glycoprotein I", *Microbiology*, 145(pt 1):177-183, 1999.

Heavy Chain

| | CDR1 | SEQ ID NO: | CDR2 | SEQ ID NO: | CDR3 | SEQ ID NO: |
|---|---|---|---|---|---|---|
| 1B10 | GFTFSNYD | 116 | ISSGGTYP | 117 | ARGGFLITTRDYYAMDY | 118 |
| 2C3 | GFTFSNYD | 131 | ISSGGTYP | 132 | ARGGFLITTRDYYAMDY | 133 |
| 5A10 | GFAFSNYD | 11 | ISSGGTYP | 12 | ARGGFLITTRDYYAMDY | 13 |
| 8E2 | GYTFTEYS | 21 | FYPGSGYIA | 159 | RHGYG-NYV--GYAMDY | 23 |
| 3A6 | GYNFTDYS | 31 | INTETAES | 32 | AHFDC------------ | 33 |
| 7E2 | GYTFTDYS | 41 | INTATGEP | 42 | APQLTG--PFAY----- | 43 |
| 3F6 | GFTFNTNA | 51 | IRSKSNNYAT | 52 | VTEHYD-YDYYVMDY-- | 53 |
| 1F10 | GNAFTNYL | 61 | INPGSGIT | 62 | SGSA----N--WFAY-- | 63 |
| 6D11 | GNAFTNYL | 71 | INPGSGIT | 72 | SGSA----N--WFAY-- | 73 |
| 3D11 | GYSFTSYY | 81 | IDPFNGGT | 82 | ARYGYD--GT-FYAMDY | 83 |
| 5A11 | GFTFSDYY | 91 | ISDGGTYT | 92 | ARDRDYDEGPYFDY--- | 93 |
| 2F2 | RFTFSSYV | 96 | IGSGGTTY | 97 | RGRGYGF--AWYFDV-- | 98 |
| 8D4 | GSTFTNHH | 111 | LNPYNDYT | 112 | ATTFD---S-------- | 113 |
| 5A10 | GFAFSNYD | 11 | ISSGGTYP | 12 | ARGGFLITTRDYYAMDY | 13 |
| 3F6 | GFTFNTNA | 51 | IRSKSNNYAT | 52 | VTEHYD-YDYYVMDY-- | 53 |
| 3D11 | GYSFTSYY | 81 | IDPFNGGT | 82 | ARYGYD--GT-FYAMDY | 83 |

FIG. 8A

Light Chain

| | CDR1 | SEQ ID NO: | CDR2 | CDR3 | SEQ ID NO: |
|---|---|---|---|---|---|
| 5A10 | -------SSVSY | 16 | DTS | QQWSSYPPT | 18 |
| 8E2 | -------EIIYSY | 26 | FAK | QHHYGTPYT | 28 |
| 3A6 | QSLVHSNGNTY | 36 | KVS | SQITYVPWT | 38 |
| 7E2 | -------ENIHNY | 46 | NAK | QHSWSIPYT | 48 |
| 3F6 | -ESVEYSGASL | 56 | AAS | QQSRKVPST | 58 |
| 1F10 | -ESVEYSGASL | 66 | AAS | QQSRKVPST | 68 |
| 6D11 | -ESVEYSGASL | 76 | AAS | QQSRKVPST | 78 |
| 3D11 | -------SSVSY | 86 | EIS | QQWSYP-FT | 88 |
| 2F2 | -------SSVSY | 101 | DTS | QQWSSYPPT | 103 |
| 4C1 | -ESVEYSGASL | 106 | AAS | QQSRKVPST | 108 |
| 6B2 | -ESVDYSGASL | 121 | AAS | QQSRKVPST | 123 |
| 2B8 | -ESVEYSGASL | 126 | AAS | QQSRKVPST | 128 |
| 4C5 | -ESVEYGASL | 136 | AAS | QQSRKVPNT | 138 |
| | . | | . | .: * | |
| 5A10 | -------SSVSY | 16 | DTS | QQWSSYPPT | 18 |
| 3F6 | -ESVEYSGASL | 56 | AAS | QQSRKVPST | 58 |
| 3D11 | -------SSVSY | 86 | EIS | QQWSYP-FT | 88 |

FIG. 8B

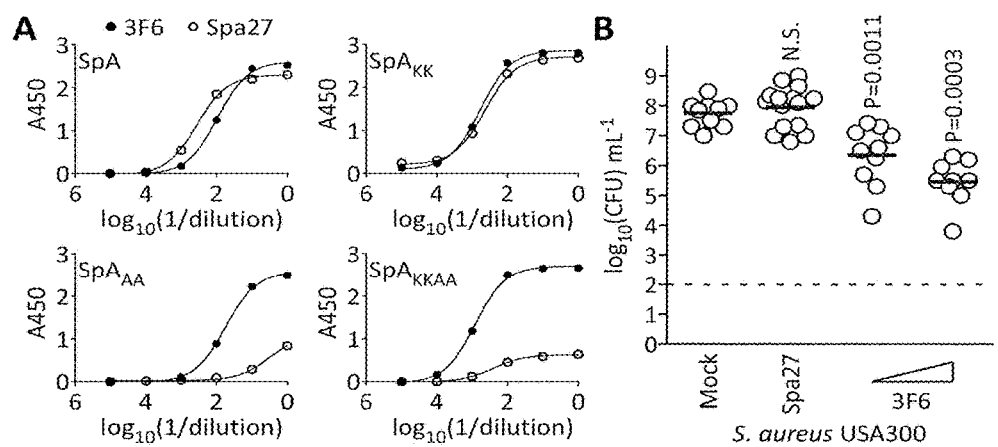
FIG. 9A-B

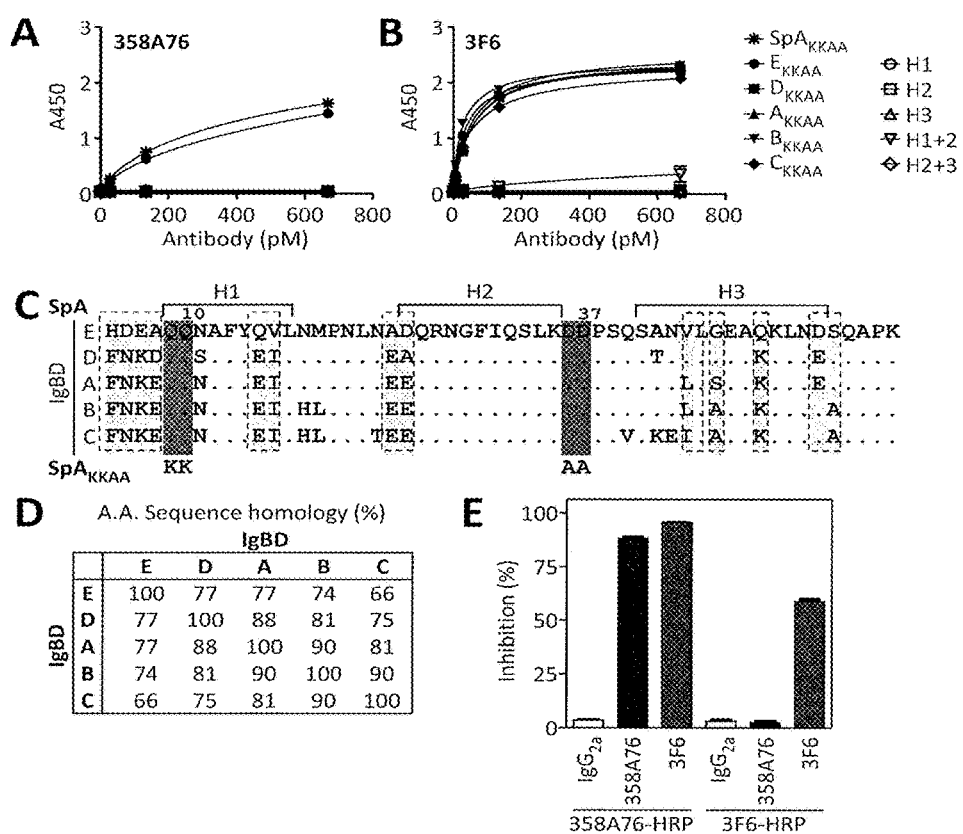
FIG. 10A-E

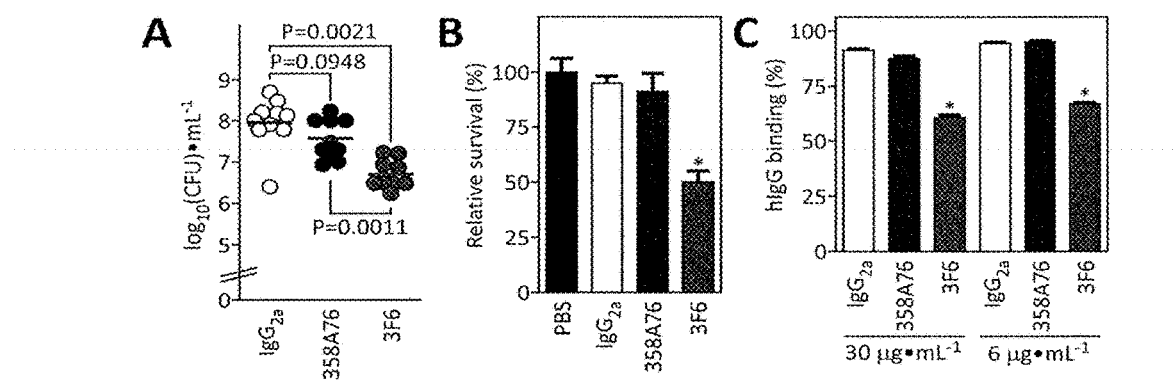
FIG. 11A-C

COMPOSITIONS AND METHODS RELATED TO ANTIBODIES TO STAPHYLOCOCCAL PROTEIN A

This application is a divisional application of U.S. patent application Ser. No. 14/238,811 filed Mar. 12, 2014, which is a national phase application under 35 U.S.C. § 371 of International Application No. PCT/US2012/050991 filed Aug. 15, 2012, which claims priority to U.S. Provisional Patent Application Ser. No. 61/523,751 filed on Aug. 15, 2011, Ser. No. 61/615,083 filed on Mar. 23, 2012, Ser. No. 61/618,417 filed on Mar. 30, 2012, and Ser. No. 61/674,135 filed on Jul. 20, 2012, all of which are incorporated herein by reference in their entirety.

This invention was made with government support under AI52747 and AI92711 from the National Institute of Allergy and Infectious Diseases (NIAID) and 1-U54-AI-057153 awarded by the National Institutes of Health. The government has certain rights in the invention.

FIELD OF THE INVENTION

The present invention relates generally to the fields of immunology, microbiology, and pathology. More particularly, it concerns methods and compositions involving antibodies to bacterial proteins and bacterial peptides used to elicit such antibodies. The proteins include Staphylococcal protein A (SpA).

BACKGROUND

The number of both community acquired and hospital acquired infections have increased over recent years with the increased use of intravascular devices. Hospital acquired (nosocomial) infections are a major cause of morbidity and mortality, more particularly in the United States, where they affect more than 2 million patients annually. The most frequent nosocomial infections are urinary tract infections (33% of the infections), followed by pneumonia (15.5%), surgical site infections (14.8%) and primary bloodstream infections (13%) (Emorl and Gaynes, 1993).

*Staphylococcus aureus*, Coagulase-negative *Staphylococci* (mostly *Staphylococcus epidermidis*), *enterococcus* spp., *Escherichia coli* and *Pseudomonas aeruginosa* are the major nosocomial pathogens. Although these pathogens almost cause the same number of infections, the severity of the disorders they can produce combined with the frequency of antibiotic resistant isolates balance this ranking towards *S. aureus* and *S. epidermidis* as being the most significant nosocomial pathogens.

*Staphylococcus* can cause a wide variety of diseases in humans and other animals through either toxin production or invasion. Staphylococcal toxins are a common cause of food poisoning, as the bacteria can grow in improperly-stored food.

*Staphylococcus epidermidis* is a normal skin commensal, which is also an important opportunistic pathogen responsible for infections of impaired medical devices and infections at sites of surgery. Medical devices infected by *S. epidermidis* include cardiac pacemakers, cerebrospinal fluid shunts, continuous ambulatory peritoneal dialysis catheters, orthopedic devices and prosthetic heart valves.

*Staphylococcus aureus* is the most common cause of nosocomial infections with a significant morbidity and mortality. It is the cause of some cases of osteomyelitis, endocarditis, septic arthritis, pneumonia, abscesses and toxic shock syndrome.

*S. aureus* can survive on dry surfaces, increasing the chance of transmission. Any *S. aureus* infection can cause the staphylococcal scalded skin syndrome, a cutaneous reaction to exotoxin absorbed into the bloodstream. *S. aureus* can also cause a type of septicemia called pyaemia that can be life-threatening. Methicillin-resistant *Staphylococcus aureus* (MRSA) has become a major cause of hospital-acquired infections.

*S. aureus* and *S. epidermidis* infections are typically treated with antibiotics, with penicillin being the drug of choice, but vancomycin being used for methicillin resistant isolates. The percentage of staphylococcal strains exhibiting wide-spectrum resistance to antibiotics has increased, posing a threat to effective antimicrobial therapy. In addition, the recent appearance of vancomycin-resistant *S. aureus* strain has aroused fear that MRSA strains for which no effective therapy is available are starting to emerge and spread.

An alternative approach to antibiotics in the treatment of staphylococcal infections has been the use of antibodies against staphylococcal antigens in passive immunotherapy. Examples of this passive immunotherapy involves administration of polyclonal antisera (WO00/15238, WO00/12132) as well as treatment with monoclonal antibodies against lipoteichoic acid (WO98/57994).

The first generation of vaccines targeted against *S. aureus* or against the exoproteins it produces have met with limited success (Lee, 1996) and there remains a need to develop additional therapeutic compositions for treatment of *staphylococcus* infections.

SUMMARY OF THE INVENTION

*Staphylococcus aureus* is the most frequent cause of bacteremia and hospital-acquired infection in the United States. An FDA approved vaccine that prevents staphylococcal disease is currently unavailable.

In certain embodiments there are antibody compositions that inhibit, ameliorate, and/or prevent Staphylococcal infection. In particular embodiments, there is a polypeptide that is capable of binding a Staphylococcal SpA protein. The term polypeptide is understood to mean one or more amino acid or polypeptide chains. For example, the term polypeptide may refer to a single polypeptide chain comprising a heavy or light chain or a coupled heavy and light chain. The term polypeptide may also refer to an immunoglobulin (Ig) monomer, comprising four polypeptide chains; two heavy and two light chains. The term polypeptide may also refer to dimeric, trimeric, tetrameric or pentameric Ig molecules.

Moreover, in certain embodiments, this SpA-binding polypeptide is distinguished from other SpA antibodies because it has properties that are based on being an antibody or derived from an antibody generated using a SpA variant as an antigen—not a SpA wild-type protein. The SpA variant has 1, 2, 3, 4, 5 or more alterations in 1, 2, 3, 4 and/or 5 of the A, B, C, D, and/or E domains. Furthermore, as discussed herein, these Spa binding polypeptides are capable of specifically binding such SpA variants, including but not limited to a KKAA domain variation in all five domains as discussed below.

Certain embodiments are directed to a recombinant peptide comprising 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50 amino acids in length, including all values and ranges there between, that are at least 80, 85, 90, 95, 96, 97, 98, 99, or 100% identical to amino acid segments of Staphylococcal SpA (SEQ ID NO:1). For example, the amino acid segment(s) from a Staphylococcal SpA may be from a non-toxogenic SpA mutant polypeptide (e.g., SpA$_{KKAA}$). PCT Publication No. WO 2011/005341 and PCT Appln. No. PCT/US11/42845, each incorporated herein by reference, provide a number of non-toxigenic SpA mutant polypeptides and methods for using the same. In further aspects, there are antibodies that specifically bind one or more of these particular amino acid segments.

Embodiments also provide for the use of SpA antibodies in methods and compositions for the treatment of bacterial and/or staphylococcal infection. In certain embodiments, compositions are used in the manufacture of medicaments for the therapeutic and/or prophylactic treatment of bacterial infections, particularly *staphylococcus* infections. Furthermore, in some embodiments there are methods and compositions that can be used to treat (e.g., limiting staphylococcal abscess formation and/or persistence in a subject) or prevent bacterial infection.

Certain aspects are directed to methods of reducing *Staphylococcus* infection or abscess formation comprising administering to a patient having or suspected of having a *Staphylococcus* infection an effective amount of one or more purified polypeptides or proteins that specifically bind a Staphylococcal SpA polypeptide. It is contemplated that this polypeptide (or protein) may be referred to as an antibody by virtue of it being a polypeptide or protein with amino acid sequences of or derived from one or more CDR regions of an antibody. Any embodiment discussed herein in the context of an antibody may be implemented with respect to a polypeptide or protein so long as the polypeptide or protein has one or more amino acid regions that has at least 60% identity or homology across the entire region of a CDR from an antibody that is capable of specifically binding a SpA variant lacking specific Ig-binding activity The Spa binding polypeptide can be a purified polyclonal antibody, a purified monoclonal antibody, a recombinant polypeptide, or a fragment thereof. In certain aspects the polypeptide is an antibody that is humanized, which means the nonvariable portion of the antibody has been altered in order to simulate the constant regions found in human antibodies. Thus, it is contemplated that a humanized antibody is one that has the CDR sequences of a non-human antibody (or at least amino acid sequences that are derived from such sequences, i.e., are at least 80% identical).

In certain other embodiments, the antibody is a human antibody. In still further aspects the antibody is a recombinant antibody segment. In certain aspects a monoclonal antibody includes one or more of 5A10, 8E2, 3A6, 7E2, 3F6, 1F10, 6D11, 3D11, 5A11, 1B10, 4C1, 2F2, 8D4, 7D11, 2C3, 4C5, 6B2, 4D5, 2B8 or 1H7 described in Tables 1-2 below and in Table 5, incorporated herein by reference. An antibody or polypeptide can be administered at a dose of 0.1, 0.5, 1, 5, 10, 50, 100 mg or µg/kg to 5, 10, 50, 100, 500 mg or µg/kg. The recombinant antibody segment can be operatively coupled to a second recombinant antibody segment. In certain aspects the second recombinant antibody segment binds a second Staphylococcal protein. The method can further comprise administering a second antibody that binds a second Staphylococcal protein. In certain aspects the method further comprises administering an antibiotic.

Embodiments are directed to monoclonal antibody polypeptides, polypeptides having one or more segments thereof, and polynucleotides encoding the same. In certain aspects a polypeptide can comprise all or part of the heavy chain variable region and/or the light chain variable region of SpA specific antibodies. In a further aspect, a polypeptide can comprise an amino acid sequence that corresponds to a first, second, and/or third complementary determining regions (CDRs) from the light variable chain and/or heavy variable chain of an antibody, e.g., a SpA-specific antibody. Additionally an antibody or binding polypeptide may have a binding region comprising an amino acid sequence having, having at least, or having at most 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identity or homology (substitution with a conserved amino acid) (or any range derivable therein) with 1, 2, 3, 4, 5, or 6 CDR sequences discussed herein, including any of SEQ ID NOs: 11-13, 21-23, 31-33, 41-43, 51-53, 61-63, 71-73, 81-83, 91-93, 96-98, 111-113, 116-118, 126-128, 131-133, 16-18, 26-28, 36-38, 46-48, 56-58, 66-68, 76-78, 86-88, 101-103, 106-108, 121-123, 136-138, 141-143. In specific embodiments, an antibody having all or part of one or more CDRs disclosed herein has been humanized in non-CDR regions. In further embodiments, the CDR regions disclosed herein may be changed by 1, 2, 3, 4, 5, 6, 7 or 8 amino acids per CDR, which may be instead of or in addition to humanization. In some embodiments, a change may be a deletion or addition of 1, 2, or 3 amino acids, or it may be a substitution of any amino acid, which may or may not be with an amino acid that is a conserved an amino acid.

In some embodiments, a SpA binding polypeptide or antibody has one, two, three, four, five, six, or seven CDRs that have 40, 45, 50, 55, 60, 65, 70, 75, 80, 85, 90, 95, 96, 97, 98, 99, 100% identity with a consensus sequence identified for that CDR, such as is shown in Tables 7-17. It is contemplated that in some embodiments, a SpA binding polypeptide or antibody has an amino acid sequence corresponding to CDR1, CDR2, and CDR3 of a light chain variable region and a CDR1, CDR2, and CDR3 of a heavy chain variable region. As discussed herein the amino acid sequence corresponding to a CDR may have a percent identity or homology to a CDR discussed herein. In certain embodiments, the consensus sequence is SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158 or SEQ ID NO:159. In particular embodiments, the SpA binding polypeptide or antibody has a consensus sequence from a monoclonal antibody for CDR1, CDR2, and/or CDR3 of the light chain variable region. Alternatively or additionally, the SpA binding polypeptide or antibody has a consensus sequence from a monoclonal antibody for CDR1, CDR2, and/or CDR3 of a heavy chain variable region. It is further contemplated that a SpA binding polypeptide or antibody may have a mix of CDRs based on consensus sequence(s) and/or sequences with identity or homology to a particular CDR.

In some embodiments a SpA binding polypeptide or antibody has one or more consensus sequences with respect to 3F6. In particular embodiments, the SpA binding polypeptide or antibody has a consensus sequence from 3F6 for CDR1, CDR2, and/or CDR3 of the light chain variable region. Alternatively or additionally, the SpA binding polypeptide or antibody has a consensus sequence from 3F6 for CDR1, CDR2, and/or CDR3 of a heavy chain variable region.

In certain embodiments, an SpA antibody or binding polypeptide comprises an amino acid sequence that is at least 40% identical to one or more antibody CDR domains from a SpA-binding antibody wherein the polypeptide specifically binds at least two Spa Ig binding domains A, B, C, D, and E of a Staphylococcal protein A polypeptide variant that lacks non-specific Ig-binding activity. Further embodiments of this aspect are contemplated below.

In yet other embodiments, a purified polypeptide that specifically binds to a SpA variant polypeptide lacking specific Ig-binding activity and wherein the polypeptide has an association constant of $0.5 \times 10^9 M^{-1}$ or greater for at least two and up to five Spa IgG binding domains $A_{KKAA}$, $B_{KKAA}$, $C_{KKAA}$, $D_{KKAA}$ and $E_{KKAA}$ is contemplated. Further embodiments of this embodiment are contemplated below.

In certain aspects, a polypeptide comprises all or part of an amino acid sequence corresponding to the MAb 3D11 variable (VDJ) heavy chain amino acid sequence

QSGPELMKPGASVKISCKASGYSFTSYYMHWVKQSHGKSLEWIGYIDPFN

GGTSYNQKFKGKATLTVDKSSSTAYMHLSSLTSEDSAVYYCARYGYDGTF

YAMDYWGQGTSVTVSS.

CDRs are indicated in bold underline. CDRs are regions within antibodies where the antibody complements an antigen's shape. Thus, CDRs determine the protein's affinity and specificity for specific antigens. From amino to carboxy terminus the CDRs are CDR1, CDR2, and CDR3. In certain aspects, a polypeptide can comprise 1, 2, and/or 3 CDRs from the variable heavy chain of MAb 3D11, for example, SEQ ID NO:81, SEQ ID NO:82, and/or SEQ ID NO:83. In further embodiments, an antibody may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 3D11 variable (VJ) light chain amino acid sequence

RIVLTQSPAITAASLGQKVTITCSASSSVSYMHWYQQKSGTSPKPWIYEI

SKLASGVPARFSGSGSGTSYSLTISSMEAEDAAIYYCQQWSYPFTFGSGT

KLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 3D11, for example, SEQ ID NO:86, SEQ ID NO:87, and/or SEQ ID NO:88. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 3D11, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 3D11.

In certain aspects, a polypeptide comprises all or part of an amino acid sequence corresponding to the MAb 3F6 variable (VDJ) heavy chain amino acid sequence

EVQLVETGGGLVQPKGSLKLSCAASGFTFNTNAMNWVRQAPGKGLEWVAR

IRSKSNNYATYYADSVKDRFSISRDDSQNMLSLQMNNLKTEDTAIYYCVT

EHYDYDYYVMDYWGQGTSVXSPQ.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 3F6, for example, SEQ ID NO:51, SEQ ID NO:52, and/or SEQ ID NO:53. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 3F6 variable (VJ) light chain amino acid sequence

IVLTQSPASLAVSLGQRATISCRASESVEYSGASLMQWYQHKPGQPPKLL

IYAASNVESGVPARFSGSGSGTDFSLNIHPVEEDDIAMYFCQQSRKVPST

FGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 3F6, for example, SEQ ID NO:56, SEQ ID NO:57, and/or SEQ ID NO:58. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 3F6, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 3F6.

In certain aspects, a polypeptide comprises all or part of an amino acid sequence corresponding to the MAb 5A10 variable (VDJ) heavy chain amino acid sequence EVKLVESGGGLVKPGGSLKLSCAASGFAFSNYDMSWVRQTPEKRLEWVATISSGGTYPYYPDSVKGRFTISRDNAKNTLYLQLSSLRSEDTALYYCARGGFLITTRDYYAMDYWGQGTSVTVSS.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 5A10, for example, SEQ ID NO:11, SEQ ID NO:12, and/or SEQ ID NO:13. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 5A10 variable (VJ) light chain amino acid sequence TIVLTQSPAIMSASPGEKVTMTCSASSSVSYMYWYQQKPGSSPRLLIYDTSNLASGVPVRFSGSGSGTSYSLTISRMEAEDAATYYCQQWSSYPPTFGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 5A10, for example, SEQ ID NO:16, SEQ ID NO:17, and/or SEQ ID NO:18. In further embodiments, a polypeptide may CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 5A10, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 5A10.

In certain aspects, a polypeptide comprises all or part of an amino acid sequence corresponding to the MAb 2F2 variable (VDJ) heavy chain amino acid sequence VKLVESGGDLVKPGGSLKLSCAASRFTFSSYVMSWVRQTPEKRLEWVASIGSGGTTYYPDTVKGRFTISRDNARNILYLQMSSLRSDDTAMYYCTRGRGYGFAWYFDVWGAGTTVTVSS.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 2F2, for example, SEQ ID NO:96, SEQ ID NO:97, and/or SEQ ID NO:98. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 2F2 variable (VJ) light chain amino acid sequence TIVLTQSPAIMSASPGEKVTMTCSASSSVSYMYWYQQKPGSSPRLLIYDTSNLASGVPVRFSGSGSGTSYSLTISRMEAEDAATYYCQQWSSYPPTFGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 2F2, for example, SEQ ID NO:101, SEQ ID NO:102, and/or SEQ ID NO:103. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 2F2, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 2F2.

In certain aspects, a polypeptide comprises all or part of an amino acid sequence corresponding to the MAb 4C5 variable (VJ) light chain amino acid sequence

DIVLTQSPASLAVSLGQRATISCRASESVEYYGASLMQWYQQKSGQPPKL

LIYAASNVESGVPARFSGSGSGTDFSLNIHPVEEDDIAMYFCQQSRKVPN

TFGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 4C5, for example, SEQ ID NO:136, SEQ ID NO:137, and/or SEQ ID NO:138. In further embodiments, a polypeptide may CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 4C5, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 4C5.

In certain aspects, a polypeptide comprises all or part of an amino acid sequence corresponding to the MAb 4D5 variable (VJ) light chain amino acid sequence

EIVLTQSPAITAASLGQKVTITCSASSSVSYMHWYHQKSGTSPKPWIYET

SKLASGVPVRFSGSGSGTSYSLTISSMEAEDAAIYYCQQWSYPFTFGSGT

KLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 4D8, for example, SEQ ID NO:141, SEQ ID NO:142, and/or SEQ ID NO:143. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 5A11 variable (VDJ) heavy chain amino acid sequence

EVQLVESGGGLVKPGGSLKLSCAASGFTFSDYYMYWVRQTPEKRLEWVAT

ISDGGTYTYYPDSVKGRFTISRDNAKNNLYLQMSSLKSEDTAMYYCARDR

DDYDEGPYFDYWGQGTTLTVSS.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 5A11, for example, SEQ ID NO:91, SEQ ID NO:92, and/or SEQ ID NO:93. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 6B2 variable (VJ) light chain amino acid sequence

DIVLTQSPASLAVSLGQRATISCRASESVDYSGASLMQWYQHKPGQPPRL

LIYAASNVESGVPARFSGSGSGTDFSLNIHPVEEDDIAMYFCQQSRKVPS

TFGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 6B2, for example, SEQ ID NO:121, SEQ ID NO:122, and/or SEQ ID NO:123. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 8E2 variable (VDJ) heavy chain amino acid sequence KVQLQQSGAGLVKPGASVKLSCKASGYTFTEYSIHWVKQSSGQGLEWIGWFYPGSGYIKYNEKFKDKATLTADKSSSTVYMEFSRLTSEDSAVYFCARHGYGNYVGYAMDYWGQGTSVTVSS.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 8E2, for example, SEQ ID NO:21, SEQ ID NO:22, and/or SEQ ID NO:23. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 8E2 variable (VJ) light chain amino acid sequence DIQMTQSPASLSASVGETVTITCRASEIIYSYLAWYQQKQGKSPQLLVYFAKTLAEGVPSRFSGSGSGTQFSLKINSLQPEDFGIYYCQHHYGTPYTFGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 8E2, for example, SEQ ID NO:26, SEQ ID NO:27, and/or SEQ ID NO:28. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 8E2, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 8E2.

In certain aspects, a polypeptide comprises all or part of an amino acid sequence corresponding to the MAb 3A6 variable (VDJ) heavy chain amino acid sequence QIQLVQSGPELKKPGETVKISCKASGYNFTDYSMHWVKQAPGKGLKWVGWINTETAESTYADDFKGRFAFSLETSASTAYLQINSLKDEDTATFFCAHFDCWGQGTTLTVSS.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 3A6, for example, SEQ ID NO:31, SEQ ID NO:32, and/or SEQ ID NO:33. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 3A6 variable (VJ) light chain amino acid sequence DVVMTQISLSLPVTLGDQASISCRASQSLVHSNGNTYLNWYLQKPGQSPK LLIHKVSNRFSGVPDRFSGSGSGTDFTLKISRVEAEDLGVYFCSQITYVPWTFGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 3A6, for example, SEQ ID NO:36, SEQ ID NO:37, and/or SEQ ID NO:38. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 3A6, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 3A6.

In certain aspects, a polypeptide comprises all or part of an amino acid sequence corresponding to the MAb 6D11 variable (VDJ) heavy chain amino acid sequence QVQLQQSGAELVRPGTSVKVSCKASGNAFTNYLIEWIKQRPGQGLEWIGVINPGSGITNYNEKFKGKATLTADKSSNTAYMQLSSLSSDDSAVYFCSGSANWFAYWGQGTLVTVSA.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 6D11, for example, SEQ ID NO:71, SEQ ID NO:72, and/or SEQ ID NO:73. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 6D11 variable (VJ) light chain amino acid sequence HCAHPSPASLAVSLGQRASISCRASESVEYSGASLMQWYQHKPGQPPKLLIYAASNVESGVPVRFSGSGSGTDFSLNIHPVEEDDIAMYFCQQSRKVPSTFGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 6D11, for example, SEQ ID NO:76, SEQ ID NO:77, and/or SEQ ID NO:78. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 6D11, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 6D11.

In certain aspects, a polypeptide comprises all or part of an amino acid sequence corresponding to the MAb 8D4 variable (VDJ) heavy chain amino acid sequence QVQLQQSGAELVRPGASVKISCKAFGSTFTNHHINWVKQRPGQGLDWIGYLNPYNDYTNYNQKFKGKATLTIDKSSSTAYLELSSLTSEDSAVYYCATITFDSQXQ.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 8D4, for example, SEQ ID NO:111, SEQ ID NO:112, and/or SEQ ID NO:113. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 1F10 variable (VDJ) heavy chain amino acid sequence KELISSKSEEEKWPGTSVKVSCKASGNAFTNYLIEWIKQRPGQGLEWIGVINPGSGITNYNEKFKGKATLTADKSSNTAYMQLSSLSSDDSAVYFCSGSANWFAYWGQGTLVTVSA.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 1F10, for example, SEQ ID NO:61, SEQ ID NO:62, and/or SEQ ID NO:63. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 1F10 variable (VJ) light chain amino acid sequence. CDRs are indicated in bold underline CSPSPASLAVSLGQRATISCRASESVEYSGASLMQWYQHKPGQPPKLLIYAASNVESGVPARFSGSGSGTDFSLNIHPVEEDDIAMYFCQQSRKVPSTFGGGTKLEIK.

From amino to carboxy terminus the CDRs are CDR1, CDR2, and CDR3. In certain aspects, a polypeptide can comprise 1, 2, and/or 3 CDRs from the variable light chain of MAb 1F10, for example, SEQ ID NO:66, SEQ ID NO:67, and/or SEQ ID NO:68. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 1F10, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 1F10.

In certain aspects, a polypeptide comprises all or part of an amino acid sequence corresponding to the MAb 4C1 variable (VJ) light chain amino acid sequence. CDRs are indicated in bold underline VLTQSPASLAVSLGQRATISCRASESVEYSGASLMQWYQHKPGQPPKLLIYAASNVESGVPARFSGSGSGTDFSLNIHPVEEDDIAMYFCQQSRKVPSTFGGGTKLEIK.

From amino to carboxy terminus the CDRs are CDR1, CDR2, and CDR3. In certain aspects, a polypeptide can comprise 1, 2, and/or 3 CDRs from the variable light chain of MAb 4C1, for example, SEQ ID NO:106, SEQ ID NO:107, and/or SEQ ID NO:108. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 2B8 variable (VJ) light chain amino acid sequence FFGVSLGQRASISCRASESVEYSGASLIQWYQHKPGQPPKLLIYAASNVESGVPVRFSGSGSGTDFSLNIHPVEEDDIAMYFCQQSRKVPSTFGGGTKLEIK.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 2B8, for example, SEQ ID NO:126, SEQ ID NO:127, and/or SEQ ID NO:128. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 2C3 variable (VDJ) heavy chain amino acid sequence EVKLVESGGGLVKPGGSLKLSCAASGFTFSNYDMSWVRQTPEKRLEWVATISSGGTYPYYPDSVKGRFTISRDNAENTLYLQLSSLRSEDTALYYCARGGFLITTRDYYAMDYWGQGTSVTVSS.

CDRs are indicated in bold underline. From amino to carboxy terminus the CDRs are CDR1, CDR2, and CDR3. In certain aspects, a polypeptide can comprise 1, 2, and/or 3 CDRs from the variable heavy chain of MAb 2C3, for example, SEQ ID NO:131, SEQ ID NO:132, and/or SEQ ID NO:133. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 7E2 variable (VDJ) heavy chain amino acid sequence QIQLVQSGPELKKPGETVKISCKASGYTFTDYSVHWVKQAPGKGLKWMAWINTATGEPTFADDFKGRFAFSLETSARTAYLQINNLKNEDTATYFCAPQLTGPFAYWGHGTLVTVSA.

CDRs are indicated in bold underline. CDRs are regions within antibodies where the antibody complements an antigen's shape. Thus, CDRs determine the protein's affinity and specificity for specific antigens. From amino to carboxy terminus the CDRs are CDR1, CDR2, and CDR3. In certain aspects, a polypeptide can comprise 1, 2, and/or 3 CDRs from the variable heavy chain of MAb 7E2, for example, SEQ ID NO:41, SEQ ID NO:42, and/or SEQ ID NO:43. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain aspects, a polypeptide comprises all or part of an amino acid sequence corresponding to the MAb 7E2 variable (VJ) light chain amino acid sequence DIQMTQSPASLSASVGETVTITCRASENIHNYLAWYQQKQGKSPQLLVYN
AKTLTDGVPSRFSGSGSGTQFSLKINSLQAGDFGSYYCQHSWSIPYTFGG
GTRLQIRR.

CDRs are indicated in bold underline. From amino to carboxy terminus the CDRs are CDR1, CDR2, and CDR3. In certain aspects, a polypeptide can comprise 1, 2, and/or 3 CDRs from the variable light chain of MAb 7E2, for example, SEQ ID NO:46, SEQ ID NO:47, and/or SEQ ID NO:48. In further embodiments, a polypeptide may have CDRs that have 1, 2, and/or 3 amino acid changes (addition of 1 or 2 amino acids, deletions or 1 or 2 amino acids or substitution) with respect to these 1, 2, or 3 CDRs. In further embodiments, an antibody may be alternatively or additionally humanized in regions outside the CDR(s) and/or variable region(s). In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In other embodiments, a polypeptide or protein comprises 1, 2, 3, 4, 5, or 6 CDRs from the either or both of the light and heavy variable regions of mAb 7E2, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of mAb 7E2.

In still further aspects, a polypeptide of the embodiments comprises one or more amino acid segments of the any of the amino acid sequences disclosed herein. For example, a polypeptide can comprise 1, 2, 3, 4, 5, 6, 7, 8, 9, 10 or more amino acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 amino acids in length, including all values and ranges there between, that are at least 80, 85, 90, 95, 96, 97, 98, 99, or 100% identical to any of the amino acid sequences disclosed herein. In certain aspects the amino segment(s) are selected from one of the amino acid sequences of a SpA-binding antibody as provided in Table 5.

In still further aspects, a polypeptide of the embodiments comprises an amino acid segment of the any of the amino acid sequences disclosed herein, wherein the segment begins at amino acid position 1, 2, 3, 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in any sequence provided herein and ends at amino acid position 4, 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 in the same provided sequence. In certain aspects the amino segment(s), or portions thereof, are selected from one of the amino acid sequences of a SpA-binding antibody as provided in Table 5.

In yet further aspects, a polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a SpA-binding antibody (as provided in Table 5). For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 a SpA-binding antibody as provided in Table 5.

In further aspects, a nucleic acid molecule of the embodiments comprises one or more nucleic acid segments of the any of the nucleic acid sequences disclosed herein. For example, a nucleic acid molecule can comprise 1, 2, 3, 4, 5, 6, 7, 8, 9, 10 or more nucleic acid segments comprising about, at least or at most 5, 6, 7, 8, 9, 10, 11, 12, 13, 14, 15, 16, 17, 18, 19, 20, 21, 22, 23, 24, 25 to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more nucleotides in length, including all values and ranges there between, that are at least 80, 85, 90, 95, 96, 97, 98, 99, or 100% identical (or any range derivable therein) to any of the nucleic acid sequences disclosed herein. In certain aspects, the nucleic acid segment(s) are selected from one of the nucleic acid sequences encoding portions of SpA-binding antibodies as provided in Table 5.

In yet further aspects, a nucleic acid molecule of the embodiments comprises a nucleic acid segment that is at least 80, 85, 90, 95, 96, 97, 98, 99, or 100% identical (or any range derivable therein) to a sequence encoding a V, VJ, VDJ, D, DJ, J or CDR domain of a SpA-binding antibody as provided in Table 5. For example, a nucleic acid molecule may comprise 1, 2 or 3 nucleic acid segments that are at least 80, 85, 90, 95, 96, 97, 98, 99, or 100% identical (or any range derivable therein) to sequences encoding CDRs 1, 2, and/or 3 a SpA-binding antibody as provided in Table 5.

In still further aspects, some embodiments provide a hybridoma cell line that produces a monoclonal antibody. In certain embodiments the hybridoma cell line is a line that produces the 5A10, 8E2, 3A6, 7E2, 3F6, 1F10, 6D11, 3D11, 5A11, 1B10, 4C1, 2F2, 8D4, 7D11, 2C3, 4C5, 6B2, 4D5, 2B8 or 1H7 monoclonal antibody, one or more of which may be deposited. In a further aspect, 1, 2, and/or 3 CDRs from the light and/or heavy chain variable region of a MAb can be comprised in a humanized antibody or variant thereof. In other embodiments, a bi-specific antibody is contemplated in which a binding polypeptide is capable of binding at least two different antigens.

Certain aspects are directed to methods of treating a subject having or suspected of having a *Staphylococcus* infection comprising administering to a patient having or suspected of having a *Staphylococcus* infection an effective amount of a purified antibody or binding polypeptide that specifically binds a Staphylococcal protein A.

In a further aspect methods are directed to treating a subject at risk of a *Staphylococcus* infection comprising administering to a patient at risk of a *Staphylococcus* infection an effective amount of an antibody or binding polypeptide that binds a Staphylococcal protein A polypeptide prior to infection with *Staphylococcus*.

Antibodies or binding polypeptides that are contemplated for use in these embodiments include those that are able to reduce bacterial load, increase survival, reduce bacterial abscess, confer protective immunity, reduce the number of days on antibiotic, reduce the risk of sepsis or septicemia, reduce the risk of shock, or provide some other protective effect.

Certain embodiments are directed to a antibody or binding polypeptide composition comprising an isolated and/or recombinant antibody or polypeptide that specifically binds a peptide segment as described above. In certain aspects the antibody or polypeptide has a sequence that is, is at least, or is at most 80, 85, 90, 95, 96, 97, 98, 99, or 100% identical (or any range derivable therein) to all or part of any monoclonal antibody provided herein. In still further aspects the isolated and/or recombinant antibody or polypeptide has, has at least, or has at most 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more contiguous amino acids from any of the sequences provided herein or a combination of such sequences.

In additional embodiments, there are pharmaceutical compositions comprising one or more polypeptides or antibodies or antibody fragments that are discussed herein. Such a composition may or may not contain additional active ingredients.

In certain embodiments there is a pharmaceutical composition consisting essentially of a polypeptide comprising one or more antibody fragments discussed herein. It is contemplated that the composition may contain non-active ingredients.

Certain aspects are directed to nucleic acid molecules encoding a heavy chain variable regions and/or light chain variable regions of an antibody that specifically binds SpA or a non-toxigenic SpA variant.

Other aspects are directed to pharmaceutical compositions comprising an effective anti-bacterial amount of an antibody that specifically binds to a peptide described above and a pharmaceutically acceptable carrier.

The term "providing" is used according to its ordinary meaning to indicate "to supply or furnish for use." In some embodiments, the protein is provided directly by administering a composition comprising antibodies or fragments thereof that are described herein.

The subject typically will have (e.g., diagnosed with a persistent staphylococcal infection), will be suspected of having, or will be at risk of developing a staphylococcal infection. Compositions include SpA binding polypeptides in amounts effective to achieve the intended purpose—treatment or protection of Staphylococcal infection. The term "binding polypeptide" refers to a polypeptide that specifically binds to a target molecule, such as the binding of an antibody to an antigen. Binding polypeptides may but need not be derived from immunoglobulin genes or fragments of immunoglobulin genes. More specifically, an effective amount means an amount of active ingredients necessary to provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods described herein, an effective amount or dose can be estimated initially from in vitro, cell culture, and/or animal model assays. For example, a dose can be formulated in animal models to achieve a desired response. Such information can be used to more accurately determine useful doses in humans.

Compositions can comprise an antibody or a cell that binds SpA. An antibody can be an antibody fragment, a humanized antibody, a monoclonal antibody, a single chain antibody or the like. In certain aspects, the SpA antibody is elicited by providing a SpA peptide or antigen or epitope that results in the production of an antibody that binds SpA in the subject. The SpA antibody is typically formulated in a pharmaceutically acceptable composition. The SpA antibody composition can further comprise at least 1, 2, 3, 4, 5, 6, 7, 8, 9, 10, 11, 12, 13, 14, 15, 16, 17, 18, or 19 for more staphylococcal antigens or immunogenic fragments thereof. Staphylococcal antigens include, but are not limited to all or a segment of Eap, Ebh, Emp, EsaB, EsaC, EsxA, EsxB, IsdA, IsdB, SdrC, SdrD, SdrE, ClfA, ClfB, Coa, Hla (e.g., H35 mutants), IsdC, SasF, vWbp, SpA and variants thereof (See U.S. Provisional Application Ser. No. 61/166,432, filed Apr. 3, 2009; Ser. No. 61/170,779, filed Apr. 20, 2009; and Ser. No. 61/103,196, filed Oct. 6, 2009; each of which is incorporated herein by reference in their entirety), 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety). The staphylococcal antigen, or immunogenic fragment or segment can be administered concurrently with the SpA antibody. The staphylococcal antigen or immunogenic fragment and the SpA antibody can be administered in the same or different composition and at the same or different times.

The SpA antibody composition can further comprise antibodies, antibody fragments or antibody subfragments to at least 1, 2, 3, 4, 5, 6, 7, 8, 9, 10, 11, 12, 13, 14, 15, 16, 17, 18, or 19 of more staphylococcal antigens or immunogenic fragments thereof. Staphylococcal antigens to which such antibodies, antibody fragments of antibody subfragments are directed include, but are not limited to all or a segment of Eap, Ebh, Emp, EsaB, EsaC, EsxA, EsxB, IsdA, IsdB, SdrC, SdrD, SdrE, ClfA, ClfB, Coa, Hla (e.g., H35 mutants), IsdC, SasF, vWbp, SpA and variants thereof (See U.S. Provisional Application Ser. No. 61/166,432, filed Apr. 3, 2009; 61/170,779, filed Apr. 20, 2009; and 61/103,196, filed Oct. 6, 2009; each of which is incorporated herein by reference in their entirety), 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety). The antibodies, antibody fragments or antibody subfragments to other staphylococcal antigens or immunogenic fragments thereof can be administered concurrently with the SpA antibody. The antibodies, antibody fragments or antibody subfragments to other staphylococcal antigens or immunogenic fragments thereof can be administered in the same or different composition to the SpA antibody and at the same or different times.

As used herein, the term "modulate" or "modulation" encompasses the meanings of the words "inhibit." "Modulation" of activity is a decrease in activity. As used herein, the term "modulator" refers to compounds that effect the function of a Staphylococcal bacteria, including potentiation, inhibition, down-regulation, or suppression of a protein, nucleic acid, gene, organism or the like.

Embodiments include compositions that contain or do not contain a bacterium. A composition may or may not include an attenuated or viable or intact staphylococcal bacterium. In certain aspects, the composition comprises a bacterium that is not a Staphylococci bacterium or does not contain Staphylococci bacteria. In certain embodiments a bacterial composition comprises an isolated or recombinantly expressed SpA antibody or a nucleic acid encoding the same. In still further aspects, the SpA antibody is multimerized, e.g., a dimer, a trimer, a tertramer, etc.

In certain aspects, a peptide or an antigen or an epitope can be presented as multimers of 1, 2, 3, 4, 5, 6, 7, 8, 9, 10 or more peptide segments or peptide mimetics.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Compositions such as antibodies, peptides, antigens, or immunogens may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated.

The term "SpA antibody" refers to polypeptides that bind SpA proteins from *staphylococcus* bacteria.

In further aspects a composition may be administered more than one time to the subject, and may be administered 1, 2, 3, 4, 5, 6, 7, 8, 9, 10, 15, 20 or more times. The administration of the compositions include, but is not limited to oral, parenteral, subcutaneous and intravenous administration, or various combinations thereof, including inhalation or aspiration.

Compositions are typically administered to human subjects, but administration to other animals that are capable of providing a therapeutic benefit against a *staphylococcus* bacterium are contemplated, particularly cattle, horses, goats, sheep and other domestic animals, i.e., mammals. In further aspects the *staphylococcus* bacterium is a *Staphylococcus aureus*. In still further aspects, the methods and compositions may be used to prevent, ameliorate, reduce, or treat infection of tissues or glands, e.g., mammary glands, particularly mastitis and other infections. Other methods include, but are not limited to prophylactically reducing bacterial burden in a subject not exhibiting signs of infection, particularly those subjects suspected of or at risk of being colonized by a target bacteria, e.g., patients that are or will be at risk or susceptible to infection during a hospital stay, treatment, and/or recovery.

Still further embodiments include methods for providing a subject a protective or therapeutic composition against a *staphylococcus* bacterium comprising administering to the subject an effective amount of a composition including (i) a SpA antibody; or, (ii) a nucleic acid molecule encoding the same, or (iii) administering an SpA antibody with any combination or permutation of bacterial proteins described herein.

The embodiments in the Example section are understood to be embodiments that are applicable to all aspects of the invention, including compositions and methods.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

FIGS. 8A-B: SpA$_{KKAA}$ mAb CDR alignments. Amino Acid sequences from CDRs (complementarity determining regions) obtained from hybridoma cell line Immunoglobulin genes were aligned using ClustalW2. An * (asterisk) indicates positions which have a single, fully conserved residue. : (colon) indicates conservation between groups of strongly similar properties—scoring>0.5 in the Gonnet PAM 250 matrix. . (period) indicates conservation between groups of weakly similar properties—scoring=<0.5 in the Gonnet PAM 250 matrix. mAb rank based on CFU reduction in the murine renal abscess model appears in superscript in front of mAb identifier. Mouse IgG isotype is indicated. AVFPMILW—Small (small+hydrophobic (incl.aromatic—Y)), DE—Acidic, RK—Basic—H, STYHCNGQ—Hydroxyl+sulfhydryl+amine+G.

FIGS. 9A-B: SpA monoclonal antibody (Spa27) fails to elicit protective immunity in mice. (A) ELISA examining the association SpA-mAb (Spa27) and SpA$_{KKAA}$-mAb (3F6) with immobilized wild-type protein A (SpA) and variants lacking immunoglobulin binding via Fcγ (SpA$_{KK}$), Fab (SpA$_{AA}$) or Fcγ and Fab (SpA$_{KKAA}$)(n=3). (B) Cohorts of animals (n=9-15) were immunized by intraperitoneal injection with either mock (PBS), Spa27 at 5 mg·kg$^{-1}$, or 3F6 at 5 or 50 mg·kg$^{-1}$. Twenty-four hours post immunization, animals were challenged with 5×10$^6$ CFU of *S. aureus* USA300. Four days post challenge, animals were euthanized to enumerate the staphylococcal load in kidneys.

FIGS. 10A-E: mAb 358A76.1 specifically recognizes the E domain of staphylococcal protein A. ELISA examining the association of (A) mAbs 358A76.1 and (B) 3F6 with immobilized non-toxigenic protein A variant (SpA$_{KKAA}$), each immunoglobulin binding domain (E$_{KKAA}$, D$_{KKAA}$, A$_{KKAA}$, B$_{KKAA}$, and C$_{KKAA}$), and synthetic linear peptides derived from the three helices (H1, H2, H3, H1+2, H2+3) of the E$_{KKAA}$ immunoglobulin binding domain (IgBD). (C) Alignment of amino acid sequences of the five IgBDs of protein A reveals amino acid residues in E domain that are different from the conserved amino acid residues of the remaining four IgBDs (dashed boxes). Amino acid residues substituted within non-toxigenic protein A are identified by gray boxes. (D) Amino acid sequence homology level was compared using ClustalW and the numbers represent the percent of amino acid homology between immunoglobulin binding domains. (E) The binding of horse radish peroxidase (HRP)-conjugated mAbs (358A76.1-HRP and 3F6-HRP) to SpA$_{KKAA}$ immobilized in an ELISA plate was assessed in a plate reader experiment where SpA$_{KKAA}$ was first incubated with isotype control antibody (IgG$_{2a}$) or mAbs (358A76.1 and 3F6) to identify competitive inhibition of antibodies that bind the same or closely related sites. Values at OD$_{405\ nm}$ were recorded and normalized for the interaction of SpA$_{KKAA}$ and HRP-conjugated SpA specific mAbs.

FIGS. 11A-C: SpA monoclonal antibody 358A76.1 fails to elicit protective immunity in mice. (A) Cohorts of animals (n=10) were immunized by intraperitoneal injection with either mock (IgG$_{2a}$ isotype control mAb), mAb 358A76.1 or mAb 3F6 at 5 mg·kg$^{-1}$. Twenty-four hours post immunization, animals were challenged via intravenous inoculation with 5×10$^6$ CFU of *S. aureus* USA300. Four days post challenge, animals were euthanized to enumerate the staphylococcal load in kidneys. (B) Anti-coagulated mouse blood was incubated with 5×10$^5$ CFU *S. aureus* USA300 (LAC) in the presence of IgG2a isotype control mAb, mAb 358A76.1 or mAb 3F6 (10 μg·ml$^{-1}$) for 30 minutes; staphylococcal survival was measured. (C) Isotype control antibodies, mAb 358A76.1 or mAb 3F6 were used to perturb the binding of human IgG to wild-type protein A (SpA) immobilized on ELISA plates. The values were normalized to the protein A interaction with human IgG in the absence of antibodies.

DETAILED DESCRIPTION OF THE INVENTION

Figure 1:
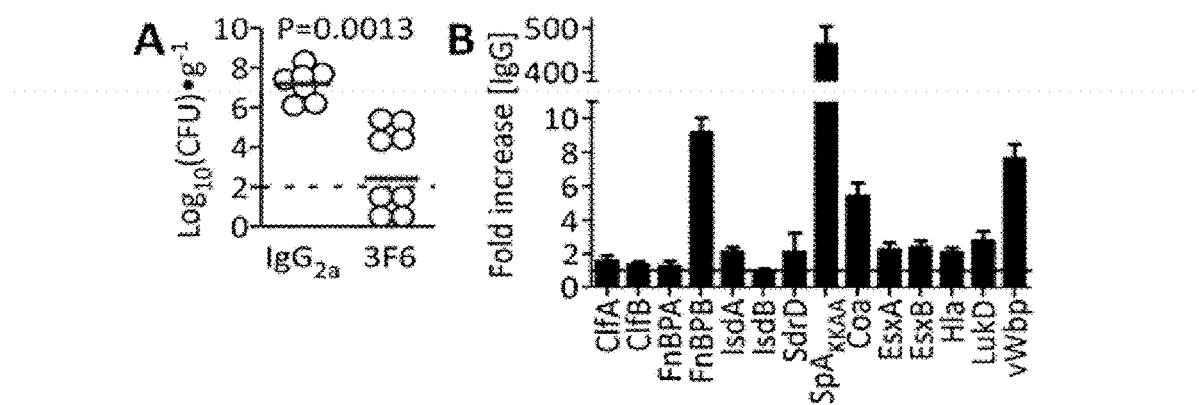
FIGS. 1A-B: $SpA_{KKAA}$-specific monoclonal antibodies (mAbs) protect mice against MRSA infection. Cohorts of animals (n=10) were immunized by intraperitoneal injection with either isotype control ($IgG_{2a}$) or $SpA_{KKAA}$-mAb (3F6) at 20 mg·kg$^{-1}$. After 24 hours post immunization, animals were challenged with $5\times10^6$ CFU of *S. aureus* MW2. (A) At 15 days post challenge, animals were euthanized to enumerate the staphylococcal load in kidneys. (B) Serum samples of mice infected for 15 days were analyzed for antibodies against the staphylococcal antigen matrix (ClfA, Clumping Factor A; ClfB, Clumping Factor B; FnBPA, Fibronectin Binding Protein A; FnBPB, Fibronectin Binding Protein B; IsdA, Iron surface determinant A; IsdB, Iron surface determinant B; SdrD, Serine-Aspartic acid repeat protein D; SpAKKAA, Non-toxigenic staphylococcal protein A; Coa, Coagulase; EsxA, Ess [ESAT-6 (Early Secreted Antigen Target 6 kDa)] secretion system] extracellular A; EsxB, Ess [ESAT-6 (Early Secreted Antigen Target 6 kDa)] secretion system] extracellular B; Hla, alpha-hemolysin; LukD, Leukocidin D; vWbp, von Willebrand binding protein). The values represent the fold increase of samples from mAb 3F6 treated animals over the isotype control animal sera samples (n=7 for $IgG_{2a}$, n=8 for 3F6). Data are the means and error bars represent ±SEM. Results in A-B are representative of two independent analyses.

*Staphylococcus aureus* is a commensal of the human skin and nares, and the leading cause of bloodstream, skin and soft tissue infections (Klevens et al., 2007). Recent dramatic increases in the mortality of staphylococcal diseases are attributed to the spread of methicillin-resistant *S. aureus* (MRSA) strains often not susceptible to antibiotics (Kennedy et al., 2008). In a large retrospective study, the incidence of MRSA infections was 4.6% of all hospital admissions in the United States (Klevens et al., 2007). The annual health care costs for 94,300 MRSA infected individuals in the United States exceed $2.4 billion (Klevens et al., 2007). The current MRSA epidemic has precipitated a public health crisis that needs to be addressed by development of a preventive vaccine (Boucher and Corey, 2008). To date, an FDA licensed vaccine that prevents *S. aureus* diseases is not available.

The inventors describe here staphylococcal Protein A-binding antibodies and the antigen binding determinants thereof. In particular, an array of monoclonal antibodies have been produced using a SpA mutant protein that lacks both toxicity (Fcγ interaction) and super antigen activity against B-cells (Fab interaction). Many of the antibodies were found to interact with SpA with high affinity and specificity. Importantly, the antibodies are able to neutralize the molecular mechanisms of staphylococcal protein A. Further, when administered to animals, the antibodies reduced bacterial load and abscess formation following challenge with virulent *S. aureus*. Because these molecules are able to block the immunosuppressive effects of SpA, such antibody may also enhance host immune response following staphylococcal infection. Thus, the SpA-binding molecules of the embodiments offer a new and effective avenue to treat or prevent staphylococcal disease.

I. SPA POLYPEPTIDES

Certain aspects of the embodiments concern SpA polypeptides, such as wild type SpA provided here as SEQ ID NO: 1. In certain aspect, however, the embodiments concern mutant or variant SpA polypeptides, such as polypeptides that lacks B-cell super antigen activity and/or non-specific immunoglobulin binding activity (i.e., binding the Ig that is not dependent upon the CDR sequence of the Ig). In particular, certain embodiments concern polypeptides (e.g., polypeptides comprising antibody CDR domains) that specifically bind to a SpA polypeptide that lacks B-cell super antigen activity and/or non-specific immunoglobulin binding activity.

The N-terminal part of protein A is comprised of four or five 56-61 amino acid residue immunoglobulin binding domains (IgBD A-E); SpA variants for use according to the embodiments can be, for example, full length SpA variant comprising a variant A, B, C, D, and/or E domain. In certain aspects, the SpA variant comprises or consists of the amino acid sequence that is 80, 90, 95, 98, 99, or 100% identical to the amino acid sequence of SEQ ID NO:7. In other embodiments the SpA variant comprises a segment of SpA. The SpA segment can comprise at least or at most 1, 2, 3, 4, 5 or more IgG binding domains. The IgG domains can be at least or at most 1, 2, 3, 4, 5 or more variant A, B, C, D, or E domains. In certain aspects the SpA variant comprises at least or at most 1, 2, 3, 4, 5, or more variant A domains. In a further aspect the SpA variant comprises at least or at most 1, 2, 3, 4, 5, or more variant B domains. In still a further aspect the SpA variant comprises at least or at most 1, 2, 3, 4, 5, or more variant C domains. In yet a further aspect the SpA variant comprises at least or at most 1, 2, 3, 4, 5, or more variant D domains. In certain aspects the SpA variant comprises at least or at most 1, 2, 3, 4, 5, or more variant E domains. In a further aspect the SpA variant comprises a combination of A, B, C, D, and E domains in various combinations and permutations. The combinations can include all or part of a SpA signal peptide segment, a SpA region X segment, and/or a SpA sorting signal segment. In other aspects the SpA variant does not include a SpA signal peptide segment, a SpA region X segment, and/or a SpA sorting signal segment. In certain aspects a variant A domain comprises a substitution at position(s) 7, 8, 34, and/or 35 of SEQ ID NO:4. In another aspect a variant B domain comprises a substitution at position(s) 7, 8, 34, and/or 35 of SEQ ID NO:6. In still another aspect a variant C domain comprises a substitution at position(s) 7, 8, 34, and/or 35 of SEQ ID NO:5. In certain aspects a variant D domain comprises a substitution at position(s) 9, 10, 36, and/or 37 of SEQ ID NO:2. In a further aspect a variant E domain comprises a substitution at position(s) 6, 7, 33, and/or 34 of SEQ ID NO:3.

In certain aspects, an SpA domain D variant or its equivalent can comprise a mutation at position 9 and 36; 9 and 37; 9 and 10; 36 and 37; 10 and 36; 10 and 37; 9, 36, and 37; 10, 36, and 37, 9, 10 and 36; or 9, 10 and 37 of SEQ ID NO:2. In a further aspect, analogous mutations can be included in one or more of domains A, B, C, or E.

In further aspects, the amino acid glutamine (Q) at position 9 of SEQ ID NO:2 (or its analogous amino acid in other SpA domains) can be replaced with an alanine (A), an asparagine (N), an aspartic acid (D), a cysteine (C), a glutamic acid (E), a phenylalanine (F), a glycine (G), a histidine (H), an isoleucine (I), a lysine (K), a leucine (L), a methionine (M), a proline (P), a serine (S), a threonine (T), a valine (V), a tryptophane (W), or a tyrosine (Y). In some aspects the glutamine at position 9 can be substituted with an arginine (R). In a further aspect, the glutamine at position 9 of SEQ ID NO:2, or its equivalent, can be substituted with a lysine or a glycine. Any 1, 2, 3, 4, 5, 6, 7, 8, 9, 10, or more of the substitutions can be explicitly excluded.

In another aspect, the amino acid glutamine (Q) at position 10 of SEQ ID NO:2 (or its analogous amino acid in other SpA domains) can be replaced with an alanine (A), an asparagine (N), an aspartic acid (D), a cysteine (C), a glutamic acid (E), a phenylalanine (F), a glycine (G), a histidine (H), an isoleucine (I), a lysine (K), a leucine (L), a methionine (M), a proline (P), a serine (S), a threonine (T), a valine (V), a tryptophane (W), or a tyrosine (Y). In some aspects the glutamine at position 10 can be substituted with an arginine (R). In a further aspect, the glutamine at position 10 of SEQ ID NO:2, or its equivalent, can be substituted with a lysine or a glycine. Any 1, 2, 3, 4, 5, 6, 7, 8, 9, 10, or more of the substitutions can be explicitly excluded.

In certain aspects, the aspartic acid (D) at position 36 of SEQ ID NO:2 (or its analogous amino acid in other SpA domains) can be replaced with an alanine (A), an asparagine (N), an arginine (R), a cysteine (C), a phenylalanine (F), a glycine (G), a histidine (H), an isoleucine (I), a lysine (K), a leucine (L), a methionine (M), a proline (P), a glutamine (Q), a serine (S), a threonine (T), a valine (V), a tryptophane (W), or a tyrosine (Y). In some aspects the aspartic acid at position 36 can be substituted with a glutamic acid (E). In certain aspects, an aspartic acid at position 36 of SEQ ID NO:2, or its equivalent, can be substituted with an alanine or a serine. Any 1, 2, 3, 4, 5, 6, 7, 8, 9, 10, or more of the substitutions can be explicitly excluded.

In another aspect, the aspartic acid (D) at position 37 of SEQ ID NO:2 (or its analogous amino acid in other SpA domains) can be replaced with an alanine (A), a an asparagine (N), an arginine (R), a cysteine (C), a phenylalanine (F), a glycine (G), a histidine (H), an isoleucine (I), a lysine (K), a leucine (L), a methionine (M), a proline (P), a glutamine (Q), a serine (S), a threonine (T), a valine (V), a tryptophane (W), or a tyrosine (Y). In some aspects the aspartic acid at position 37 can be substituted with a glutamic acid (E). In certain aspects, an aspartic acid at position 37 of SEQ ID NO:2, or its equivalent, can be substituted with an alanine or a serine. Any 1, 2, 3, 4, 5, 6, 7, 8, 9, 10, or more of the substitutions can be explicitly excluded.

In a particular embodiment the amino at position 9 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 9 of SEQ ID NO:2 is replaced by a glycine. In a further aspect the amino acid at position 9 of SEQ ID NO:2 is replaced by a lysine.

In a particular embodiment the amino at position 10 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 10 of SEQ ID NO:2 is replaced by a glycine. In a further aspect the amino acid at position 10 of SEQ ID NO:2 is replaced by a lysine.

In a particular embodiment the amino at position 36 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 36 of SEQ ID NO:2 is replaced by a serine. In a further aspect the amino acid at position 36 of SEQ ID NO:2 is replaced by an alanine.

In a particular embodiment the amino at position 37 of SEQ ID NO:2 (or an analogous amino acid in another SpA domain) is replaced by an alanine (A), a glycine (G), an isoleucine (I), a leucine (L), a proline (P), a serine (S), or a valine (V), In certain aspects the amino acid at position 37 of SEQ ID NO:2 is replaced by a serine. In a further aspect the amino acid at position 37 of SEQ ID NO:2 is replaced by an alanine.

In certain aspects the SpA variant includes a substitution of (a) one or more amino acid substitution in an IgG Fc binding sub-domain of SpA domain A, B, C, D, and/or E that disrupts or decreases binding to IgG Fc, and (b) one or more amino acid substitution in a $V_H3$ binding sub-domain of SpA domain A, B, C, D, and/or E that disrupts or decreases binding to $V_H3$. In still further aspects the amino acid sequence of a SpA variant comprises an amino acid sequence that is at least 50%, 60%, 70%, 80%, 90%, 95%, or 100% identical, including all values and ranges there between, to the amino acid sequence of SEQ ID NOs: 2-6.

In a further aspect the SpA variant includes (a) one or more amino acid substitution in an IgG Fc binding sub-domain of SpA domain D, or at a corresponding amino acid position in other IgG domains, that disrupts or decreases binding to IgG Fc, and (b) one or more amino acid substitution in a $V_H3$ binding sub-domain of SpA domain D, or at a corresponding amino acid position in other IgG domains, that disrupts or decreases binding to $V_H3$. In certain aspects amino acid residue F5, Q9, Q10, S11, F13, Y14, L17, N28, I31, and/or K35 (SEQ ID NO:2, QQNNFNKDQQSA-FYEILNMPNLNEAQRNGFIQSLKDDPSQSTNV-LGEAKKLNES) of the IgG Fc binding sub-domain of domain D are modified or substituted. In certain aspects amino acid residue Q26, G29, F30, S33, D36, D37, Q40, N43, and/or E47 (SEQ ID NO:2) of the $V_H3$ binding sub-domain of domain D are modified or substituted such that binding to Fc or $V_H3$ is attenuated. In further aspects corresponding modifications or substitutions can be engineered in corresponding positions of the domain A, B, C, and/or E. Corresponding positions are defined by alignment of the domain D amino acid sequence with one or more of the amino acid sequences from other IgG binding domains of SpA. In certain aspects the amino acid substitution can be any of the other 20 amino acids. In a further aspect conservative amino acid substitutions can be specifically excluded from possible amino acid substitutions. In other aspects only non-conservative substitutions are included. In any event, any substitution or combination of substitutions that reduces the binding of the domain such that SpA toxicity is significantly reduced is contemplated. The significance of the reduction in binding refers to a variant that produces minimal to no toxicity when introduced into a subject and can be assessed using in vitro methods described herein.

In certain embodiments, a variant SpA comprises at least or at most 1, 2, 3, 4, 5, 6, 7, 8, 9, 10, or more variant SpA domain D peptides. In certain aspects 1, 2, 3, 4, 5, 6, 7, 8, 9, 10, 11, 12, 13, 14, 15, 16, 17, 18, or 19 or more amino acid residues of the variant SpA are substituted or modified—including but not limited to amino acids F5, Q9, Q10, S11, F13, Y14, L17, N28, I31, and/or K35 (SEQ ID NO:2) of the IgG Fc binding sub-domain of domain D and amino acid residue Q26, G29, F30, S33, D36, D37, Q40, N43, and/or E47 (SEQ ID NO:2) of the $V_H3$ binding sub-domain of domain D. In one aspect glutamine residues at position 9 and/or 10 of SEQ ID NO:2 (or corresponding positions in other domains) are mutated. In another aspect, aspartic acid residues 36 and/or 37 of SEQ ID NO:2 (or corresponding positions in other domains) are mutated. In a further aspect, glutamine 9 and 10, and aspartic acid residues 36 and 37 are mutated. Purified non-toxigenic SpA or SpA-D mutants/variants described herein are no longer able to significantly bind (i.e., demonstrate attenuated or disrupted binding affinity) Fcγ or F(ab)$_2$ $V_H3$ and also do not stimulate B cell apoptosis.

Figure 4:
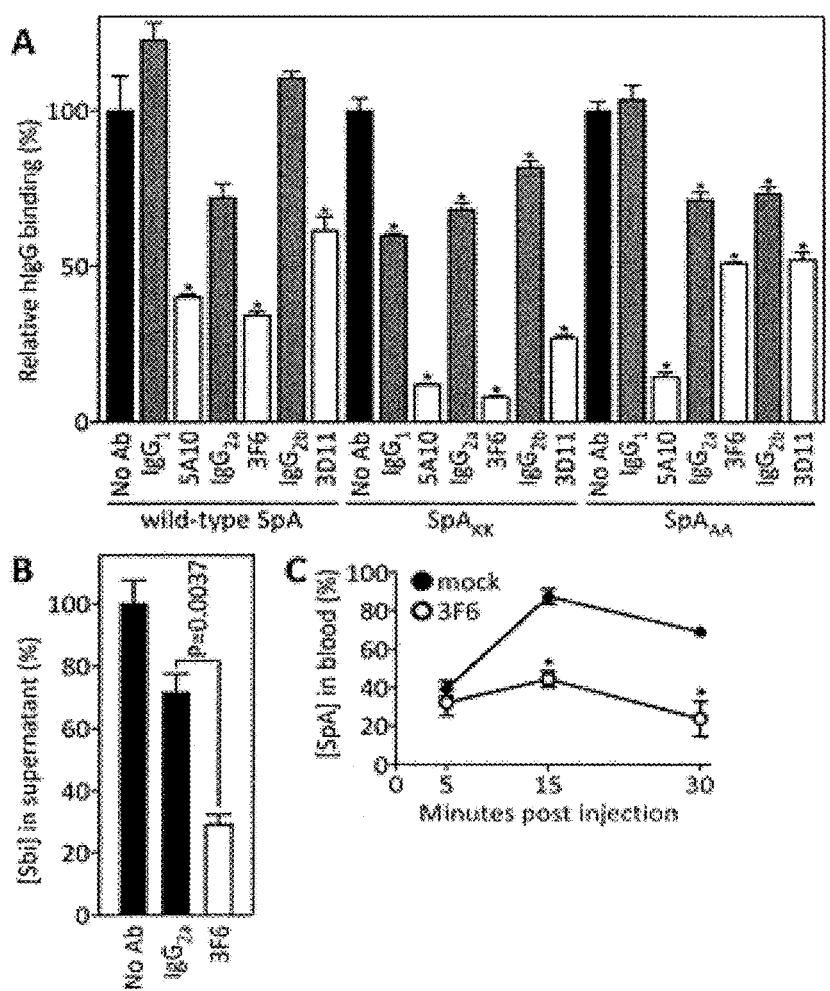
FIGS. 4A-C: $SpA_{KKAA}$-mAbs prevent the association of staphylococcal protein A with immunoglobulin. (A) Isotype control antibodies or $SpA_{KKAA}$-mAbs were used to perturb the binding of human IgG toward proteins (wild-type SpA, or variants that lack the ability to bind Fcγ (SpA$_{KK}$) or Fab (SpA$_{AA}$) immobilized on ELISA plates. The values were normalized to the protein A interaction with human IgG without antibodies (n=4). (B) Staphylococci were grown to mid-log phase and incubated with either isotype control antibody or mAb 3F6 and followed by addition of 2 μg wild-type Sbi$_{1-4}$. Upon incubation, Sbi$_{1-4}$ consumption was measured by immunoblot using affinity purified α-SpA$_{KKAA}$ rabbit antibody. The values were normalized to Sbi$_{1-4}$ sedimentation without antibody (No Ab). (C) Affinity purified SpA (200 μg) was injected into the peritoneal cavity of mice pre-treated with 85 μg (5 mg·kg$^{-1}$) of either isotype control antibody or mAb 3F6. Animals were euthanized at indicated time points to measure the amount of SpA in circulating blood by immunoblot with affinity purified α-SpA$_{KKAA}$ rabbit antibody (n=3 per time point). The values were normalized to the total amount of SpA injected at 0 min. Data are the means and error bars represent ±SEM. Results in A-C are representative of two independent analyses. The asterisks denotes statistical significance (P<0.05).

It is contemplated that cariants of SpA may also include the same variations in domains A, B, C, and/or E as in domain D described above. In some embodiments, a SpA binding polypeptide or antibody may bind to a SpA variant that has a KKAA variation described herein in each of domains A, B, C, D, and E. In further embodiments, that same SpA binding polypeptide or antibody may also bind to a variant that has a GGSS variation instead of the KKAA in every domain. Additionally, in certain embodiments, a SpA binding polypeptide or antibody may bind to a variant Sbi antigen that is altered with respect to one or more of its domains like in SpA. An example of this is shown in FIG. 4.

Moreover, it is contemplated that SpA binding polypeptides or antibodies described herein may be capable of competing with SpA binding for immunoglobulin Fc or Fab region or hinder SpA disruption of immunoglobulin function. Also it is contemplated that SpA binding polypeptides or antibodies described herein may or be capable of perturbing SpA disruption of immunoglobulin function or SpA binding to immunoglobulin Fc or Fab region. In certain embodiments, this property(ies) allows the therapeutic compound to be used to treat infection. Furthermore, methods involve a SpA binding polypeptide or antibody that is capable of neutralizing SpA disruption of immunoglobulin function or SpA binding to immunoglobulin Fc or Fab region.

Non-toxigenic Protein A variants can be used as subunit vaccines and raise humoral immune responses and confer protective immunity against *S. aureus* challenge. Compared to wild-type full-length Protein A or the wild-type SpA-domain D, immunization with SpA-D variants resulted in an increase in Protein A specific antibody. Further SpA variants and methods for using the same are provided in PCT Publication No. WO 2011/005341 and PCT Appln. No. PCT/US11/42845, both incorporated herein by reference.

II. PROTEINACEOUS COMPOSITIONS

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table, below).

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

-continued

Codon Table

| Amino Acids | | | Codons |
|---|---|---|---|
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

It is contemplated that in compositions there is between about 0.001 mg and about 10 mg of total polypeptide, peptide, and/or protein per ml. Thus, the concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an antibody that binds SpA, and may be used in combination with other staphylococcal proteins or protein-binding antibodies described herein.

A. Polypeptides and Polypeptide Production

Embodiments involve polypeptides, peptides, and proteins and immunogenic fragments thereof for use in various aspects described herein. For example, specific antibodies are assayed for or used in neutralizing or inhibiting Staphylococcal infection. In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

In a certain aspects an immunogenic SpA fragment comprises substantially all of the extracellular domain of a protein which has at least 85% identity, at least 90% identity, at least 95% identity, or at least 97-99% identity, including all values and ranges there between, to a sequence selected over the length of the fragment sequence.

Also included in immunogenic compositions are fusion proteins composed of Staphylococcal proteins, or immunogenic fragments of staphylococcal proteins (e.g., SpA). Alternatively, embodiments also include individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, CRM197.

B. Antibodies and Antibody-Like Molecules

In certain aspects, one or more antibodies or antibody-like molecules (e.g., polypeptides comprising antibody CDR domains) may be obtained or produced which have a specificity for an SpA. These antibodies may be used in various diagnostic or therapeutic applications described herein.

As used herein, the term "antibody" is intended to refer broadly to any immunologic binding agent such as IgG, IgM, IgA, IgD and IgE as well as polypeptides comprising antibody CDR domains that retain antigen binding activity. Thus, the term "antibody" is used to refer to any antibody-like molecule that has an antigen binding region, and includes antibody fragments such as Fab', Fab, F(ab')$_2$, single domain antibodies (DABs), Fv, scFv (single chain Fv), and polypeptides with antibody CDRs, scaffolding domains that display the CDRs (e.g., anticalins) or a nanobody. For example, the nanobody can be antigen-specific VHH (e.g., a recombinant VHH) from a camelid IgG2 or IgG3, or a CDR-displaying frame from such camelid Ig. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with embodiments. Minibodies are sFv polypeptide chains which include oligomerization domains at their C-termini, separated from the sFv by a hinge region. Pack et al. (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Alternative scaffolds for antigen binding peptides, such as CDRs are also available and can be used to generate SpA-binding molecules in accordance with the embodiments. Generally, a person skilled in the art knows how to determine the type of protein scaffold on which to graft at least one of the CDRs arising from the original antibody. More particularly, it is known that to be selected such scaffolds must meet the greatest number of criteria as follows (Skerra, 2000): good phylogenetic conservation; known three-dimensional structure (as, for example, by crystallography, NMR spectroscopy or any other technique known to a person skilled in the art); small size; few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra, 2001), protein Z arising from domain B of protein A of *Staphylococcus aureus*, thioredoxin A or proteins with a repeated motif such as the "ankyrin repeat" (Kohl et al., 2003), the "armadillo repeat", the "leucine-rich repeat" and the "tetratricopeptide repeat". For example, anticalins or lipocalin derivatives are a type of binding proteins that have affinities and specificities for various target molecules and can be used as SpA binding molecules. Such proteins are described in US Patent Publication Nos. 20100285564, 20060058510, 20060088908, 20050106660, and PCT Publication No. WO2006/056464, incorporated herein by reference.

Scaffolds derived from toxins such as, for example, toxins from scorpions, insects, plants, mollusks, etc., and the protein inhibitors of neuronal NO synthase (PIN) may also be used in certain aspects.

Monoclonal antibodies (MAbs) are recognized to have certain advantages, e.g., reproducibility and large-scale production. Embodiments include monoclonal antibodies of the human, murine, monkey, rat, hamster, rabbit and chicken origin.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin. In order to describe antibodies of some embodiments, the strength with which an antibody molecule binds an epitope, known as affinity, can be measured. The affinity of an antibody may be determined by measuring an association constant ($K_a$) or dissociation constant ($K_d$). Antibodies deemed useful in certain embodiments may have an association constant of about, at least about, or at most about $10^6$, $10^7$, $10^8$, $10^9$ or $10^{10}$ M or any range derivable therein. Similarly, in some embodiments antibodies may have a dissociation constant of about, at least about or at most about $10^{-6}$, $10^{-7}$, $10^{-8}$, $10^{-9}$ or $10^{-10}$. M or any range derivable therein. These values are reported for antibodies discussed herein and the same assay may be used to evaluate the binding properties of such antibodies In certain embodiments, a polypeptide that specifically binds to SpA is able to neutralize protein A and/or promote opsonophagocytic killing of staphylococci. Moreover, in some embodiments, the polypeptide that is used can provided protective immunity against *S. aureus* disease. It is contemplated that mAb 358A76.1 is excluded from these embodiments.

1. Methods for Generating Antibodies

Methods for generating antibodies (e.g., monoclonal antibodies and/or monoclonal antibodies) are known in the art. Briefly, a polyclonal antibody is prepared by immunizing an animal with a SpA polypeptide (e.g., a non-toxogenic SpA) or a portion thereof in accordance with embodiments and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include any acceptable immunostimulatory compound, such as cytokines, chemokines, cofactors, toxins, plasmodia, synthetic compositions or vectors encoding such adjuvants.

Adjuvants that may be used in accordance with embodiments include, but are not limited to, IL-1, IL-2, IL-4, IL-7, IL-12, -interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MEW antigens may even be used. Exemplary adjuvants may include complete Freund's adjuvant (a non-specific stimulator of the immune response containing killed *Mycobacterium tuberculosis*), incomplete Freund's adjuvants and/or aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, NJ), cytokines such as -interferon, IL-2, or IL-12 or genes encoding proteins involved in immune helper functions, such as B-7.

The amount of immunogen composition used in the production of antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography, among others.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. In some embodiments, Rodents such as mice and rats are used in generating monoclonal antibodies. In some embodiments, rabbit, sheep or frog cells are used in generating monoclonal antibodies.

The use of rats is well known and may provide certain advantages (Goding, 1986, pp. 60 61). Mice (e.g., BALB/c mice) are routinely used and generally give a high percentage of stable fusions.

The animals are injected with antigen, generally as described above. The antigen may be mixed with adjuvant, such as Freund's complete or incomplete adjuvant. Booster administrations with the same antigen or DNA encoding the antigen may occur at approximately two-week intervals. As discussed in the Examples, the antigen may be altered compared to an antigen sequence found in nature. In some embodiments, a variant or altered Protein A peptide or polypeptide is employed to generate antibodies. In certain embodiments, the SpA variant has 1, 2, 3, 4, 5, 6, 7, or 8 changes in 1, 2, 3, 4, or all 5 of the A, B, C, D, or E domains of SpA.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Generally, spleen cells are a rich source of antibody-producing cells that are in the dividing plasmablast stage. Typically, peripheral blood cells may be readily obtained, as peripheral blood is easily accessible.

In some embodiments, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). cites). For example, where the immunized animal is a mouse, one may use P3 X63/Ag8, X63 Ag8.653, NS1/1.Ag 4 1, Sp210 Ag14, FO, NSO/U, MPC 11, MPC11 X45 GTG 1.7 and S194/5XX0 Bul; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al. (2002), for a discussion of myeloma expression systems.

One murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71 74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

A selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies can be obtained from the monoclonal antibodies so produced by methods which include digestion with enzymes, such as pepsin or papain, and/or by cleavage of disulfide bonds by chemical reduction. Alternatively, monoclonal antibody fragments can be synthesized using an automated peptide synthesizer.

It is also contemplated that a molecular cloning approach may be used to generate monoclonal antibodies. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination which further increases the chance of finding appropriate antibodies.

Another embodiment concerns producing antibodies, for example, as is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments can be synthesized using an automated peptide synthesizer, or by expression of full-length gene or of gene fragments in *E. coli*.

It is further contemplated that monoclonal antibodies may be further screened or optimized for properties relating to specificity, avidity, half-life, immunogenicity, binding association, binding disassociation, or overall functional properties relative to being a treatment for infection. Thus, it is contemplated that monoclonal antibodies may have 1, 2, 3, 4, 5, 6, or more alterations in the amino acid sequence of 1, 2, 3, 4, 5, or 6 CDRs of monoclonal antibodies 5A10, 8E2, 3A6, 3F6, 1F10, 6D11, 3D11, 5A11, 1B10 or 4C1. It is contemplated that the amino acid in position 1, 2, 3, 4, 5, 6, 7, 8, 9, or 10 of CDR1, CDR2, CDR3, CDR4, CDR5, or CDR6 of the VJ or VDJ region of the light or heavy variable region of monoclonal antibodies 5A10, 8E2, 3A6, 3F6, 1F10, 6D11, 3D11, 5A11, 1B10 or 4C1 may have an insertion, deletion, or substitution with a conserved or non-conserved amino acid. Such amino acids that can either be substituted or constitute the substitution are disclosed above.

In some embodiments, fragments of a whole antibody can perform the function of binding antigens. Examples of binding fragments are (i) the Fab fragment constituted with the VL, VH, CL and CH1 domains; (ii) the Fd fragment consisting of the VH and CH1 domains; (iii) the Fv fragment constituted with the VL and VH domains of a single antibody; (iv) the dAb fragment (Ward, 1989; McCafferty et al., 1990; Holt et al., 2003), which is constituted with a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988; Huston et al., 1988); (viii) bispecific single chain Fv dimers (PCT/US92/09965) and (ix) "diabodies", multivalent or multispecific fragments constructed by gene fusion (WO94/13804; Holliger et al., 1993). Fv, scFv or diabody molecules may be stabilized by the incorporation of disulphide bridges linking the VH and VL domains (Reiter et al., 1996). Minibodies comprising a scFv joined to a CH3 domain may also be made (Hu et al. 1996). The citations in this paragraph are all incorporated by reference.

Antibodies also include bispecific antibodies. Bispecific or bifunctional antibodies form a second generation of monoclonal antibodies in which two different variable regions are combined in the same molecule (Holliger, P. & Winter, G. 1999 Cancer and metastasis rev. 18:411-419, 1999). Their use has been demonstrated both in the diagnostic field and in the therapy field from their capacity to recruit new effector functions or to target several molecules on the surface of tumor cells. Where bispecific antibodies are to be used, these may be conventional bispecific antibodies, which can be manufactured in a variety of ways (Holliger et al, PNAS USA 90:6444-6448, 1993), e.g. prepared chemically or from hybrid hybridomas, or may be any of the bispecific antibody fragments mentioned above. These antibodies can be obtained by chemical methods (Glennie et al., 1987 J. Immunol. 139, 2367-2375; Repp et al., J. Hemat. 377-382, 1995) or somatic methods (Staerz U. D. and Bevan M. J. PNAS 83, 1986; et al., Method Enzymol. 121:210-228, 1986) but likewise by genetic engineering techniques which allow the heterodimerization to be forced and thus facilitate the process of purification of the antibody sought (Merchand et al. Nature Biotech, 16:677-681, 1998). Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction. The citations in this paragraph are all incorporated by reference.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against SpA, then a library can be made where the other arm is varied and an antibody of appropriate specificity selected. Bispecific whole antibodies may be made by alternative engineering methods as described in Ridgeway et al, (Protein Eng., 9:616-621, 1996), which is hereby incorporated by reference.

C. Antibody and Polypeptide Conjugates

Embodiments provide antibodies and antibody-like molecules against SpA proteins, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, therapeutic enzymes, antibiotics, radio-labeled nucleotides and the like. By contrast, a reporter molecule is defined as any moiety which may be detected using an assay. Non-limiting examples of reporter molecules which have been conjugated to antibodies include enzymes, radiolabel s, haptens, fluorescent labels, phosphorescent molecules, chemiluminescent molecules, chromophores, luminescent molecules, photoaffinity molecules, colored particles or ligands, such as biotin.

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. A Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging". Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might use astatine$^{211}$, carbon$^{14}$, chromium$^{51}$, chlorine$^{36}$, cobalt$^{57}$, cobalt$^{58}$, copper$^{67}$, Eu$^{152}$, gallium$^{67}$, hydroge$^{3}$n, iodine$^{123}$, iodine$^{125}$, iodine$^{131}$, indium$^{111}$, iron$^{59}$, phosphorus$^{32}$, rhenium$^{186}$, rhenium$^{188}$, selenium$^{75}$, sulphu$^{35}$r, technicium$^{99m}$ and/or yttrium$^{90}$. $^{125}$I is often used in certain embodiments, and technicium$^{99m}$ and/or indium$^{111}$ are also often used due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetraacetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Antibody conjugates include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In some embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In some embodiments, anti-SpA antibodies are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays include, but are not limited to, those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

III. NUCLEIC ACIDS

In certain embodiments, there are recombinant polynucleotides encoding the proteins, polypeptides, or peptides described herein. Polynucleotide sequences contemplated include those encoding antibodies to SpA or SpA binding portions thereof.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptide (e.g., an antibody or fragment thereof) that binds to SpA. The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain embodiments, there are polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence provided herein using the methods described herein (e.g., BLAST analysis using standard parameters). In certain aspects, the isolated polynucleotide will comprise a nucleotide sequence encoding a polypeptide that has at least 90%, preferably 95% and above, identity to an amino acid sequence described herein, over the entire length of the sequence; or a nucleotide sequence complementary to said isolated polynucleotide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody that binds SpA.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

The particular promoter that is employed to control the expression of a peptide or protein encoding polynucleotide is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

In expression, particularly eukaryotic expression, one will typically include a polyadenylation signal to effect proper polyadenylation of the transcript.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with an embodiment to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

D. Methods of Gene Transfer

Suitable methods for nucleic acid delivery to effect expression of compositions are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945, 100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985). Through the application of techniques such as these, organelle(s), cell(s), tissue(s) or organism(s) may be stably or transiently transformed.

IV. METHODS OF TREATMENT

As discussed above, the compositions and methods of using these compositions can treat a subject (e.g., limiting bacterial load or abscess formation or persistence) having, suspected of having, or at risk of developing an infection or related disease, particularly those related to staphylococci. One use of the compositions is to prevent nosocomial infections by inoculating a subject prior to hospital treatment.

As used herein the phrase "immune response" or its equivalent "immunological response" refers to a humoral (antibody mediated), cellular (mediated by antigen-specific T cells or their secretion products) or both humoral and cellular response directed against a protein, peptide, or polypeptide of the invention in a recipient patient. Treatment or therapy can be an active immune response induced by administration of immunogen or a passive therapy effected by administration of antibody, antibody containing material, or primed T-cells.

As used herein "passive immunity" refers to any immunity conferred upon a subject by administration of immune effectors including cellular mediators or protein mediators (e.g., an polypeptide that binds to SpA protein). An antibody composition may be used in passive immunization for the prevention or treatment of infection by organisms that carry the antigen recognized by the antibody. An antibody composition may include antibodies or polypeptides comprising antibody CDR domains that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the patient immunoglobulins (Ig) or fragments thereof and/or other immune factors obtained from a donor or other non-patient source having a known immunoreactivity. In other aspects, an antigenic composition can be administered to a subject who then acts as a source or donor for globulin, produced in response to challenge from the composition ("hyperimmune globulin"), that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat *staphylococcus* infection. Hyperimmune globulins are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512, 282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include those methods described in Epitope Mapping Protocols (1996). T cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject. As used herein and in the claims, the terms "antibody" or "immunoglobulin" are used interchangeably.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

In one embodiment a method includes treatment for a disease or condition caused by a *staphylococcus* pathogen. In certain aspects embodiments include methods of treatment of staphylococcal infection, such as hospital acquired nosocomial infections. In some embodiments, the treatment is administered in the presence of staphylococcal antigens. Furthermore, in some examples, treatment comprises administration of other agents commonly used against bacterial infection, such as one or more antibiotics.

The therapeutic compositions are administered in a manner compatible with the dosage formulation, and in such amount as will be therapeutically effective. The quantity to be administered depends on the subject to be treated. Precise amounts of active ingredient required to be administered depend on the judgment of the practitioner. Suitable regimes for initial administration and boosters are also variable, but are typified by an initial administration followed by subsequent administrations.

The manner of application may be varied widely. Any of the conventional methods for administration of a polypeptide therapeutic are applicable. These are believed to include oral application on a solid physiologically acceptable base or in a physiologically acceptable dispersion, parenterally, by injection and the like. The dosage of the composition will depend on the route of administration and will vary according to the size and health of the subject.

In certain instances, it will be desirable to have multiple administrations of the composition, e.g., 2, 3, 4, 5, 6 or more administrations. The administrations can be at 1, 2, 3, 4, 5, 6, 7, 8, to 5, 6, 7, 8, 9, 10, 11, 12 twelve week intervals, including all ranges there between.

A. Antibodies and Passive Immunization

Certain aspects are directed to methods of preparing an antibody for use in prevention or treatment of staphylococcal infection comprising the steps of immunizing a recipient with a vaccine and isolating antibody from the recipient, or producing a recombinant antibody. An antibody prepared by these methods and used to treat or prevent a staphylococcal infection is a further aspect. A pharmaceutical composition comprising antibodies that specifically bind SpA and a pharmaceutically acceptable carrier is a further aspect that could be used in the manufacture of a medicament for the treatment or prevention of staphylococcal disease. A method for treatment or prevention of staphylococcal infection comprising a step of administering to a patient an effective amount of the pharmaceutical preparation is a further aspect.

Inocula for polyclonal antibody production are typically prepared by dispersing the antigenic composition (e.g., a peptide or antigen or epitope of SpA or a consensus thereof) in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies. The antibodies can be isolated to the extent desired by well known techniques such as affinity chromatography (Harlow and Lane, *Antibodies: A Laboratory Manual* 1988). Antibodies can include antiserum preparations from a variety of commonly used animals e.g., goats, primates, donkeys, swine, horses, guinea pigs, rats or man. The animals are bled and serum recovered.

An antibody can include whole antibodies, antibody fragments or subfragments. Antibodies can be whole immunoglobulins of any class (e.g., IgG, IgM, IgA, IgD or IgE), chimeric antibodies, human antibodies, humanized antibodies, or hybrid antibodies with dual specificity to two or more antigens. They may also be fragments (e.g., F(ab')2, Fab', Fab, Fv and the like including hybrid fragments). An antibody also includes natural, synthetic or genetically engineered proteins that act like an antibody by binding to specific antigens with a sufficient affinity.

A vaccine can be administered to a recipient who then acts as a source of antibodies, produced in response to challenge from the specific vaccine. A subject thus treated would donate plasma from which antibody would be obtained via conventional plasma fractionation methodology. The isolated antibody would be administered to the same or different subject in order to impart resistance against or treat staphylococcal infection. Antibodies are particularly useful for treatment or prevention of staphylococcal disease in infants, immune compromised individuals or where treatment is required and there is no time for the individual to produce a response to vaccination.

An additional aspect is a pharmaceutical composition comprising two of more antibodies or monoclonal antibodies (or fragments thereof; preferably human or humanized) reactive against at least two constituents of the immunogenic composition, which could be used to treat or prevent infection by Gram positive bacteria, preferably staphylococci, more preferably *S. aureus* or *S. epidermidis*.

B. Combination Therapy

The compositions and related methods, particularly administration of an antibody that binds SpA or a peptide or consensus peptide thereof to a patient/subject, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a therapy is used in conjunction with antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Various combinations of therapy may be employed, for example antibiotic therapy is "A" and an antibody therapy that comprises an antibody that binds SpA or a peptide or consensus peptide thereof is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the antibody compositions to a patient/subject will follow general protocols for the administration of such compounds, taking into account the toxicity, if any, of the composition. It is expected that the treatment cycles would be repeated as necessary. It is also contemplated that various standard therapies, such as hydration, may be applied in combination with the described therapy.

C. General Pharmaceutical Compositions

In some embodiments, pharmaceutical compositions are administered to a subject. Different aspects may involve administering an effective amount of a composition to a subject. In some embodiments, an antibody that binds SpA or a peptide or consensus peptide thereof may be administered to the patient to protect against or treat infection by one or more bacteria from the *Staphylococcus* genus. Alternatively, an expression vector encoding one or more such antibodies or polypeptides or peptides may be given to a patient as a preventative treatment. Additionally, such compositions can be administered in combination with an antibiotic. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-infective agents and vaccines, can also be incorporated into the compositions.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization or an equivalent procedure. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective.

The formulations are easily administered in a variety of dosage forms, such as the type of injectable solutions described above.

V. EXAMPLES

The following examples are given for the purpose of illustrating various embodiments and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Monoclonal Antibodies to *Staphylococcus Aureus* Protein A

SpA$_{KKAA}$-mAbs Protect Mice Against Staphylococcal Disease.

BALB/c mice were immunized with purified SpA$_{KKAA}$ using a prime-booster regimen and antigen specific IgG responses were quantified by ELISA. Animals were euthanized and their splenocytes fused with myeloma cells. The resulting hybridomas were screened for the production of antigen-specific mAbs. Initially, protein A-specific mAbs were screened using the functional assays as well as the murine infection model (Table 1). After the initial screen, we selected three mAbs (5A10, 3F6, and 3D11) for further characterization as these antibodies displayed the best immune protection in each isotype group (Table 1). BALB/c Mice were immunized with affinity purified mAbs (5 mg·kg$^{-1}$ body weight) and challenged by injecting 1×10$^7$ CFU *S. aureus* Newman, a methicillin-sensitive clinical isolate (MSSA) (Baba et al., 2007), into the periorbital venous sinus of the right eye. The ability of staphylococci to seed abscesses in renal tissues was examined by histopathology four days after challenge (Table 1). In homogenized renal tissues of control mice (immunized with 5 mg·kg$^{-1}$ isotype control mAbs), an average staphylococcal load of 5.02 log$_{10}$ CFU·g$^{-1}$ (IgG$_1$), 4.64 log$_{10}$ CFU·g$^{-1}$ (IgG$_{2a}$) and 5.24 log$_{10}$ CFU·g$^{-1}$ (IgG$_{2b}$) was recovered (Table 1). Compared to isotype mAb-treated controls, animals that received protein A specific mAbs displayed a reduction in staphylococcal load [2.80 log$_{10}$ CFU·g$^{-1}$ (5A10), 2.28 log$_{10}$ CFU·g$^{-1}$ (3F6), and 2.72 log$_{10}$ CFU·g$^{-1}$ (3D11)] as well as abscess formation (Table 1). Of note, not all SpA$_{KKAA}$-mAbs generated protection against staphylococcal disease (Table 1) even though these antibodies bound with appreciable affinity to their antigen (see for example 3A6 and 6D11 in Table 3).

TABLE 1

Passive immunization of mice with monoclonal antibodies against SpA$_{KKAA}$

Staphylococcal load and abscess formation in renal tissue

| [a]Antibody | [b]log$_{10}$CFU g$^{-1}$ | [c]P value | [d]Reduction | [e]Number of abscesses | [c]P value |
|---|---|---|---|---|---|
| IgG$_1$ | | | | | |
| Mock | 5.02 ± 0.66 | — | — | 2.00 ± 0.94 | — |
| 5A10 | 2.22 ± 0.22 | 0.0019 | 2.80 | 0.00 ± 0.00 | 0.0350 |
| 8E2 | 3.01 ± 0.37 | 0.0629 | 2.01 | 0.20 ± 0.20 | 0.1117 |
| 3A6 | 3.98 ± 0.47 | 0.3068 | 1.04 | 0.50 ± 0.50 | 0.1497 |
| 7E2 | 5.01 ± 0.64 | 0.9396 | 0.01 | 2.00 ± 0.99 | 0.7461 |
| IgG$_{2a}$ | | | | | |
| Mock | 4.64 ± 0.49 | — | — | 3.70 ± 1.40 | — |
| 3F6 | 2.36 ± 0.36 | 0.0010 | 2.28 | 0.60 ± 0.50 | 0.0239 |
| 1F10 | 3.05 ± 0.46 | 0.0299 | 1.59 | 0.70 ± 0.40 | 0.0812 |
| 6D11 | 3.88 ± 0.75 | 0.1967 | 0.76 | 0.90 ± 0.35 | 0.1793 |
| IgG$_{2b}$ | | | | | |
| Mock | 5.24 ± 0.51 | — | — | 3.00 ± 0.67 | — |
| 3D11 | 2.52 ± 0.40 | 0.0010 | 2.72 | 0.56 ± 0.28 | 0.0068 |
| 5A11 | 3.26 ± 0.55 | 0.0171 | 1.98 | 0.80 ± 0.55 | 0.0286 |
| 1B10 | 3.31 ± 0.34 | 0.0113 | 1.93 | 0.50 ± 0.50 | 0.0070 |
| 4C1 | 3.38 ± 0.50 | 0.0228 | 1.86 | 0.10 ± 0.10 | 0.0016 |
| 2F2 | 3.49 ± 0.70 | 0.0232 | 1.75 | 0.40 ± 0.27 | 0.0424 |
| 8D4 | 3.83 ± 0.63 | 0.1198 | 1.41 | 0.80 ± 0.51 | 0.0283 |
| 7D11 | 4.23 ± 0.55 | 0.2729 | 1.01 | 0.90 ± 0.55 | 0.0424 |
| 2C3 | 4.24 ± 0.61 | 0.1733 | 1.00 | 1.40 ± 0.60 | 0.1623 |
| 4C5 | 4.35 ± 0.53 | 0.2410 | 0.89 | 1.90 ± 0.84 | 0.3270 |
| 6B2 | 4.42 ± 0.62 | 0.4055 | 0.82 | 2.20 ± 1.00 | 0.3553 |
| 4D5 | 4.96 ± 0.58 | 0.7912 | 0.28 | 3.80 ± 1.26 | 0.7884 |
| 2B8 | 5.00 ± 0.66 | 0.8534 | 0.24 | 4.60 ± 2.89 | 0.6184 |
| 1H7 | 5.59 ± 0.43 | 0.5675 | −0.35 | 2.89 ± 0.73 | 0.9008 |

[a]Affinity purified antibodies were injected into the peritoneal cavity of BALB/c mice at a concentration of 5 mg kg$^{-1}$ four hours prior to intravenous challenge with 1 × 10$^7$ CPU *S. aureus* Newman.
[b]Means (±SEM) of staphylococcal load calculated as log$_{10}$ CFU g$^{-1}$ in homogenized renal tissues 4 days following infection in cohorts often BALB/c mice per immunization. A representative of three independent and reproducible animal experiments is shown.
[c]Statistical significance was calculated with the unpaired two-tailed Mann-Whitney test and P-values recorded.
[d]Reduction in bacterial load calculated as log$_{10}$ CFU g$^{-1}$.
[e]Histopathology of hematoxylin-eosin stained, thin sectioned kidneys from ten animals; the number of abscesses per kidney was recorded and averaged for the final mean (±SEM).

SpA$_{KKAA}$-mAbs Protect Mice Against MRSA Challenge.

Cohorts of BALB/c mice were immunized with mAbs 5A10, 3F6, 3D11 (5 mg·kg$^{-1}$) or a combination of all three mAbs (15 mg·kg$^{-1}$) and challenged with strain MW2, a highly virulent community-acquired, MRSA isolate (Baba et al., 2002). Compared to isotype mAb-treated controls, animals that received any one of the three mAbs (5A10, 3F6, 3D11) harbored a reduced bacterial load and fewer staphylococcal abscesses in renal tissues (Table 2). Animals that had been immunized with a mixture of all three mAbs (15 mg·kg$^{-1}$) displayed an even greater reduction in staphylococcal load (2.03 log$_{10}$ CFU·g$^{-1}$ reduction; P<0.0002) and in abscess formation (vaccine vs. mock, P<0.0004). It is likely that enhanced protection is due to administration of increased concentration of mAbs (15 mg·kg$^{-1}$ vs. 5 mg·kg$^{-1}$). We arrived at this hypothesis because the three antibodies, although recognizing similar structural features, do not appear to occupy identical binding sites on SpA (vide infra). Further, increasing the concentration of only one of the three mAbs (3F6) caused the same effect: increased protection against staphylococcal disease (vide infra).

In addition to providing immediate protection against staphylococcal challenge, SpA$_{KKAA}$-specific mAbs may also neutralize the B-cell superantigen activity of SpA (Goodyear and Silverman, 2003), thereby enabling infected hosts to generate antibody responses against many different staphylococcal antigens (Kim et al., 2010a). To examine this possibility, BALB/c mice were passively immunized with mAb 3F6 or its IgG$_{2a}$ isotype control (20 mg·kg$^{-1}$) prior to intravenous challenge with S. aureus MW2. Fifteen days after challenge, animals were euthanized and staphylococcal load in organ tissue examined (FIG. 1A). Mice that had been immunized with mAb 3F6 harbored a reduced staphylococcal load (4.77 log$_{10}$ CFU·g$^{-1}$ reduction, P=0.0013) as well as a reduced number of abscesses [from 10.14 (±2.08) (IgG$_{2a}$) to 3.00 (±1.00) (3F6), P=0.0065; FIG. 1A]. Blood samples withdrawn 15 days post-challenge were examined for serum IgG reactive against fourteen staphylococcal antigens under consideration as protective antigens for vaccine development: Coa, ClfA, ClfB, EsxA, EsxB, FnBPA, FnBPB, Hla, IsdA, IsdB, LukD, SdrD, SpA$_{KKAA}$ and vWbp (DeDent et al., 2012). As observed previously with animals that had been actively vaccinated with SpA$_{KKAA}$, mice that had been immunized with mAb 3F6 developed higher serum IgG titers against several different staphylococcal antigens (FIG. 1B) (Kim et al., 2010a). In particular, IgG levels against Coa, ClfA, EsxA, EsxB, FnBPB, Hla, IsdA, LukD, SdrD and vWbp were increased in serum samples of mAb 3F6-immunized animals as compared to the control cohort. Nevertheless, serum IgG against IsdB, the staphylococcal hemoglobin hemophore (Mazmanian et al., 2003), was not increased (FIG. 1B). The IgG titer against SpA$_{KKAA}$ was sustained over fifteen days following passive transfer of mAb 3F6 (FIG. 1B).

Figure 6:
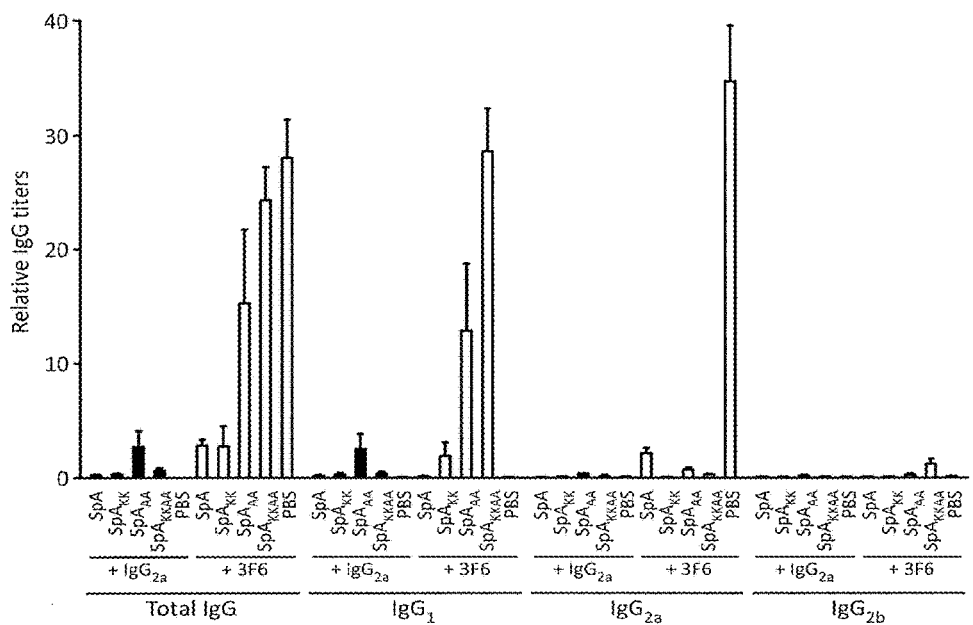
FIG. 6: Generation of protein A specific immune response by mAb 3F6. Protein A-specific antibody titers in animals (n=5 per group) that had received a mixture of 20 μg of protein A variants (SpA, SpA$_{KK}$, SpA$_{AA}$, SpA$_{KKAA}$, and PBS) and 85 μg of mAb 3F6 (an IgG2a antibody) or its isotype control were measured by ELISA. Immune titers were normalized to their isotype control standards. Data are the means and error bars represent ±SEM. Results are representative of two independent analyses.

During staphylococcal infection, recognition of soluble SpA by mAb 3F6 is expected to form immune complexes (IC) that are then phagocytosed by immune cells. Phagocytosed SpA is then processed by proteolytic enzymes in the phagolysosome and peptide fragments are presented to T and B cells to produce polyclonal antibodies. As a confirmatory test, cohorts of animals received a mixture of affinity purified recombinant protein A variants [SpA, SpA$_{KK}$, SpA$_{AA}$, SpA$_{KKAA}$, and mock (PBS)] in the presence of mAb 3F6 or its isotype control at day 0 and 11. At day 21, animals were euthanized and their ability to elicit different classes of SpA-specific antibody was measured by ELISA. All animals failed to generate SpA-specific antibody responses without mAb treatment (FIG. 6). In addition, animals that received B cell superantigens (SpA and SpA$_{KK}$; vide infra) failed to generate SpA-specific IgG$_1$ and IgG$_{2a}$ antibodies even in the presence of mAb 3F6 (FIG. 6). However, mice treated with SpA variants lacking B cell superantigen activity (SpA$_{AA}$ and SpA$_{KKAA}$; vide infra) were able to generate a significant amount of IgG$_1$ (FIG. 6). Although the estimated amount of soluble protein A during infection (5-10 ng per 10$^7$ CFU) is well below the dose of affinity purified protein A injected in these experiments into animals, the data in FIG. 6 suggest a potential role of SpA-specific TB cells in neutralizing B cell superantigen activity. Taken together, the inventors presume that active vaccination with SpA$_{KKAA}$ (Kim et al., 2010a), but not passive immunization of S. aureus infected mice with neutralizing mAbs (vide infra) can raise a significant level of protein A-specific antibodies.

TABLE 2

Immunization with SpA$_{KKAA}$-mAbs protects mice against MRSA challenge

| | Staphylococcal load and abscess formation in renal tissue | | | | |
|---|---|---|---|---|---|
| [a]Antibody | [b]log$_{10}$CFU g$^{-1}$ | [c]P value | Reduction | [e]Number of abscesses | [c]P value |
| IgG$_1$ | | | | | |
| Mock | 7.42 ± 0.20 | — | — | 22.3 ± 6.3 | — |
| 5A10 | 6.00 ± 0.21 | 0.0009 | 1.42 | 10.2 ± 2.5 | 0.0482 |
| IgG$_{2a}$ | | | | | |
| Mock | 7.15 ± 0.18 | — | — | 11.8 ± 2.0 | — |
| 3F6 | 5.80 ± 0.21 | 0.0009 | 1.35 | 6.4 ± 0.7 | 0.0323 |
| IgG$_{2b}$ | | | | | |
| Mock | 7.13 ± 0.11 | — | — | 14.0 ± 1.8 | — |
| 3D11 | 5.81 ± 0.25 | 0.0006 | 1.32 | 7.7 ± 1.9 | 0.0489 |
| IgG$_1$ + IgG$_{2a}$ + IgG$_{2b}$ | | | | | |
| Mock | 7.75 ± 0.06 | — | — | 17.4 ± 1.7 | — |
| 5A10/3F6/3D11 | 5.72 ± 0.12 | 0.0002 | 2.03 | 6.7 ± 0.6 | 0.0004 |

[a]Affinity purified antibodies were injected into the peritoneal cavity of BALB/c mice at a concentration of individual antibody at 5 mg · kg$^{-1}$ or combinations of three monoclonal antibodies at 15 mg · kg$^{-1}$ twenty four hours prior to intravenous challenge with 1 × 10$^7$ CFU S. aureus MW2.
[b]Means (±SEM) of staphylococcal load calculated as log$_{10}$CFU · g$^{-1}$ in homogenized renal tissues 4 days following infection in cohorts of ten BALB/c mice per immunization with limit of detection at 1.99 log$_{10}$CFU · g$^{-1}$. A representative of two independent and reproducible animal experiments is shown.
[c]Statistical significance was calculated with the two-tailed Mann-Whitney test and P-values recorded.
[d]Reduction in bacterial load calculated as log$_{10}$CFU · g$^{-1}$.
[e]Histopathology of hematoxylin-eosin stained, thin sectioned kidneys from ten animals; the number of abscesses per kidney was recorded and averaged for the final mean (±SEM).

mAb Spa27 does not Recognize SpA$_{KKAA}$ and Fails to Elicit Protective Immunity in Mice.

Figure 7:
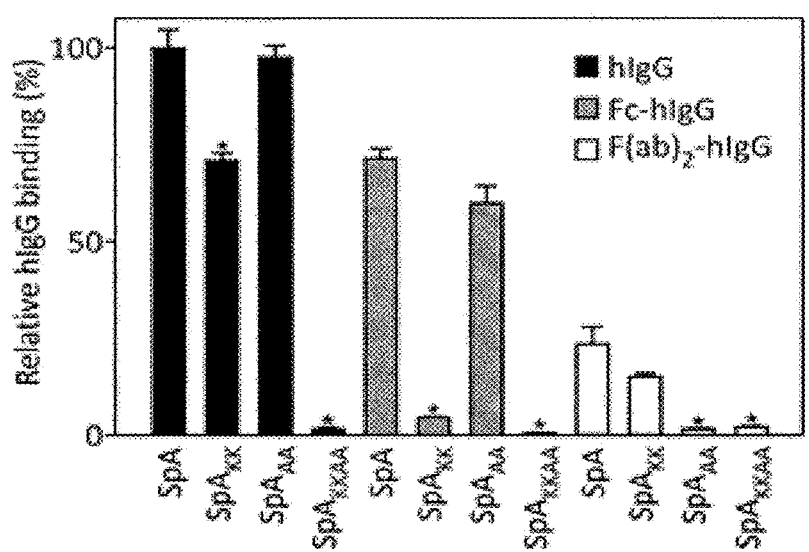
FIG. 7: Interaction of human immunoglobulin fragments with protein A variants. Association of immobilized protein A variants (wild-type SpA, SpA$_{KK}$, SpA$_{AA}$ or SpA$_{KKAA}$) with human immunoglobulin (hIgG), as well as its Fc or F(ab)$_2$ fragments were analyzed by ELISA and normalized to the interaction of SpA and human IgG. Statistical significance of SpA variants were compared against SpA binding to each ligand (human IgG, Fc or F(ab)$_2$ fragments, n=4). Data are the means and error bars represent ±SEM. Results are representative of three independent analyses. The asterisks denotes statistical significance (P<0.05).

Spa27 is a commercially available protein A-specific monoclonal antibody (Sigma) that has been used over the past two decades for the detection of staphylococcal protein A (Perry et al., 2002). The Spa27 hybridoma was generated from mice that had been immunized with wild-type staphylococcal protein A purified from S. aureus strain Cowan I (Sjoquist et al., 1972). Previous work demonstrated that wild-type protein A triggers the clonal expansion and collapse of B cell populations (Forsgren et al., 1976, Goodyear et al., 2003), thereby ablating protein A-specific immune response in mice (Goodyear et al., 2004), and that wild-type protein A encompasses binding sites for both Fcγ and Fab V$_H$3 (Graille et al., 2000, Stahlenheim et al., 1970). We therefore wondered whether Spa27 recognizes wild-type protein A as an antigen. To address this question, we used ELISA with purified recombinant protein A (SpA) or its variants that lack either the ability to specifically bind Fcγ (SpA$_{KK}$), the Fab domain of V$_H$3 (SpA$_{AA}$) or both (SpA$_{KKAA}$) (FIG. 7). The data revealed strong binding of Spa27 to wild-type SpA and SpA$_{KK}$, but not to SpA$_{AA}$ or SpA$_{KKAA}$ (FIG. 9B). Spa27 is a mouse IgG$_1$ isotype antibody, which explains its inability to bind protein A via Fcγ (Kronvall et al., 1970). The weak association between Spa27 and SpA$_{AA}$ or SpA$_{KKAA}$ could be due to the seemingly remote possibility that SpA27 requires residues D36/D37 in each of the five IgBDs for antigen recognition or, more likely to us, that Spa27 binds SpA via its Fab domain, assuming the antibody belongs to the V$_H$3 or a related class of antibody.

We examined the biological function of Spa27 by injecting for pairwise comparison mAbs 3F6 or Spa27 (5 mg·kg$^{-1}$) into the peritoneal cavity of BALB/c mice. These animals were then challenged with *S. aureus* USA300 (LAC), the highly virulent community-acquired MRSA strain epidemic in the United States (Diep et al., 2006). At 4 days post challenge, animals were euthanized and the bacterial load in the kidneys of infected animals were determined (FIG. 9B). Compared to mock (PBS) treatment, animals that received mAb 3F6 harbored a reduced bacterial load (1.38 log$_{10}$ CFU·g$^{-1}$ reduction, P=0.0011). In contrast to the protective immunity elicited by 3F6, mAb Spa27 failed to reduce the bacterial load in kidneys of infected animals (0.20 log$_{10}$ CFU·g$^{-1}$ reduction, P=0.2111). These data reveal that mAb Spa27 does not provide protection against staphylococcal disease. Further, the experiments with Spa27 illustrate that immunization of mice with wild-type protein A may not elicit monoclonal antibodies that can neutralize the immune-modulatory attributes of protein A by binding this molecule as an antigen.

Recognition of SpA$_{KKAA}$ by mAbs.

Microtiter dishes were coated with SpA$_{KKAA}$ and ELISA was used to determine the affinity constant (K$_a$=[mAb·Ag]/[mAb]×[Ag]) of purified mAbs. mAb 3F6 displayed the highest affinity (K$_a$ 22.97×10$^9$ M$^{-1}$) followed by mAb 5A10 (K$_a$ 8.47×10$^9$ M$^{-1}$) and mAb 3D11 (K$_a$ 3.93×10$^9$ M$^{-1}$, Table 3). Each of the five IgBDs alone (E$_{KKAA}$, D$_{KKAA}$, A$_{KKAA}$, B$_{KKAA}$ and C$_{KKAA}$) or peptides encompassing helix 1, 2 or 3 as well as helices 1+2 and 2+3 of the IgBD E$_{KKAA}$ domain were examined for antibody binding (Table 3). mAbs 5A10 and 3F6 bound all five IgBDs with the same affinity as SpA$_{KKAA}$. mAb 5A10 did not bind to the helical peptides, whereas mAb 3F6 displayed weak affinity for the helix 1+2 peptide. mAb 3D11 bound to B$_{KKAA}$ and C$_{KKAA}$ and weakly to A$_{KKAA}$, but not to E$_{KKAA}$ and D$_{KKAA}$. In sum, SpA$_{KKAA}$-mAbs that afforded the highest levels of protection against staphylococcal disease in mice bound some or all of the five IgBDs, but not the peptides encompassing only one or two of three helices of IgBDs. These data suggest that protective mAbs recognize conformational epitopes of the triple-helical bundle for each IgBD.

Figure 2:
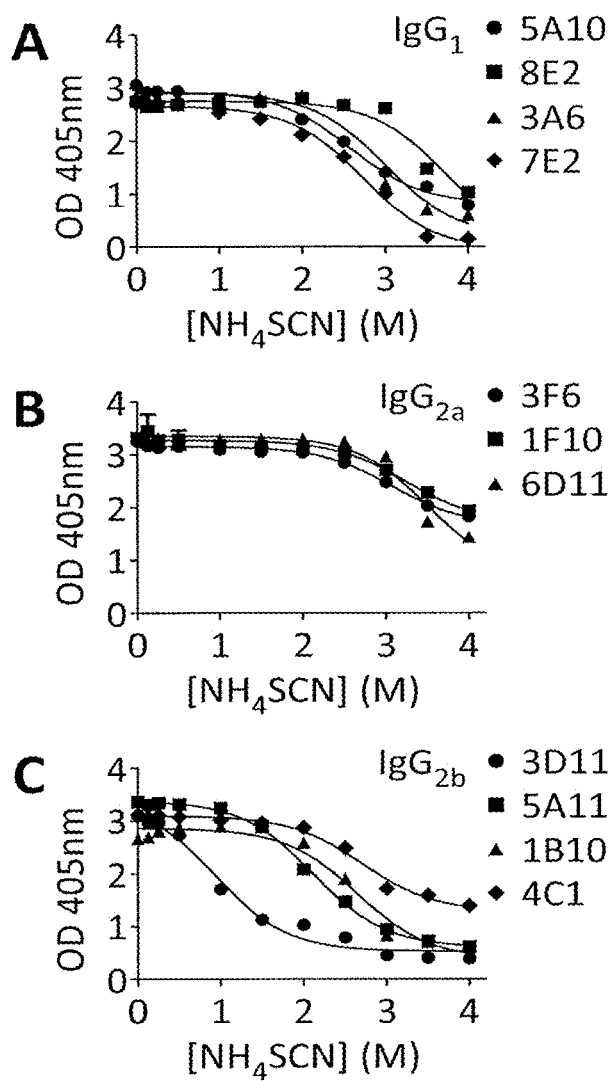
FIGS. 2A-C: Avidity of protein A specific monoclonal antibodies. Monoclonal antibodies were incubated with increasing concentration (0-4M) of ammonium thiocyanate to perturb the antigen-antibody specific interaction in (A) $IgG_1$ isotype monoclonal antibodies, (B) $IgG_{2a}$ isotype monoclonal antibodies and (C) $IgG_{2b}$ isotype monoclonal antibodies. Data are the means and error bars represent ±SEM. Results in A-C are representative of three independent analyses.

To examine whether the avidities of mAbs play a significant role in immune protection, ELISA was performed in the presence of increasing concentrations of the chaotropic reagent ammonium thiocyanate (FIG. 2). The measured avidity of mAb 3F6 was significantly higher than that of mAb 5A10 and 3D11 (FIG. 2). Of note, 3D11 displayed relatively low avidity, which may be due to its specific interaction with only two of the five IgBDs (FIG. 2 and Table 3). From this we conclude that the avidities of mAbs may not be a major determinant of their immune protection in mice.

United States Patent Application Publications US 2008/0118937 and US 2010/0047252 describe a murine hybridoma cell line that was derived from a mouse following immunization with wild-type protein A. The corresponding antibody, mAb 358A76.1.1, was reported to associate with wild-type protein A; however, the molecular nature of this association has not yet been revealed. To further explore the nature of B cell responses to wild-type protein A, mAb 358A76.1.1 was isolated and examined for its functional attributes. Unlike SpAKKAA-mAbs, the 358A76.1 antibody bound only to the E domain of SpA, but not any of the four other IgBDs (D, A, B and C). Furthermore, mAb 358A76.1 neither neutralized protein A nor promoted opsonophagocytic killing of staphylococci, and passive transfer of mAb 358A76.1 did not protect mice against *S. aureus* disease.

Monoclonal Antibody 358A76.1 Weakly Binds to Only the E Domain of SpA.

To determine the affinity constant (K$_a$=[mAb·Ag]/[mAb]×[Ag]) of mAb 358A76.1 for binding to protein A, microtiter plates were coated with either SpA$_{KKAA}$, individual IgBDs (E$_{KKAA}$, D$_{KKAA}$, A$_{KKAA}$, B$_{KKAA}$ or C$_{KKAA}$), as well as synthetic peptides encompassing individual helixes (H1, H2, and H3) or two helices (H1+2 and H2+3) of the E$_{KKAA}$ triple helical bundle. mAb 3F6 is a SpA$_{KKAA}$-derived mouse monoclonal antibody with high affinity for full-length SpA$_{KKAA}$ (K$_a$ 22.97×10$^9$ M$^{-1}$) and each of the five IgBDs (K$_a$ 12.41-27.46×10$^9$ M$^{-1}$). Compared to mAb 3F6, mAb 358A76.1 displayed much weaker affinity for SpA$_{KKAA}$ (K$_a$ 1.00×10$^9$ M$^{-1}$, FIG. 10A-B). Of note, mAb 358A76.1 bound only to E$_{KKAA}$ (K$_a$ 0.21×10$^9$ M$^{-1}$) but not to any of the other four IgBDs (D$_{KKAA}$, A$_{KKAA}$, B$_{KKAA}$ or C$_{KKAA}$, Table 6). Furthermore, mAb 358A76.1 did not recognize any of the synthetic peptides encompassing one or two helices of the E$_{KKAA}$ IgBD (H1, H2, H3, H1+2, and H2+3). In contrast, mAb 3F6 displayed weak affinity for helix 1+2 peptide (Table 6). An alignment of the amino acid sequences of all five IgBDs revealed that the E domain is the most dissimilar domain (Sjodahl, 1977). Nevertheless, the E domain, just like the other four IgBDs, associates with human and animal immunoglobulin and the significance of its dissimilarity has not yet been appreciated (Moks et al., 1986) (FIG. 10C-D). It is possible that mAb 358A76.1 specifically binds a conformational epitope involving the non-conserved amino acids of helix 1 and 3 of the E domain (FIG. 10C-D).

To examine whether mAbs 3F6 and 358A76.1 share epitope binding sites on SpA$_{KKAA}$ (E$_{KKAA}$), we performed competitive ELISA using increasing concentrations of IgG$_{2a}$ isotype control, mAb 358A76.1 or mAb 3F6. At 30 μg·ml$^{-1}$ concentration, isotype control antibody (IgG$_{2a}$) did not interfere with the binding of HRP-conjugated mAb 358A76.1 or mAb 3F6 to SpA$_{KKAA}$ (FIG. 10E). As expected, mAb 358A76.1 competed with HRP-conjugated mAb 358A76.1 for binding to SpA$_{KKAA}$, however it did not interfere with the binding of HRP-conjugated mAb 3F6 (FIG. 10E). Of note, mAb 3F6 was able to completely block the association of HRP-conjugated mAb 358A76.1 to SpA$_{KKAA}$ (96.4% inhibition, FIG. 10E), whereas mAb 358A76.1 generated only 88.0% inhibition (mAb 3F6 vs. mAb 358A76.1, P=0.0007).

Monoclonal Antibody 358A76.1 does not Elicit Protective Immunity in Mice.

Cohorts of BALB/c mice were injected into the intraperitoneal cavity with 5 mg·kg$^{-1}$ mAb 358A76.1 or mAb 3F6. Passively immunized animals were challenged with *S. aureus* USA300 (LAC), the highly virulent community-associated MRSA strain that is epidemic in the United States (Diep et al., 2006, Kennedy et al., 2008). Compared to IgG2a isotype mAb-treated controls, animals that received mAb 3F6 harbored a reduced bacterial load in renal tissues (1.26 log$_{10}$ CFU·g$^{-1}$ reduction; P=0.0021, FIG. 11A). Interestingly, animals that received mAb 358A76.1 displayed only a small reduction in bacterial load, which failed to achieve statistical significance (0.42 log$_{10}$ CFU·g$^{-1}$ reduction; P=0.0948, FIG. 11A). Compared to mAb 358A76.1, passive transfer of mAb 3F6 generated increased protection against CA-MRSA strain USA300 in immunized mice (0.84 log$_{10}$ CFU·g$^{-1}$ reduction; P=0.0011, FIG. 11A).

Opsonophagocytic killing of invasive microbes is a key defense strategy of infected hosts and also represents a correlate of protective immunity for many different bacterial vaccines (Robbins et al., 1987, Robbins et al., 1990). Using an assay of opsonophagocytic killing in fresh mouse blood, we asked whether mAb 358A76.1 can promote opsonophagocytic killing of MRSA strain USA300. Briefly, anti-coagulated blood obtained from naïve 6 week old BALB/c mice was incubated with *S. aureus* USA300 in the presence or absence of 10 µg·ml$^{-1}$ mAb 358A76.1, mAb 3F6 or mAb IgG2a isotype control. Blood samples were lysed, plated on agar medium and staphylococcal load enumerated. In contrast to mAb 3F6, which reduced the staphylococcal load in blood by 49%, mAbs 358A76.1 and IgG2a-control failed to activate opsonophagocytic killing of staphylococci (mAb 3F6 vs. PBS, P<0.0001; mAb 3F6 vs. 358A76.1, P=0.0007; FIG. 11B).

During infection, protein A captures and decorates the surface of staphylococci with immunoglobulin. By associating with the Fcγ domain of immunoglobulin, SpA blocks complement activation, engagement Fc receptors and opsonization of staphylococci by phagocytes. Furthermore, SpA molecules that are released from the bacterial surface crosslink $V_H3$-type B cell receptors to activate lymphocytes, eventually triggering their apoptotic demise and interfering with the development of adaptive immune responses against staphylococci. We used ELISA to determine whether mAb 358A76.1 can neutralize the immunoglobulin binding activities of protein A. As controls, at 6 µg·ml$^{-1}$ and 30 µg·ml$^{-1}$ mAb 3F6 neutralized the ability of protein A to bind human IgG binding, whereas the IgG2a isotype control mAb did not (FIG. 11C). Furthermore, at a concentration of 6 µg·ml$^{-1}$ or 30 µg·ml$^{-1}$ mAb 358A76.1 did not block the association of the human IgG to protein A (FIG. 11C).

TABLE 3

Association constants of mAb binding to SpA$_{KKAA}$ and its fragments

| | | Association constant (nM$^{-1}$) | | | | | | | | | |
|---|---|---|---|---|---|---|---|---|---|---|---|
| | | SpA IgG binding domains | | | | | Helix motif of SpA-E | | | | |
| [a]Antibody | SpA$_{KKAA}$ | E | D | A | B | C | H1 | H2 | H3 | H1 + 2 | H-2 + 3 |
| | | IgG$_1$ | | | | | | | | | |
| 5A10 | 8.47 | 9.40 | 8.19 | 8.08 | 7.03 | 10.12 | < | < | < | < | < |
| 8E2 | 1.56 | 1.40 | 1.51 | 1.52 | 1.14 | 1.26 | < | < | < | 0.29 | < |
| 3A6 | 1.37 | 1.38 | < | 2.05 | 0.64 | 0.04 | 0.06 | < | 0.01 | 0.44 | < |
| 7E2 | 0.31 | 0.29 | 0.30 | 0.36 | 0.32 | 0.28 | < | < | < | < | < |
| | | IgG$_{2a}$ | | | | | | | | | |
| 3F6 | 22.97 | 17.69 | 12.41 | 20.15 | 27.46 | 26.46 | < | 0.01 | < | 0.41 | 0.01 |
| 1F10 | 2.46 | 2.21 | 1.80 | 2.12 | 2.85 | 2.70 | < | < | < | 0.63 | < |
| 6D11 | 5.37 | 4.34 | 2.42 | 2.23 | 3.34 | 4.75 | 0.27 | 0.01 | < | 5.22 | 0.00 |
| | | IgG$_{2b}$ | | | | | | | | | |
| 3D11 | 3.93 | < | < | 0.87 | 3.92 | 3.60 | 0.02 | < | < | < | < |
| 5A11 | 8.75 | 5.10 | 5.75 | 6.61 | 5.03 | 6.04 | < | < | < | 0.02 | < |
| 1B10 | 4.31 | 4.35 | 2.78 | 2.74 | 2.30 | 4.21 | < | < | < | < | 0.01 |
| 4C1 | 4.68 | 2.38 | 2.56 | 3.02 | 3.21 | 2.99 | 0.07 | 0.01 | 0.01 | 1.95 | 0.04 |
| 2F2 | 1.90 | 1.72 | 1.76 | 1.37 | 1.13 | 1.8 | < | < | < | < | < |
| 8D4 | 10.47 | 7.65 | 9.85 | 11.94 | 0.07 | < | 3.20 | < | < | 4.88 | < |
| 7D11 | 5.46 | 3.14 | 3.51 | 4.15 | 4.62 | 6.02 | < | < | < | < | < |
| 2C3 | 6.84 | 5.35 | 3.41 | 4.25 | 3.90 | 6.33 | < | < | < | < | < |
| 4C5 | 4.42 | < | 1.76 | 4.57 | 1.8 | 2.11 | < | < | < | < | < |
| 6B2 | 4.47 | 3.2 | 2.52 | 4.19 | 4.55 | 4.23 | 0.05 | 0.23 | < | 4.54 | < |
| 4D5 | 6.17 | < | < | 5.30 | 4.89 | 5.24 | < | < | < | < | < |
| 2B8 | 4.79 | 2.33 | 2.25 | 3.05 | 3.68 | 3.06 | < | 0.23 | < | 3.37 | < |
| 1H7 | 2.86 | 2.42 | 2.17 | 2.37 | 2.57 | 4.43 | < | < | < | < | < |

[a]Affinity purified antibodies (1 mg ml$^{-1}$) were serially diluted across the ELISA plate coated with cognate antigens (100 nM) to measure the association constant by Prism (GraphPad Software, Inc.).

TABLE 6

Association constants for the binding of mAbs 358A76 and 3F6 to SpA$_{KKAA}$ and its fragments

| [a]mAb | Association constant ($\times 10^9$ M$^{-1}$) for antigen or antigen fragment | | | | | | | | | | |
|---|---|---|---|---|---|---|---|---|---|---|---|
| | | IgG binding domains of protein A | | | | | Segments of the E$_{KKAA}$ triple-helical bundle | | | | |
| IgG2α | SpA$_{KKAA}$ | E$_{KKAA}$ | D$_{KKAA}$ | A$_{KKAA}$ | B$_{KKAA}$ | C$_{KKAA}$ | H1 | H2 | H3 | H1 + 2 | H2 + 3 |
| 358A76 | 1.00 | 0.21 | < | < | < | < | < | < | < | < | < |
| 3F6 | 22.97 | 17.69 | 12.41 | 20.15 | 27.46 | 26.46 | < | 0.01 | < | 0.41 | 0.01 |

[a]Affinity purified antibodies (100 μg · ml$^{-1}$) were serially diluted across ELISA plates coated with antigens (20 nM for SpA$_{KKAA}$ and 100 nM for IgG binding domains) to calculate the association constant using Prism ® (GraphPad Software, Inc.). To study the binding of antibodies to protein A antigen, we used the SpA$_{KKAA}$ variant (residues 1-291 of mature SpA harboring six N-terminal histidyl residues) with four amino acid substitutions in each of the five immunoglobulin binding domains (IgBD) of protein A [E (residues 1-56), D (residues 57-117), A (residues 118-175), B (residues 176-233) and C (residues 234-291)]. In each IgBD, the glutamines at position 9 and 10 (amino acid residues from IgBD-E) were replaced with lysine (Q$^9$K, Q$^{10}$K) and aspartic acids 36 and 37 were substituted with alanine (D$^{36}$A, D$^{37}$A). The same substitutions were introduced into proteins spanning individual IgBDs: E$_{KKAA}$, D$_{KKAA}$, A$_{KKAA}$, B$_{KKAA}$ and C$_{KKAA}$ (all expressed and purified with an N-terminal six histidyl tag). SpA$_{KKAA}$ and individual IgBDs were purified by affinity chromatography from E. coli extracts. Peptides H1, H2, H3, H1 + 2, and H2 + 3 were synthesized on a peptide synthesizer and purified via HPLC. The peptides encompass helices 1 (H1: NH$_2$-AQHDEAKKNAFYQVLNMPNLNA-COOH), 2 (H2: NH$_2$-NMPNLNADQRNGFIQSLKAAPSQ-COOH), 3 (H3: NH$_2$-AAP-SQSANVLGEAQKLNDSQAPK-COOH), 1 + 2 (H1 + 2: NH$_2$-AQHDEAKKNAFYQVLNMPNLNADQRNGFIQSLKAAPSQ-COOH) or 2 + 3 (H2 + 3: NH$_2$-NMPNLNADQRNGFIQSLKAAPSQSANVLGEAQKLNDSQAPK-COOH) of the triple helical bundle of the E$_{KKAA}$ IgBD (residues 1-56 of SpA$_{KKAA}$: NH$_2$- AQHDEAKKNAFYQVLNMPNLNADQRNGFIQSLKAAP-SQSANVLGEAQKLNDSQAPK-COOH).
[b]The symbol < signifies measurements that were too low to permit the determination of the association constant.

mAb 3F6 Binds Sbi.

Sbi, a secreted protein of S. aureus, is comprised of five distinct domains (Zhang et al., 1998). Two N-terminal domains (1 and 2) are homologous to the IgBDs of SpA (Zhang et al., 1999). Domains 3 and 4 associate with complement components C3 and factor H and the C-terminal domain has been proposed to retain some secreted Sbi molecules in the staphylococcal envelope by binding to lipoteichoic acids (Burman et al., 2008, Smith et al., 2012). Domains 1 and 2 bind to the Fc portion of immunoglobulins (Atkins et al., 2008); this activity, in concert with the C3 and factor H binding attributes of domains 3 and 4, promotes the futile consumption of fluid complement components (Haupt et al., 2008). Sbi does not seem to exert B cell superantigen activity, as its two IgBDs (domains 1 and 2) lack the canonical two aspartic acid residues at position 36 and 37 (Graille et al., 2000, Lim et al 2011). His-Sbi$_{1-4}$, a recombinant protein encompassing both IgBDs and the complement binding domains, retained human IgG in an affinity chromatography experiment. His-Sbi$_{1-4/KKAA}$ is a variant with lysine (K) substitutions of conserved glutamine residues (Q$^{51,52}$ and Q$^{103,104}$) in domains 1 and 2, i.e. the predicted Fcγ binding sites of the Sbi IgBDs, and alanine (A) substitutions of arginine (R$^{231}$) and aspartic acid (D$^{238}$) residues of the complement binding domain (Haupt et al., 2008). His-Sbi$_{1-4/KKAA}$ did not retain human IgG during affinity chromatography. When examined by ELISA, His-Sbi$_{1-4}$ bound to mouse as well as human IgG and to both the Fc and Fab domains of human IgG, whereas His-Sbi$_{1-4/KKAA}$ did not. mAbs 5A10 and 3D11 did not bind to His-Sbi$_{1-4/KKAA}$, however 3F6 bound to the protein. Thus, mAb 3F6 may neutralize Sbi or remove secreted Sbi from circulation, thereby preventing the consumption of complement factor C3 by staphylococci.

Figure 3:
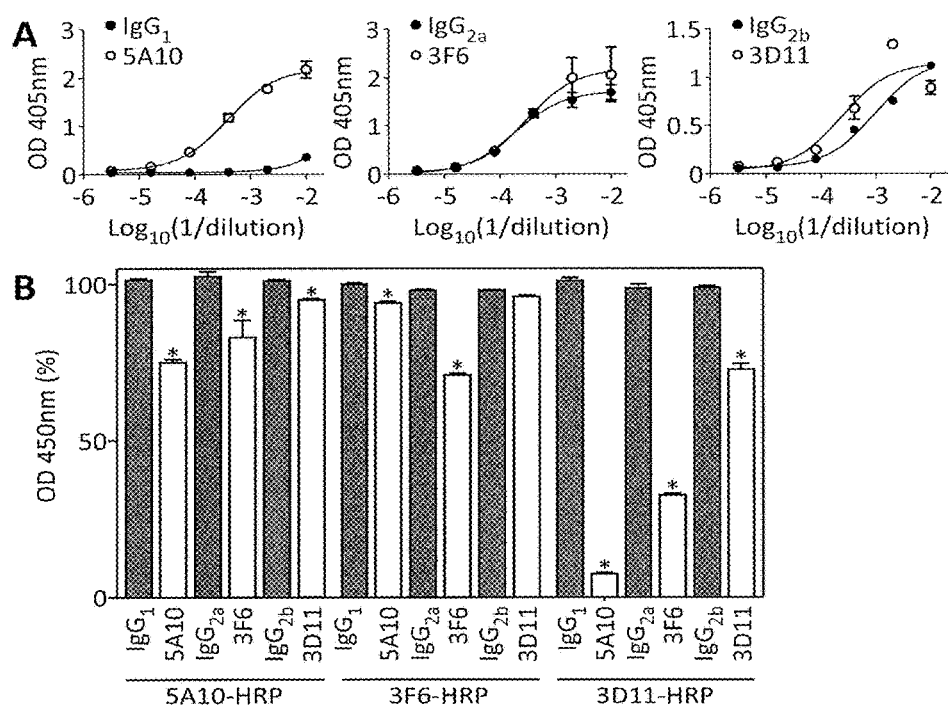
FIGS. 3A-B: $SpA_{KKAA}$-specific mAbs bind wild-type protein A. (A) ELISA examining the binding of immobilized wild-type protein A (SpA) to isotype control antibodies ($IgG_1$, $IgG_{2a}$ or $IgG_{2b}$) or $SpA_{KKAA}$-specific mAbs (5A10, 3F6 and 3D11). (B) Association of horse radish peroxidase (HRP)-conjugated $SpA_{KKAA}$-specific mAbs (5A10-HRP, 3F6-HRP and 3D11-HRP) to immobilized $SpA_{KKAA}$ was examined in a plate reader experiment where $SpA_{KKAA}$ was first incubated with isotype control antibodies ($IgG_1$, $IgG_{2a}$ or $IgG_{2b}$) or three different $SpA_{KKAA}$-specific mAbs (5A10, 3F6 and 3D11) to assess the possibility of competitive inhibition for antibody that bind the same or closely related sites (n=3). The values at $OD_{405\ nm}$ were measured and normalized to the interaction of $SpA_{KKAA}$ and HRP-conjugated SpA specific mAbs. Data are the means and error bars represent ±SEM. Data in panels A and B are representative of three independent analyses. The asterisks denotes statistical significance (P<0.05).

Binding site competition experiments with SpA$_{KKAA}$-mAbs. ELISA studies revealed that the three mAbs 5A10, 3F6 and 3D11 bound with similar affinities to wild-type SpA (FIG. 3A). Compared to 5A10, the IgG$_1$ control antibodies displayed little affinity for SpA. Further, the affinity of the IgG$_{2b}$ control antibody was reduced compared to that of mAb 3D11. Compared to 3F6, the IgG$_{2a}$ control antibody bound SpA with slightly reduced affinity. In a competitive ELISA assay with horseradish peroxidase conjugated mAbs (5A10-HRP, 3F6-HRP and 3D11-HRP), isotype control antibodies did not interfere with the binding of HRP-conjugated mAbs to SpA (FIG. 3B). The addition of equimolar amounts of each mAb reduced the binding of the corresponding HRP-conjugate (FIG. 3B). mAb 3D11 did not prevent the association of HRP-5A10 or HRP-3F6 with SpA, however mAbs 5A10 and 3F6 interfered with HRP-3D11 binding to SpA. mAb 3F6 caused some reduction in the binding of HRP-5A10 to SpA (FIG. 3B). Finally, mAb 5A10 was a weak competitor for the binding of 3F6-HRP to SpA (FIG. 3B). These data suggest that the binding sites for the three mAbs on the surface of the triple-helical bundles of SpA may be in close proximity to one another or even partially overlap (Table 3).

SpA$_{KKAA}$-mAbs Prevent the Association of Immunoglobulin with Protein A.

Mouse antibodies of clan V$_H$3 related families (e.g. 7183, J606 and 5107) bind SpA via their Fab portion, whereas those of other VH families (J558, Q52, Sm7, VH10, VH11 and VH12) do not (Cary et al., 1999). The amino acid sequence of the complementarity determining region (CDR) of SpA$_{KKAA}$-specific mAbs was determined by sequencing cDNA derived from hybridoma transcripts. The data showed that mAb 5A10 belongs to the clan V$_H$3 7183 family; its Fab domain likely displays affinity for SpA (Table 4). mAbs 3F6 and 3D11 are members of the VH10 and J558 families, respectively (Table 4); Fab domains of these antibody families are not known to associate with SpA.

TABLE 4

Amino acid sequences of CDR regions of monoclonal antibodies

Amino acid sequencing data of protein
A specific monoclonal antibodies

| $^a$mAb | MouseVH family | CDR1 | CDR2 | CDR3 |
|---|---|---|---|---|
| 5A10 | 7183 | ...SSVSY... | ...DTS... | ...QQWSSYPPT... |
| 3F6 | $V_H$10 | ...ESVEYSGASL... | ...AAS... | ...QQSRKVPST... |
| 3D11 | J558 | ...SSVSY... | ...EIS... | ...QQWSYPFT... |

$^a$Amplified PCR products from cDNA which was synthesized from total RNA extracted from hybridoma cells were sequenced and analyzed using IMGT Vquest.

Wild-type SpA and its variants $SpA_{KKAA}$, $SpA_{KK}$ and $SpA_{AA}$ were purified and used for ELISA binding studies with human IgG. As expected, SpA bound to IgG or its Fcγ and F(ab)$_2$ fragments, whereas $SpA_{KKAA}$ did not (FIG. 7). The $SpA_{KK}$ variant (harboring lysine substitutions at all 10 glutamine residues) was impaired in its ability to bind Fcγ but not F(ab)$_2$ fragments, whereas the $SpA_{AA}$ variant (harboring alanine substitutions at all 10 aspartic acid residues) bound to Fcγ but not F(ab)$_2$ (FIG. 7). The binding of human IgG to SpA was blocked by all three mAbs (5A10, 3F6 and 3D11) in a manner that exceeded the competition of isotype control mAbs (FIG. 4A). All three antibodies interfered with the binding of human IgG to $SpA_{KK}$ (Fab binding) or to $SpA_{AA}$ (Fab binding) (FIG. 4A). Thus, $SpA_{KKAA}$-specific mAbs prevent the non-immune association of SpA with immunoglobulin. Based on these data, we presume that protein A-specific mAbs interact with conformational epitopes involving helix 2 of IgBDs, a structural element involved in the Fcγ and Fab interactions of SpA.

If mAb 3F6 binds wild-type SpA as an antigen on the staphylococcal surface, its Fcγ domain should be available for recognition by complement or Fc receptors on the surface of immune cells. To test this prediction, S. aureus was incubated with 3F6, its isotype control and affinity purified $Sbi_{1-4}$. Antibody-mediated co-sedimentation led to the depletion of soluble $Sbi_{1-4}$ from the supernatant, which was analyzed as a measure for the availability of Fcγ sites on the bacterial surface. Incubation of staphylococci with the control mAb, which can only associate with SpA in a non-immune fashion, caused a modest reduction of soluble $Sbi_{1-4}$ (FIG. 4B). In contrast, incubation of staphylococci with mAb 3F6 depleted soluble $Sbi_{1-4}$, indicating that mAb 3F6 bound SpA antigen on the bacterial surface while presenting its Fcγ domain for association with $Sbi_{1-4}$ (FIG. 4B).

To test whether the binding of mAb 3F6 to SpA does occur in vivo, BALB/c mice were immunized with mAb 3F6 or the isotype control antibody. Following the injection of purified SpA into the peritoneal cavity, its abundance in circulation was assessed by sampling blood over the next 30 minutes. Compared to animals treated with control mAb, injection of mAb 3F6-treated animals caused accelerated clearance of SpA from the bloodstream (FIG. 4C). It is presumed that immune recognition of SpA by mAb 3F6 provides for its Fcγ domain to mediate Fc-receptor mediated removal of antigen-antibody complexes from the blood stream.

$SpA_{KKAA}$-mAbs Promote Opsonophagocytic Killing of Staphylococci in Human and Mouse Blood.

Figure 5:
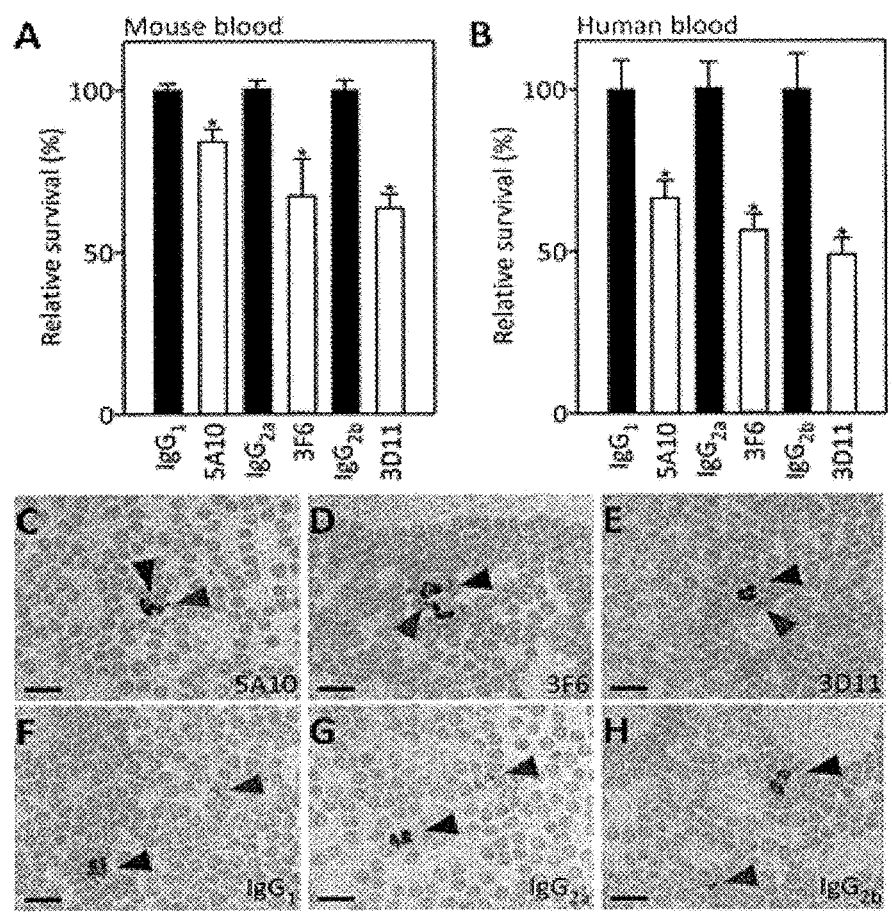
FIGS. 5A-H: SpA$_{KKAA}$-mAbs promote opsonophagocytic killing of *S. aureus* in mouse and human blood. (A) Lepirudin anticoagulated mouse blood was incubated with 5×10$^5$ CFU *S. aureus* Newman in the presence of isotype mouse antibody controls or SpA$_{KKAA}$-mAbs (2 μg·ml$^{-1}$) for 30 minutes and survival measured (n=3). (B) Lepirudin anti-coagulated human whole blood was incubated with 5×10$^6$ CFU *S. aureus* MW2 in the presence of isotype mouse antibody controls or SpA$_{KKAA}$-mAbs (10 μg·ml$^{-1}$) for 120 minutes and survival measured (n=3). (C—H) At 60 minutes of incubation of staphylococci in anticoagulated human blood, clusters of extracellular staphylococci were detected in samples incubated with mouse isotype antibody controls (gray arrowheads), whereas staphylococci were found within neutrophils (black arrowheads) in samples with SpA$_{KKAA}$-mAbs. Data are the means and error bars represent ±SEM. Results in A-H are representative of three independent analyses. The asterisks denotes statistical significance (P<0.05).

Eliciting adaptive immune responses that promote opsonophagocytic killing of pathogens is a universal goal for vaccine development and licensure (Robbins et al., 1996). This has not been achieved for S. aureus, as this pathogen is armed against opsonic antibodies via its surface exposed and secreted SpA and Sbi molecules (Kim et al., 2011). To test whether $SpA_{KKAA}$-mAbs can promote opsonophagocytosis, an assay of bacterial killing in fresh blood developed by Rebecca Lancefield was employed (Lancefield, 1928). Lepirudin anti-coagulated blood from naïve 6 week old BALB/c mice was incubated with MSSA strain Newman in the presence or absence of 2 µg·ml$^{-1}$ mAbs 5A10, 3F6 and 3D11 or their isotype controls. Blood samples were lysed, plated on agar medium and staphylococcal load enumerated (FIG. 5A). All three mAbs triggered opsonophagocytic killing of staphylococci, which ranged from 37% of the inoculum (3D11, P=0.0025), to 33% (3F6, P=0.0478) and 16% (5A10, P=0.0280). As a test for opsonophagocytic killing of staphylococci in human blood, the inventors recruited healthy human volunteers and examined their serum for antibodies specific for $SpA_{KKAA}$. As reported before, none of the volunteers harbored serum antibodies directed against protein A (data not shown)(Kim et al., 2010a). Anti-coagulated fresh human blood samples were incubated with MRSA strain USA400 (MW2) in the presence or absence of 10 µg·ml$^{-1}$ mAbs 5A10, 3F6 and 3D11 or their isotype controls (FIG. 5B). All three mAbs triggered opsonophagocytic killing of staphylococci, which ranged from 52% of the inoculum (3D11, P=0.0002), to 44% (3F6, P=0.0001) and 34% (5A10, P=0.0035). Blood samples were spread on glass slides, stained with Giemsa and analyzed by microscopy. Blood samples incubated in the presence of mAbs 5A10, 3F6 and 3D11 harbored staphylococci that were associated with neutrophils, i.e. they may be associated with these leukocytes or located within cells (FIG. 5C-E). Blood samples incubated with isotype control mAbs harbored clusters of extracellular staphylococci (red arrowheads) as well as staphylococci that were associated with leukocytes (blue arrowheads, (FIG. 5F-H).

DISCUSSION

Monoclonal antibodies offer unique opportunities to investigate the biological attributes of humoral adaptive immune responses to microbial surface products, revealing both the molecular nature of microbial immune evasion and of protective immunity (Fischetti, 1989). For example, group A streptococcal M protein, a key virulence factor and α-helical coiled-coil surface protein (Phillips et al., 1981), confers resistance to opsonophagocytic clearance, which may be overcome by humoral adaptive immune responses during infection (Lancefield, 1962; Scott et al., 1986). mAbs that bind to the α-helical coiled-coil of M protein cannot induce opsonophagocytic killing of group A streptococci, which is however achieved by mAbs directed against the N-terminal, random coil domain (Jones and Fischetti, 1988; Jones et al., 1986). The N-terminal domain of M proteins is highly variable between clinical isolates, which represents the molecular basis for type-specific immunity (Hollingshead et al., 1987; Lancefield, 1962).

Similar to streptococcal M protein, protein A also functions as the protective antigen of *S. aureus* (Stranger-Jones et al., 2006). Virtually all clinical isolates of *S. aureus* express protein A, however the amino acid sequence of its IgBDs is highly conserved (McCarthy and Lindsay, 2010). Staphylococcal infections in mice or humans do not elicit protein A-specific humoral immune responses (Kim et al., 2010a), which is explained by the B cell superantigen activity of this molecule (Silverman and Goodyear, 2006). Immunization with protein A variants, in particular the $SpA_{KKAA}$ molecule, elicits humoral immune responses in mice and rabbits; these antibodies crossreact with wild-type protein A and provide protection against staphylococcal disease in mice (Kim et al., 2010a). Affinity purified polyclonal rabbit antibodies can block the B cell superantigen activity of the wild-type protein A in mice and enhance the opsonophagocytic capacity of mouse neutrophils when incubated in anti-coagulated mouse blood. In addition, *S. aureus* mutants lacking the structural gene for protein A (spa) display significant defects in virulence, and also permit the development of humoral immune responses against many different staphylococcal antigens as well as the development of protective immunity (Cheng et al., 2009; Kim et al., 2011). Thus, antibodies that neutralize the immune-modulatory attributes of SpA may not only provide protection against acute staphylococcal infection, but may also enable the development of protective immune responses against other staphylococcal antigens and prevent recurrent *S. aureus* infections. The inventors tested this prediction by raising mAbs against $SpA_{KKAA}$. All monoclonal antibodies that elicited protective immunity in mice recognized conformational epitopes of protein A and interacted with the triple-helical fold of its IgBDs. Importantly, these monoclonal antibodies with strong affinity and cross-reactivity for multiple or all IgBDs of $SpA_{KKAA}$ recognized also wild-type protein A. When tested in vitro, mAbs, in particular 5A10, 3F6 and 3D11, prevented protein A association with the Fcγ and the Fab domains of immunoglobulins and triggered opsonophagocytic killing of *S. aureus* by phagocytes in mouse and human blood. When injected into the peritoneal cavity of mice, mAbs elicited significant immune protection against both MSSA and MRSA *S. aureus* isolates. Further, $SpA_{KKAA}$-mAb mediated neutralization of SpA in vivo stimulated humoral immune responses against several different *S. aureus* antigens, supporting the hypothesis that $SpA_{KKAA}$-antibodies inhibit the B cell superantigen activities of staphylococci.

Of note, the magnitude of antibody responses toward staphylococcal antigens in passively immunized mice were much lower than the immune responses elicited in mice actively immunized with $SpA_{KKAA}$. The main difference between active and passive immunization strategies lies in the development of antigen specific T/B cell populations governing host immune responses, which are the consequence of active immunization strategies. Future studies are warranted to determine if the protein A specific T/B cells are critical in raising appropriate systemic immune responses such as $T_H1/17$ mediated recruitment of functional phagocytes against *S. aureus* infections (Spellberg et al., 2012).

Previous work demonstrated superantigen activity of protein A towards $V_H3$-type B cell receptors in mice (Goodyear et al., 2003). Of note, only 5-10% of mouse B cells are $V_H3$-clonal and susceptible to protein A superantigen (Silverman et al., 2006). Nevertheless, protein A mutant staphylococci display a profound defect in the pathogenesis of abscess formation in mouse models for this disease (Cheng et al., 2009, Kim et al., 2011). In contrast to mice, human $V_H3$ clonal B cells comprise up to 50% of the total B cell population (Berberian et al., 1993, Huang et al 1992), suggesting that the impact of protein A superantigen activity during staphylococcal infection is likely greater for human B cell populations (Silverman et al., 2006). If so, protein A-mediated B cell activation may trigger biased use of $V_H3$ B cell clones and the development of non-physiological B cell populations. Ultimately, staphylococcal protein A is expected to human hosts of $V_H3$ positive B cells and $V_H3$-type antibodies. A similar scenario is encountered with the HIV envelope glycoprotein gp 120, which also interacts with $V_H3$ clonal B cells, causing a clonal deficit of $V_H3$ B cells (antibody genes) in AIDS patients (Berberian et al., 1993, Berberian et al 1991). These events are likely key factors in the prevention of neutralizing antibody responses during HIV and *S. aureus* infection (Kim et al., 2012b).

Work by others has sought to isolate monoclonal antibodies against protein A. One such antibody, SPA27 (Sigma, St. Louis, Mo.) was typed as mouse IgG1, an antibody class whose Fcγ domain does not interact with protein A (Kronvall et al., 1970). Nevertheless, even IgG1 sub-type antibodies can be bound by protein A via pseudo-immune association assuming these antibodies harbor VH3-type Fab domains (Cary et al., 1999, Sasso et al., 1989). We recently developed reagents that can distinguish between these possibilities. For example, wild-type protein A (SpA) binds immunoglobulins via the Fcγ and the VH3-type Fab domains (Silverman et al., 2006). $SpA_{KK}$ associates only with the Fab domains of VH3-type antibodies, whereas $SpA_{AA}$ binds only to the Fcγ domain of IgG but not to the Fab domain of VH3-type immunoglobulin (Kim et al., 2012a). Using these reagents, we observed that SPA27 binds to wild-type SpA and $SpA_{KK}$, but not to $Sp_{AAA}$ or $SpA_{KKAA}$ (Kim et al., 2012a). Thus, SPA27, which was isolated from a hybridoma following immunization of mice with wild-type protein A from *S. aureus* Cowan1, does not specifically recognize protein A (Kim et al., 2012a). Rather, SPA27 is bound by protein A (Kim et al., 2012a). As could be expected from these observations, SPA27 cannot neutralize the IgG or IgM binding activities of protein A and it does not provide protection in mice that are subsequently challenged via *S. aureus* infection (Kim et al., 2012a).

We wondered whether the inability of the host immune system to produce neutralizing antibodies during *S. aureus* infection or following immunization with wild-type protein A represents a general phenomenon (Kim et al., 2012a, Kim et al 2012b). To test this model, we purified mAb 358A76.1, an antibody that was isolated following immunization of mice with wild-type protein A from *S. aureus* Cowan1 (Sjoquist et al., 1972) (United States patent US2008/0118937A1 and US2010/0047252A1). Unlike mAb SPA27, mAb 358A76.1 displayed immune reactivity with SpA, $SpA_{KK}$, $Sp_{AAA}$ and $SpA_{KKAA}$ (Kim et al., 2012a). We observed that the specific binding site of mAb 358A76.1 is restricted to $E_{KKAA}$ domain, and that the antibody does not recognize the $D_{KKAA}$, $A_{KKAA}$, $B_{KKAA}$ and $C_{KKAA}$ domains. On the basis of amino acid dissimilarity between $E_{KKAA}$ and the other four IgBDs, we presume that mAb 358A76.1 recognizes a conformational epitope on the surface of the E-IgBD domain. The association between mAb 358A76.1 and the E domain of protein A cannot neutralize the other four IgBDs (D, A, B and C). Not surprisingly, passive transfer of mAb 358A76.1 into naïve mice does not confer protection against *S. aureus* challenge and does not trigger the opsonophagocytic killing of staphylococci in blood. Based on these observations we propose that only the immunization with non-toxigenic protein A, for example SpA$_{KKAA}$, can elicit the development of antibodies that neutralize all IgBDs of protein A and that confer protection against *S. aureus* disease.

Data presented herein provide corroborating evidence for the general hypothesis that the neutralization of the Fcγ and Fab binding activities of SpA represent a correlate for protective immunity against *S. aureus*: such antibodies are expected to trigger the opsonophagocytic killing of the pathogen in blood and to elicit antibodies that neutralize the secreted virulence factors of staphylococci (Mazmanian et al., 1999).

Sequence Analysis

Wildtype *S. aureus* Protein A interacts with human IgG through 2 non-antigenic binding sites. The first is with the Fc constant region and the second is with the Fab heavy chain of the human VH3 clan (the Fab binding also occurs with IgA and IgM). Thus, the mAbs that belong to the mouse clan that corresponds to the human VH3 likely have three possible, and perhaps competing binding affinities with the wildtype antigen, one for Fc, one for Fab, and the third the antigen specific binding mediated via the CDRs. Hybridoma cell lines that generate SpAKKAA-specific monoclonal antibodies were subjected to CDR sequencing analysis. Each individual antibody included two antigen recognitions sites (Fab fragments) wherein each Fab portion comprised three CDRs in the light chain and three CDRs in the heavy chain. The mAbs identified as conferring protection against *S. aureus* infection include 5A10, 3F6, 3D11, 5A11, 1B10 and 4C1.

3F6, which provided significant protection, presented the most distinctive sequence among a panel of SpAkkaa mAbs. Despite sharing the same CDR sequence of the light chain with 1F10 and 6D11, 3F6 has a unique CDR sequence in the heavy chain that distinguishes it from 1F10 and 6D11. Finally, 1F10 and 6D11 shared common heavy and light chain CDR sequences, suggesting they are sibling mAbs. Both the 1F10 and 6D11 antibodies failed to generate significant immune protection in mice. The three mAbs that produced the most promising protective effects and that have been further characterized (5A10, 3F6, and 2F2) are indicated in bold Three main groups of light chain sequences were identified, united by similar sequences. A first group comprised 3F6, 1F10, 6D11, 4C1, 6B2, 2B8, and 4C5, all of which shared common light chain CDR sequences, with the exception of one amino acid difference in 6B2 and two amino acid differences in 4C5. Despite sharing light chain sequences, these mAbs produced a variety of protective effects, suggesting that specific differences in the heavy chain sequences may significantly influence the functional effects of these mAbs. A second group shared a set of light chain CDR sequences (the heavy chain CDR sequences differed) and comprised 5A10 and 2F2, including one of the main protective antibodies, 5A10.

The percent identity of the corresponding CDRs of all antibodies were calculated and are presented in Tables 7-15 in a matrix format. The antibodies that had greater than 40% individual CDR sequence identity with respect to the individual CDRs of 3F6, 5A10, or 3D11 are summarized in Table 16. Consensus sequences for each set of CDRs that were greater than 40% identical to the corresponding CDRs of 3F6 are presented in Table 17.

TABLE 5

| | | Antibody sequences | | | | | |
|---|---|---|---|---|---|---|---|
| | | [a]Heavy Chain Sequence | | | [d]Light Chain Sequence | | |
| [d]mAb | [b]$V_H$ clan | CDR1 | CDR2 | CDR3 Amino acid sequence Nucleotide sequence | CDR1 | CDR2 | CDR3 Amino acid sequence Nucleotide sequence | [e]CFU reduction/Abcess Formation P values |

| | | | | | IgG1 | | | |
|---|---|---|---|---|---|---|---|---|
| 5A10 | $V_H$3 | GFAFSNYD (SEQ ID NO: 11) | ISSGGTYP (SEQ ID NO: 12) | ARGGFLITTRDYYA MDY (SEQ ID NO: 13) EVKLVESGGGLVKPGGSLKLSCAASGFAFSNYDMSWVRQTPEKR LEWVATISSGGTYPYYPDSVKGRFTISRDNAKNTLYLQLSSLRS EDTALYYCARGGFLITTRDYYAMDYWGQGTSVTVSS (SEQ ID NO: 14) Gaagtgaagctgtggagtctgggggaggcttagtgaagcctgg aggatcctgaaactctcctgtgcagcctctggattcgcttca gtaactatgacatgtcttggttcgccagactccggagaagagg ctggagtgggtcgcaaccattagtagtggtggtactaccccta ctatccagacagtgaaggcgtttcaccatctccagacaa atgccaaacacctgtactgcaattgagcagcctgaggtct gaggacacggcctgtactactgtgcaagacacggatatggtgat tacgcacaggattactatgctatggactactgggtcaaggaa cctcagtcaccgtctcctcag (SEQ ID NO: 15) | SSVSY (SEQ ID NO: 16) | DTS (SEQ ID NO: 17) | QQWSSYPPT (SEQ ID NO: 18) TIVLTQSPAIMSASPGEKVTMTCSASSSVSYMYWYQQKPG SSPRLLIYDTSNLASGVPVRFSGSGSGTSYSLTISRMEAE DAATYYCQQWSSYPPTFGGGTKLEIK (SEQ ID NO: 19) Acaattgtctcaccagtctccagcaatcatgtctgcat ctccagggagaagtccaccatgacctgcagtgcagctca agtaagttacatgtactggtaccagcagaagccagga tcctcccccagactccctgatttatgacacatccaactgg ctctggagtccctgtcgttcagtggcagtgggtctgg gaccctctacactctccacaatcagcagcgtggaggctgaa gatgctgcactttactactgccagtggagtagttacc cacccacgttcggaggggggaccaaagctggaaataaaac (SEQ ID NO: 20) | 0.0019/0.035 |
| 8E2 | $V_H$1 | GYTFTEYS (SEQ ID NO: 21) | FYPGSGYI (SEQ ID NO: 22) | ARHGYGNVVGYAM DY (SEQ ID NO: 23) KVQLQQSGAGLVKPGASVKLSCKASGYTFTEYSIHWVKQSSGQG LEWIGWFYPGSGYIYNEKFKDKATLTADKSSSTVYMEFSRLTS EDSAVYFCARHGYGNVVGYAMDYWGQGTSVTVSS (SEQ ID NO: 24) Aaggtccagctgcagcagtctgaagctgggactggtgaaccggg gcatccagtgaagctgtcctgcaaggctctgagctacactt cctgaatatggtataaacagagctctggacaagggt cttgagtgggattggatggttttattattataaa gtacaatgagaaatcaagagacaaggccacattgactgctgaca aatctccagactgctatatggattgtagatctgaatatctct gaagactctggctgctactgtgcaagacacggatatggtaa ctacgcaggattactatgctatgactactgggtcaaggaacctag tcaccgtctcctcag (SEQ ID NO: 25) | EIIYSY (SEQ ID NO: 26) | FAK (SEQ ID NO: 27) | QHHYGTPYT (SEQ ID NO: 28) DIQMTQSPASLSASVGETVTITCRASEIIYSYLAWYQQKQ GKSPQLLVYFAKTLAEGVPSRFSGSGSGTQFSLKINSLQP EDFGIYYCQHHYGTPYTFGGGTKLEIK (SEQ ID NO: 29) Aagtccagctgcaacagtctggagctggtggtggctgtgaaac cggggcatccagtgaagctgtcctgcaaggctctggcta cacctcactgatatgtaacactggggtaaacagagc tctgagtgggttggatggttgttataccctg gaagtggttatatatataagtacaatgacaaatcaagagca gccaattgactgctggacaaatcccaacacagtctat atggagtttaggtagttgacatctgaagactctggaggct actctgtgcaagacaccggtatggtaactactgtgggta ctatgtggactactgggtcaaggaacctaatcaccgtc tcctc (SEQ ID NO: 30) | 0.0620/0.1117 |
| 3A6 | $V_H$1 | GYNFTDYS (SEQ ID NO: 31) | INTETAES (SEQ ID NO: 32) | AHFDC (SEQ ID NO: 33) QIQLVQSGPELKKPGETVKISCKASGYNFTDYSMHWVKQAPGKG | QSLVHSNG NTY (SEQ ID NO: 36) DVVWMTQISLSLPVTLGDQASISCRASQSLVHSNGNTYLNW | KVS (SEQ ID NO: 37) | SQITYVPWT (SEQ ID NO: 38) | 0.3068/0.1497 |

TABLE 5-continued

Antibody sequences.

| mAb | VH clan | Heavy Chain Sequence CDR1 | CDR2 | CDR3 Amino acid sequence Nucleotide sequence | Light Chain Sequence CDR1 | CDR2 | CDR3 Amino acid sequence Nucleotide sequence | CFU reduction/Abcess Formation P values |
|---|---|---|---|---|---|---|---|---|
| | | | | | | | | |
| | | | | | LKWVGWINTETAESTYADDFKGRFAFSLETSASTAYLQINSLKD EDTAIFFCAHFDCWGQGTLTVSS (SEQ ID NO: 34) Cagatcccagtctgtgcagtctggacctgagctgaagaagcctgg agagacagtccctgcaaggctctctggttatattcca cagatattcaatgcactgggtgaagcaggctctccaggaaaggt ttaaagtgggtggatggacctgcctgcaagctgatcc atatgcagatgacttcaaggacggtttgcctctcttctggaaa cctctgccagcacggctacctattttctgtcccacatttgactgtggg gaggacacggctacctattttctgtcccacatttgactgtggg ccaggcaccaccctccactgtctctcca (SEQ ID NO: 35) | | | YLQKPGQSPKLLIHKVSNRFSGVPDRFSGSGSGTDFTLKI SRVEAEDLGVYFCSQITYYPWTFGGGTKLEIK (SEQ ID NO: 39) Gatgttgatgaccccaaattcactctcctgctgtca ctctggagatcaagcctccatctcttgcagagctagtca gagcttgtacacagtaatgaaacacctattaaatgg taccctgcagaaacgccagtccagctcctgatcc acaaagtctccaaccgattttctgggtcccagacaggtt cagtgcagtggatcagggacagattcacactcaagatc agcaagtggaggctgaggatctggagttttattctgct ctcaaattacatatgtcctgacgttgcgtgggcac caagctggaaatcaaac (SEQ ID NO: 40) | | 0.9396/0.7461 |
| 7E2 | VH | GYTFTDYS (SEQ ID NO: 41) | INTATGEP (SEQ ID NO: 42) | APQLTGPFAY (SEQ ID NO: 43) QIQLVQSGPELKKPGETVKISCKASGYTFTDYSVHWVKQAPGKG LKWMAWINTATGEPTFADDFKGRFAFSLETSARTAYLQINNLKN EDTATYFCAPQLTGPFAYWGHGTLVTVSA (SEQ ID NO: 44) Cagatcccagtctgtacagtctggacctgagttgaagaagcctgg agagacagtccctgcaaggctctctggttataccttca cagatattcagtgcactggtgaagcaggctctccaggaaaggt ttaaagtgggatggctggatctggatgcgactgtgagccag atttgcagatgactttcaaggacggccattttctgtcttctggaaat cctctgccagaacggctacatatttctgtgctcccccagttaactgccc tttgtctactggggccaacggaccctggtcactgtctctgca (SEQ ID NO: 45) | ENIHNY (SEQ ID NO: 46) | NAK (SEQ ID NO: 47) | QHSWSIPYT (SEQ ID NO: 48) DIQMTQSPASLSASVGETVTITCRASENIHNYLAWYQQKQ GKSPQLLVYNAKTLDGVPSRFSGSGSGTQFSLKINSLQA GDFGSYYCQHSWSIPYTFGGGTKLQIR (SEQ ID NO: 49) Gacatccagatgactcagtctccagctctccctatctcat ctgtgggagaaatgtcaccatcacatgtcgagcaagtga gaatattcacaatatttagcatggtatcagcagaaacag ggaaaatctccacagctcctggtcgtatatgcaagaaacct taacagatgtgccatcaaggttcagtggcagtggatc aggaacaaatttctctcaaatcaacagctgcaggct ggagatttggagttattactgccaacattcttggagta taccgtacacgtttgaggggggaccaggctacaaataag ac (SEQ ID NO: 50) | | |
| | | | | | IgG2a | | | |
| 3F6 | VH1 | GFTFNTNA (SEQ ID NO: 51) | IRSKSNNYAT (SEQ ID NO: 52) | VTEHYDYDY YVMDY (SEQ ID NO: 53) EVQLVETGGGLVQPGSLKLSCAASGFTFNTNAMNWVRQ APGKGLEWVARIRSKSNNYATYYADSVKDRFSISRDDSQ NMLSLQMNNLKTEDTAIYYCVTEHYDYDYYVMDYWGQGT SVXSPQ (SEQ ID NO: 54) Gaggtgcagcttgttgagactggtggaggattggtgca cctaaagggtcattgaaactctcatgtgcagcctgga ttcacctcaataccaatgcaatggttcgcggtccgcag gctccaggaaaggtttgagtgggttgctgcgatcaaga | | | ESVEYSGASL (SEQ ID NO: 56) | AAS (SEQ ID NO: 57) | QQSRKVPST (SEQ ID NO: 58) IVLTQSPASLAVSLGQRATISCRASESVEYSGASLMQW YQHKPGQPPKLLIYAASNVESGVPARFSGSGSGTDFSL NIHPVEEDDIAMYFCQQSRKVPSTFGGGTKLEIK (SEQ ID NO: 59) Attgtgctcaccaatccaagcttctttggctgtgtc tctgggcagagaccaccatctcctgagagccagtg aaagtgttgaatattctggcgcaagtttaatgcagtgg taccaacacaaaccaggacgaccaacaactcctcat | | 0.0010/0.0239 |

TABLE 5-continued

Antibody sequences.

| mAb[a] | V_H clan[b] | Heavy Chain Sequence | | | Light Chain Sequence[d] | | | CFU reduction/Abcess Formation P values[e] |
|---|---|---|---|---|---|---|---|---|
| | | CDR1 Amino acid sequence Nucleotide sequence | CDR2 Amino acid sequence Nucleotide sequence | CDR3 Amino acid sequence Nucleotide sequence | CDR1 Amino acid sequence Nucleotide sequence | CDR2 Amino acid sequence Nucleotide sequence | CDR3 Amino acid sequence Nucleotide sequence | |
| | | | | agtaaagtaataattatgcaacatattatgccgattca gtgaaagacaggttctccatctgcaggatgattcacaa aacatgctcctctgcaaatgaacaacttgaaaactgag gacacagccatctattactgtgcagaactatgat tacgattactactgttatgactactgggtcaaggaacc tcagtcaannctcctccagc (SEQ ID NO: 55) | | | ctatgctgcatccaacgtagaatctgggtccctgcca ggtttagtgcagttcagtggtctggacagacttcagctc aacaccctgtggaggaggatcagctatattgcaatgta ttcctgtcagcaaagtagaaggtcctcccacgttcg gaggggaccaagctggaaataaac (SEQ ID NO: 60) | | | |
| 1F10 | V_H1 | GNAFTNYL (SEQ ID NO: 61) | INPGSGIT (SEQ ID NO: 62) | SGSANWFAY (SEQ ID NO: 63) | ESVEYSGASL (SEQ ID NO: 66) | AAS (SEQ ID NO: 67) | QQSRKVPST (SEQ ID NO: 68) | 0.0299/0.0812 |
| | | KELISSKSEEKWPGTSVKVSCKASGNAFTNYLIEWIKQ RPGQGLEWIGVINPGSGITNYNEKFKGKATLTADKSSNT AYMQLSSLSSDDSAVYFCSGSANWFAYWGQGTLVTVSA (SEQ ID NO: 64) Aaggaactcatcagttccaaatctgaagaagagaaatgg cctggaacttcagtgaaggtgtcctgcaaggctctgga aacgcctcactaattatttaatagagtggataaaacag aggcctggacaggcctttagtgattggagtgaagttcaag cctgaagtggaattacttactacaatgagaagttcaag gccaaggcaacactgactgcagacaaatctccaacact gcctacatgcagctcagcagcctgtcatctgatgactct gcggtctatttctgttcaggatcggcaactggtttgct tactgggggccagggactctggtcactgtctctgca (SEQ ID NO: 65) | | | DIVLTQSPASLAVSLGQRATISCRASESVEYSGASLMQ WYQHKPGQPPKLLIYAASNVESGVPARFSGSGSGTDFS LNIHPVEEDDIAMFCQQSRKVPSTFGGGTKLEIK (SEQ ID NO: 69) Gacattgtctcaccaatctccagtcttcttggctgt gtctcttgggcagagacaagcaccatctcctgcagagcca gtgaaagtgtgaatattctggcgcaagtttaatgcag tggtaccaacacaaaccaggacagccaccaaactcct catctatgctgcatccaacgtagaatctggggtccctg ccagtttagtggcagtggtctggacagacttcagc ctcaacatccatcctgtggaggatgatattgcaat gtatttctgcagcaaagtaggaaggttcctccacgt tcggagggggaccaagctggaaataaaac (SEQ ID NO: 70) | | | |
| 6D11 | V_H1 | GNAFTNYL (SEQ ID NO: 71) | INPGSGIT (SEQ ID NO: 72) | SGSANWFAY (SEQ ID NO: 73) | ESVEYSGASL (SEQ ID NO: 76) | AAS (SEQ ID NO: 77) | QQSRKVPST (SEQ ID NO: 78) | 0.1967/0.1793 |
| | | QVQLQQSGAELVRPGTSVKVSCKASGNAFTNYLIEWIKQ RPGQGLEWIGVINPGSGITNYNEKFKGKATLTADKSSNT AYMQLSSLSSDDSAVYFCSGSANWFAYWGQGTLVTVSA (SEQ ID NO: 74) Caggtccagctgcagcagtctggagctgaactggtaagg cctggggacttcagtgaaggtgtctgcaaggctctgga aagcctcactaattatttaatagagtggataaaacag aggcctggacaggcctttagtgattggagtgaagttcaag cctgaagtggaattactaactacaatgagaagttcaag ggcaaggcaacactgactgcagacaaatctccaacact gcctacatgcagctcagcagcctgtcatctgatgactct gcggtctatttctgttcaggatcggcaactggtttgct tactgggggccagggactctggtcactgtctctgca (SEQ ID NO: 75) | | | DIVLTQSPASLAVSLGQRASISCRASESVEYSGASLMQ WYQHKPGQPPKLLIYAASNVESGVPVRFSGSGSGTDFS LNIHPVEEDDIAMFCQQSRKVPSTFGGGTKLEIK (SEQ ID NO: 79) Gacattgtctcaccaatctccagtcttcttggctgt gtccttgggcagagagccagcatctcctgcagagcca gtgaaagtgtgaatattcaggcgcaagtttaatgcag tggtaccaacacaaccaggacagccaccaaactcct catctatgctgcatccaacgtagaatctggggtccctg tcaggtttagtggcagtggtctggacagacttcagc ctcaacatccatcctgtggaggatgatattgcaat gtatttctgcagcaaagtaggaaggttcctccacgt tcggagggggaccaagctggaaataaaac (SEQ ID NO: 80) | | | |

TABLE 5-continued

Antibody sequences.

| | | Heavy Chain Sequence | | | Light Chain Sequence | | | |
|---|---|---|---|---|---|---|---|---|
| $^a$mAb | $^b V_H$ clan | CDR1 Amino acid sequence Nucleotide sequence | CDR2 Amino acid sequence Nucleotide sequence | CDR3 Amino acid sequence Nucleotide sequence | CDR1 | CDR2 | CDR3 | $^c$CFU reduction/Abcess Formation P values |

IgG2$_b$

| 3D11 | $V_H 1$ | GYSFTSYY (SEQ ID NO: 81) | IDPFNGGT (SEQ ID NO: 82) | ARYGYDGTF YAMDY (SEQ ID NO: 83) | SSVSY (SEQ ID NO: 86) | EIS (SEQ ID NO: 87) | QQWSYPFT (SEQ ID NO: 88) | 0.0010/0.0068 |

QSGPELMKPGASVKISCKASGYSFTSYYMHWVKQSHGKS
LEWIGYIDPFNGGTSYNQKFKGKATLTVDKSSSTAYMHL
SSLTSEDSAVYYCARYGYDGTFYAMDYWGQGTSVTVSS
(SEQ ID NO: 84)

Cagtctggacctgagctgatgaagcctggggcttcagtg
aagatatcctgcaaggctctgttactcattcactagc
tactacatgcactgggtgaagcagagccatggaaagagc
cttgagtggattggatatattgatccttttcaatggtggt
actactacaaccagaaattcaaggcaaggccacattg
actgtagacaaatcttccagcacagcctacatgcatctc
agcagcctgacatctgaggac
(SEQ ID NO: 85)

RIVLTQSPAITAASLGQKVTITCSASSSVSYMHWYQQK
SGTSPKPWIYEISKLASGVPARFSGSGSGTSYSLTISS
MEAEDAAIYYCQQWSYPFTFGSGTKLEIK
(SEQ ID NO: 89)

Agaattgtgctcactcagtctccagcatcacagctgc
atctctgggcaaaaggtcaccatcacctgcagtgcca
gctcaagtgtaagttacatgcactggtaccaacagaag
tcaggcacctcccccaaaccatgatttatgaaatatc
caaactggctctgagtccctcgcttcagtggca
gtgggtctgggacctcttactctcacaatcagcagc
atggaggctgaagatgctgccattatactgccagca
gtggagttatcattcacgttcggctcggggacaaagt
tggaaataaaac
(SEQ ID NO: 90)

| 5A11 | $V_H 3$ | GFTFSDYY (SEQ ID NO: 91) | ISDGGTYT (SEQ ID NO: 92) | ARDRDDYDE GPYFDY (SEQ ID NO: 93) | | | | 0.0171/0.0286 |

EVQLVESGGGLVKPGGSLKLSCAASGFTFSDYYMWVRQ
TPEKRLEWVATISDGGTYTYYPDSVKGRFTISRDNAKNN
LYLQMSSLKSEDTAMYYCARDRDDYDEGPYFDYWGQGTT
LTVSS (SEQ ID NO: 94)

Gaagtgcagctggtggagtctgggggaggcttagtgaag
cctgaggggtccctgaaactctccctgtgcagcctctga
ttcacttcagtgactattacatgtattggttcgccag
acaccggaaaagaggctgagtgggtcgcaaccattagt
gatggtggtacttacacctactaccagacagtgaag
gggcgattcaccatctccagagacaatgccaagaacaac
ctgtacctgcaaatgactctgagtctgaggacaca
gccatgtattactgtgcaagagatcgggatgatatacgac
gagggccctacttgactactgggccaaggcaccact
ctcacagtctcctcag (SEQ ID NO: 95)

TABLE 5-continued

Antibody sequences.

| [a]mAb | [b]V_H clan | Heavy Chain Sequence | | | [d]Light Chain Sequence | | | [c]CFU reduction/Abcess Formation P values |
|---|---|---|---|---|---|---|---|---|
| | | CDR1 | CDR2 | CDR3 Amino acid sequence Nucleotide sequence | CDR1 | CDR2 | CDR3 Amino acid sequence Nucleotide sequence | |
| 2F2 | V_H3 | RFTFSSYV (SEQ ID NO: 96) | IGSGGTTY (SEQ ID NO: 97) | RGRGYGFAW YFDV (SEQ ID NO: 98) VKLVESGGDLVKPGGSLKLSCAASRFTFSSYVMSWVRQT PEKRLEWVASIGSGGTTYYPDTVKGRFTISRDNARNILY LQMSSLRSDDTAMYCTRGRGYGFAWYFDVWGAGTTVTV SS (SEQ ID NO: 99) Agtgaagctgtggagtctgggggagacttagtgaagcc tggagggtccctgaaactctcctgtgcagcctctgatt cacttcagtagctcatatgtctggtcgccagac cccagagagagctggagtgggtcgcatccattggtag tggtggtaccaactactactccagacaccgtgaaggccg attcaccatctccagagaatgcagaacacatcctga ctgcaaatgagcagtctgaggtctgatgacacggccat gtattactgtacaagaggccgagggtatgtttcgcctg gtacttcgatgtctgggggcgcaggggaccacggtcaccgt ctcctcag (SEQ ID NO: 100) | SSVSY (SEQ ID NO: 101) | DTS (SEQ ID NO: 102) | QQWSSYPPT (SEQ ID NO: 103) TIVLTQSPAIMSASPGEKVTMTCSASSSVSYMYWYQQK PGSSPRLLIYDTSNLASGVPVRFSGSGSGTSYSLTISR MEAEDAATYCQQWSSYPPTFGGGTKLEIK (SEQ ID NO: 104) Acaattgtctcaccccagtctccagcaatcatgtctgc atctccagggagaagtcaccatgacctgcagtgcca gctcaagtgaagttacatgtactggtaccagcagaag ccagatcccccagacctcctgatttatgacacatc caacctgcttctggagtccctgttcgttcagtggca gtggatcaggaacttcttactcctcacaatcagcaga atggaggctgaagatgcccactttattactgccagca gtggagtagtactcaccccacgtcggagggaccca agctggaataaaac (SEQ ID NO: 105) | 0.0002/0.018 |
| 4C1 | | | | | ESVEYSGASL (SEQ ID NO: 106) | AAS (SEQ ID NO: 107) | QQSRKVPST (SEQ ID NO: 108) VLTQSPASLAVSLGQRATISCRASESVEYSGASLMQWY QHKPGQPPKLLIYAASNVESGVPARFSGSGSGTDFSLN IHPVEEDDIAMYFCQQSRKVPSTFGGGTKLEIK (SEQ ID NO: 109) Tgtgctcacccaatctccagcttctttggctgtgtctc ttgggcagagaggccaccatctcctgcagagccagtgaa agtgttgaatattctggcgcaagttaatcagtggta ccaacacaaacaggacagccaccaaactccctccatct atgtgcatccaacgtagaatctggggtccctgccagg tttagtggcagtgtctgggaacagacttcagcctcaa catccatccctgtggaggaggatgatattgcaatgtatt tctgtcagcaaagtaggaaggttccttccacgttcgga ggggggaccaagctgggaataaaaac (SEQ ID NO: 110) | 0.0228/0.0016 |
| 8D4 | V_H1 | GSTFTNHH (SEQ ID NO: 111) | LNPYNDYT (SEQ ID NO: 112) | ATITFDS (SEQ ID NO: 113) QVQLQQSGAELVRPGASVKLSCKAFGSTFTNHHINWVKQ RPGQGLDWIGYLNPYNDYTNYNQKFPKGKATLTIDKSSST AYLELSSLTSEDSAVYYCATITFDSQXQ (SEQ ID NO: 114) Caggtcccagctgcagcagtctgggggctgagctgaggtgg | | | | 0.0026/0.028 |

TABLE 5-continued

Antibody sequences.

| [a]mAb | [b]V_H clan | Heavy Chain Sequence | | | Light Chain Sequence | | | [c]CFU reduction/Abcess Formation P values |
|---|---|---|---|---|---|---|---|---|
| | | CDR1 | CDR2 | CDR3 Amino acid sequence Nucleotide sequence | CDR1 | CDR2 | CDR3 Amino acid sequence[d] Nucleotide sequence | |
| | | | | cctggggcctcagtgaagatttcctgcaaggcttttggc tccacctcacaaaccatcatataaatggtggtgaagcag aggcctggacagggcctggactggattgatatcttaat cctataatgattatactaactacaacagaagttcaag ggcaaggccacattgactactagacaaatcctccagcaca gcctatctgagctgacagcctgactttgacagccag gcagtgtattactgtgcaaccataacttttgacagccag gnncaagg (SEQ ID NO: 115) | | | | | |
| 1B10 | V_H3 | GFTFSNYD (SEQ ID NO: 116) | ISSGGTYP (SEQ ID NO: 117) | ARGGFLITTR DYYAMDY (SEQ ID NO: 118) EVKLVESGGGLVKPGGSLKLSCAASGFTFSNYDMSWVRQ TPEKRLERVATISSGGTYPYYPDSVKGRFTISRDNAENT LYLQLSSLRSEDTALYYCARGGFLITTRDYYAMDYWGQG TSVTVSS (SEQ ID NO: 119) GAAGTGAAACTGGTGGAGTCTGGGGGAGGCTTAGTGAAG CCTGGAGGGTCCCTGAAACTCTCCTGTGCAGCCTCTGGA TTCACTTTCAGTAACTATGACATGTCTTGGGTTCGCCAG ACTCCGGAGAAGAGGCTGGAGCGGGTCGCAACCATTAGT AGTGGTGGTACTTACCCCTACTATCCAGACAGTGTGAAG GGCCGTTTCACCATCTGCAATTGAGCAGTCTGAGGACACG CTGTACCTGCAATTGAGCAGTCTGAGGACACG GCCCTGTATTACTGTGCAAGAGGGGGATTTTTGATTACG ACACGGACTACTATGCTATGGACTACTGGGGTCAAGGA ACCTCAGTCACCGTCTCCTCA (SEQ ID NO: 120) | | | | 0.0113/0.0070 |
| 6B2 | | | | | ESVDYSGASL (SEQ ID NO: 121) DIVLTQSPASLAVSLGQRATISCRASESVDYSGASLMQ WYQHKPGQPPRLLIYAASNVESGVPARFSGSGSGTDFS LNIHPVEEDDIAMYFCQQSRKVPSTFGGGTKLEIK (SEQ ID NO: 124) Gacattgtgctcacccaatctccagctctcttgctgt gtctctggcagagagcccaccatcctcctgcagagcca gtgaaagttgattattctggcaagttaatgcag tggtaccaacaaccaggacagccaccagactcct catctatgctgcatccaacgtagaatctggggtccctg ccaggtttagtggcagtgggtctgggacagacttcagc | AAS (SEQ ID NO: 122) | QQSRKVPST (SEQ ID NO: 123) | 0.062/0.4119 |

TABLE 5-continued

Antibody sequences.

| | | Heavy Chain Sequence | | | Light Chain Sequence | | | |
|---|---|---|---|---|---|---|---|---|
| mAb | V_H clan | CDR1 | CDR2 | CDR3 Amino acid sequence Nucleotide sequence | CDR1 | CDR2 | CDR3 Amino acid sequence Nucleotide sequence | CFU reduction/Abcess Formation P values |

(row for 7D11 - light chain CDR3 region):
ctcaacatccatcctgtgaggaggatgatattgcaat
gtatttctgtcagcaaagtaggaaggttccttccacgt
tcggaggggggaccaagctgaaataaaac
(SEQ ID NO: 125)

P value: 0.111/0.0684

(row for 2B8 - light chain):

CDR1: ESVEYSGASL (SEQ ID NO: 126)
CDR2: AAS (SEQ ID NO: 127)
CDR3: QQSRKVPST (SEQ ID NO: 128)

FFGVSLGQRASISCRASESVEYSGASLIQWYQHKPGQP
PKLLIYAASNVESGVPVRFSGSGSGTDFSLNIHPVEED
DIAMYFCQQSRKVPSTFGGGTKLEIK
(SEQ ID NO: 129)

Cttctttggtgtctcttgggcagagagccagcatct
cctgcagagccagtgaaagtgttgaatattcaggcgca
agttaatacagtggtaccaacacaaaccaggacagcc
acccaaactcctatctatgctgcatccaaacgtagaat
ctgggtccctgcaggtttagtggcagtgggtctggg
acagacttcagcctcaacatccatcctgtggaggaga
tgatattgcaatgtatttctgtcagca
(SEQ ID NO: 130)

P value: 0.122/0.869

(row for 2C3, V_H3 - heavy chain):

CDR1: GFTFSNYD (SEQ ID NO: 131)
CDR2: ISSGGTYP (SEQ ID NO: 132)
CDR3: ARGGFLITTR DYYAMDY (SEQ ID NO: 133)

EVKLVESGGGLVKPGGSLKLSCAASGFTFSNYDMSWVRQ
TPEKRLEWVATISSGGTYPYYPDSVKGRFTISRDNAENT
LYLQLSSLRSEDTALYYCARGGFLITTRDYYAMDYWGQG
TSVTVSS (SEQ ID NO: 134)

Gaagtgaaactggtggagtctgggggaggcttagtgaag
cctggagggtccctgaaactctccctgtgcagcctga
ttcactttcagtaactatgacatgtcttggttcgccag
actccggagaaaggctggagtggtcgcaaccattagt
agtggtggtactaccctctacctccagagacagtgaag
ggccgtttcaccatccaattgacagtctgaggtctgaggacacg
ctgtacctgcaattgactgcaagagtgaggtctgaggacacg
gcctgtattactgtgctatggactactgggtcaagga
cacggactcaccgtctcctcag (SEQ ID NO: 135)

P value: 0.1318/0.204

TABLE 5-continued

Antibody sequences.

| | | Heavy Chain Sequence | | | Light Chain Sequence | | |
|---|---|---|---|---|---|---|---|
| [c]mAb | [b]V[H] clan | [a]CDR1 Amino acid sequence Nucleotide sequence | CDR2 | CDR3 | CDR1 | CDR2 | CDR3 | [e]CFU reduction/[d]Abcess Formation P values |

| | | | | | | | |
|---|---|---|---|---|---|---|---|
| 1H7 | | | | | | | | 0.1116/0.4007 |
| 4C5 | | | | | ESVEYGASL (SEQ ID NO: 136) DIVLTQSPASLAVSLGQRATISCRASESVEYYGASLMQ WYQQKSGQPPKLLIYAASNVESGVPARFSGSGTDFS LNIHPVEEDDIAMYFCQQSRKVPNTFGGGTKLEIK (SEQ ID NO: 139) Gacattgtgctcacccaatctccagcttcttggctgt gtctctaggcagagcaccatctcctgcagagcca gtgaaagtgtgaatattggcgcaagtttaatgcag tgtaccaacagaaatcaggacagcaccccaaactcct catctatgctgtcaccaactgtagaatctgggtccctg ccagtttagtgctccagtggtctgggacagacttcagc ctcaacatccaccctgtggaggaggatgatattgcaat gtatttctgtcagcaaagtaggaagttccgaacacgt tcggagggggaccaagctggaaataaaac (SEQ ID NO: 140) | AAS (SEQ ID NO: 137) | QQSRKVPNT (SEQ ID NO: 138) | 0.114/0.2489 |
| 4D5 | | | | | SSVSY (SEQ ID NO: 141) EIVLTQSPAITAASLGQKVTITCSASSSVSYMHWYHQK SGTSPKPWIYETSKLASGVPVRFSGSGSGTSYSLTISS MEAEDAAIYYCQQWSYPFTFGSGTKLEIK (SEQ ID NO: 144) | ETS (SEQ ID NO: 142) | QQWSYPFT (SEQ ID NO: 143) | 0.126/0.069 |

[a]Mouse monoclonal identifier. MAbs were purified from isolated hybridoma clones.
[b]Immunoglobulin variable heavy (IGHV) chain gene subgroup categorization based on nucleotide similarity. Mouse gene (Mus musculus) V[H] clans were compared to Homo sapiens and are represented as such. S. aureus protein A has specificity for binding to the human variable region of the Fab heavy chain V[H]3 family that represent nearly half of inherited V[H] genes and their homologues in other mammalian species.
[c]and[d]Total RNA from MAb hybridoma cells was isolated via standard protocol. cDNA was synthesized and amplified by RT-PCR with Ig Primer sets designed for amplification from Ig conserved regions adjacent to the V[H] and V[L] hypervariable complementarity defining regions (CDRs). Positive products were sequenced and analyzed using IMGT vquest (http://imgt.cines.fr/IMGT_vquest). Amino acid, nucleotide, and specific CDR sequences are designated, with CDRs bolded and underlined within the full amino acid sequence.
[e]P values indicating significant reduction (P < 0.05) in CFU following S. aureus renal abscess challenge in mice.
[f]P values indicating significant reduction (P < 0.05) in abscesses in kidneys as determined by histopathological analysis.

Example 2

Materials and Methods

Bacterial Strains and Growth Conditions.

S. aureus strains Newman and MW2 were grown in tryptic soy broth (TSB) at 37° C. Escherichia coli strains DH5α and BL21 (DE3) were grown in Luria-Bertani (LB) broth with 100 μg·ml-1 ampicillin at 37° C.

Monoclonal Antibodies.

Mouse monoclonal antibodies were generated by the conventional method (Köhler, G., and C. Milstein. 1975). Briefly, BALB/c mice (8 week old, female, Jackson Laboratory) were immunized by intraperitoneal injection with 100 μg purified SpA$_{KKAA}$ emulsified 1:1 with Complete Freund's Adjuvant (CFA, DIFCO). On days 21 and 42, mice were boosted by intraperitoneal injection with 100 μg of the same antigen emulsified 1:1 with Incomplete Freund's Adjuvant (IFA, DIFCO). On days 31 and 52, mice were bled and serum samples screened by ELISA for specific antibodies. Seventy-nine days following initial immunization, mice that demonstrated strong antigen-immunoreactivity by ELISA were boosted with 25 μg of the same antigen. Three days later, splenocytes were harvested and fused with the mouse myeloma cell line SP2/mIL-6, an interleukin 6 secreting derivative of the SP2/0 myeloma cell line. Supernatants from resulting hybridomas were screened by ELISA and antigen-specific clones were further subcloned by limiting dilution to yield monoclonal antibody-secreting hybridomas arising from single cells. Antibodies were purified from the spent culture supernatant of cell lines. Spa27 monoclonal antibody was purchased from Sigma. Hybridoma cell line 358A76.1.1 was purchased from American Type Culture Collection (ATCC accession number PTA-7938) and expanded at the Fitch monoclonal antibody facility (University of Chicago).

Purification of Recombinant Proteins.

Polypeptides derived from the amino acid sequence of the SpA-E$_{KKAA}$ domain were synthesized by CPC Scientific Inc (Sunnyvale, USA). Lyophilized peptide samples were solubilized using either distilled water or dimethyl sulfoxide (DMSO), then aliquoted and frozen at −80° C. The use of plasmids for wild-type SpA and SpA$_{KKAA}$ has been previously described (Kim et al., 2010a). Oligonucleotides for the synthesis of SpA$_{KK}$ ($Q^9K$, $Q^{10}K$ substitutions in each of the five IgBDs), SpA$_{AA}$ ($D^{36}A$, $D^{37}A$ substitutions in each of the five IgBDs), individual IgBDs (E, D, A, B and C) of SpA$_{KKAA}$ were synthesized by Integrated DNA Technologies, Inc (USA). PCR products of SpA$_{KKAA}$ variants were cloned into the pET15b vector generating N-terminal His$_6$-tagged recombinant proteins. The coding sequence of Sbi$_{1-4}$ was PCR amplified with two primers, 5'-AAAAAAGCTAGCTGGTCTCATCCTCAATTT-GAGAAGACGCAACAAACTTCAACTAA G-3' (SEQ ID NO:8) and 5'-AAAAAACTCGAGTTTCCAGAATGA-TAATAAATTAC-3' (SEQ ID NO:9) from S. aureus Newman chromosomal DNA with engineered N-terminal Strep tag (WSHPQFEK (SEQ ID NO:10)). PCR product of Sbi$_{1-4}$ was cloned into pET24b vector generating C-terminal His$_6$-tagged recombinant protein with engineered N-terminal Strep tag (WSHPQFEK (SEQ ID NO:10)). All plasmids were transformed into BL21(DE3) for affinity purification. Overnight cultures of recombinant E. coli strains were diluted 1:100 into fresh media and grown at 37° C. to A$_{600}$ 0.5, at which point cultures were induced with 1 mM isopropyl β-D-1-thiogalatopyranoside (IPTG) and grown for an additional three hours. Bacterial cells were sedimented by centrifugation, suspended in column buffer (50 mM Tris-HCl (pH 7.5), 150 mM NaCl) and disrupted with a French pressure cell at 14,000 psi. Lysates were cleared of membrane and insoluble components by ultracentrifugation at 40,000×g. Proteins in the cleared lysate were subjected to nickel-nitrilotriacetic acid (Ni-NTA) affinity chromatography. Proteins were eluted in column buffer containing successively higher concentrations of imidazole (100-500 mM). Protein concentrations were determined by bicinchonic acid (BCA) assay (Thermo Scientific).

Enzyme Linked Immunosorbent Assay.

To determine SpA specific serum IgG, affinity purified SpA$_{KKAA}$ was used to coat ELISA plates (NUNC Maxisorp) at 1 μg·ml$^{-1}$ in 0.1 M carbonate buffer (pH 9.5 at 4° C.) overnight. The following day, plates were blocked and incubated with dilutions of hyperimmune sera and developed using OptEIA reagent (BD Biosciences). For the determination of binding affinity of SpA-specific mAbs, ELISA plates were coated with affinity purified individual immunoglobulin binding domains or synthetic peptides (H1, H2, H3, H1+3 and H2+3) whose sequences were derived from the sequence of SpA-E$_{KKAA}$. Peptides were used for plate coating at a concentration of 100 nM in 0.1 M carbonate buffer, pH 9.5 at 4° C. overnight. The following day, plates were blocked with 1% BSA solution in PBS-T and incubated with variable concentrations of SpA-specific mAbs. To determine the avidity of specific mAbs, antibody-antigen interactions were perturbed with increasing concentration (0-4 M) of ammonium thiocyanate. For SpA and Sbi binding assays, affinity purified SpA and Sbi were coated onto ELISA plate at 1 μg·ml$^{-1}$ in 0.1 M carbonate buffer (pH 9.5 at 4° C.) overnight. The following day, plates were blocked and incubated with dilutions of peroxidase-conjugated human IgG, Fc and F(ab)$_2$ (The Jackson Laboratory) or dilutions of isotype control antibodies and SpA$_{KKAA}$-specific mAbs; assays were developed using OptEIA reagent. To measure the inhibition of immune association between human IgG and SpA, plates were incubated with either 20 μg·ml-1 isotype control antibodies or SpA$_{KKAA}$-specific mAbs prior to ligand binding. For competition assay, plates were coated with 10 ng·ml$^{-1}$ SpA$_{KKAA}$ in 0.1 M carbonate buffer (pH 9.5) at 4° C. overnight. The following day, plates were blocked and incubated with 30 μg·ml$^{-1}$ of isotype control antibodies or SpA$_{KKAA}$-specific mAbs prior to the incubation with HRP-conjugated SpA-specific mAbs (Innova Biosciences) or human IgG at a final concentration of 100-200 ng·ml$^{-1}$.

Mouse Renal Abscess Model.

Affinity purified antibodies in PBS were injected at a concentration 5, 15, 20, or 50 mg·kg$^{-1}$ of experimental animal weight into the peritoneal cavity of BALB/c mice (6 week old, female, Charles River Laboratories) 4-24 hours prior to challenge with S. aureus. Overnight cultures of S. aureus strains were diluted 1:100 into fresh TSB and grown for 2 hours at 37° C. Staphylococci were sedimented, washed and suspended in PBS to the desired bacterial concentration. Inocula were quantified by spreading sample aliquots on TSA and enumerating the colonies that formed upon incubation. BALB/c mice were anesthetized via intraperitoneal injection with 100 mg·ml$^{-1}$ ketamine and 20 mg·ml$^{-1}$ xylazine per kilogram of body weight. Mice were infected by injection with 1×10$^7$ CFU of S. aureus Newman or 5×10$^6$ CFU of S. aureus USA300 (LAC) or USA400 (MW2) into the periorbital venous sinus of the right eye. On day 4 or 15 following challenge, mice were killed by CO$_2$ inhalation. Both kidneys were removed, and the staphylococcal load in one organ was analyzed by homogenizing renal tissue with PBS, 0.1% Triton X-100. Serial dilutions of homogenate were spread on TSA and incubated for colony formation. The remaining organ was examined by histopathology. Briefly, kidneys were fixed in 10% formalin for 24 hours at room temperature. Tissues were embedded in paraffin, thin-sectioned, stained with hematoxylin-eosin, and inspected by light microscopy to enumerate abscess lesions. Immune serum samples collected at 15 days post infection were examined by immunoblotting against 14 affinity purified staphylococcal antigens immobilized onto nitrocellulose membrane at 2 μg. Signal intensities were quantified as previously described (Kim et al., 2010b). All mouse experiments were performed in accordance with the institutional guidelines following experimental protocol review and approval by the Institutional Biosafety Committee (IBC) and the Institutional Animal Care and Use Committee (IACUC) at the University of Chicago.

Staphylococcal Survival in Blood.

Whole blood was collected from BALB/c mice by cardiac puncture and coagulation inhibited with 10 μg·ml$^{-1}$ lepirudin. 50 μl of 5×10$^5$ CFU·ml$^{-1}$ of S. aureus Newman were mixed with 950 μl of mouse blood in the presence of 2 μg·ml$^{-1}$ of mAbs. Samples were incubated at 37° C. with slow rotation for 30 minutes and then incubated on ice with 1% saponin/PBS. For human blood studies, 50 μl of 5×10$^6$ CFU ml$^{-1}$ of S. aureus MW2 were mixed with 950 μl of freshly drawn human blood in the presence of 10 μg·ml$^{-1}$ of mAbs. The tubes were incubated at 37° C. with slow rotation for 120 minutes. Aliquots were incubated on ice with 1% saponin/PBS to lyse blood cells. Dilutions of staphylococci were plated on agar for colony formation. Experiments with blood from human volunteers were performed with protocols that had been reviewed, approved, and supervised by the University of Chicago's Institutional Review Board (IRB).

SpA-Specific Serum IgG.

BALB/c mice were injected into the peritoneum with 20 μg affinity purified SpA variants in the presence of 85 μg mAb 3F6 or its isotype control at day 0 and 11. At day 21, whole blood was collected from BALB/c mice to obtain hyperimmune sera.

Measuring the Abundance SpA in Circulation.

Passively immunized BALB/c mice were injected into the peritoneum with 200 μg affinity purified wild-type SpA. At indicated time intervals, whole blood was collected from BALB/c mice with 10 μg·ml$^{-1}$ of lepirudin anticoagulant. All samples were kept on ice with 1% saponin/PBS for 10 minutes. Lysed samples were then diluted in 1:10 PBS and mixed with SDS-PAGE sample buffer in 1:1. Samples were boiled for 5 minutes at 90° C. prior to SDS-PAGE gel electrophoresis. Samples were transferred to PDVF and analyzed by immunoblotting with affinity-purified rabbit α-SpA$_{KKAA}$ antibody.

Sbi Consumption Assay.

Overnight cultures of S. aureus Newman were diluted 1:100 into fresh TSB, grown for 2 hours and A600 adjusted to 0.4 (1×10$^8$ CFU·ml$^{-1}$) with pre-chilled TSB. Cells were washed and incubated with either 100 μl of isotype control or mAb 3F6 at a final concentration of 100 μg·ml$^{-1}$ for an hour at 4° C. Following incubation, staphylococci were washed with pre-chilled TSB and incubated with 2 μg of affinity-purified wild-type Sbi for one hour at 4° C. Staphylococci were sedimented by centrifugation at 13,000×g for one minute, supernatants were removed and mixed with sample buffer (1:1). Samples were boiled for 5 minutes at 90° C. prior to SDS-PAGE gel electrophoresis. Samples were electrotransferred to PDVF membrane and analyzed by immunoblotting with affinity-purified rabbit α-SpA$_{KKAA}$ antibody.

Sequencing of Monoclonal Antibodies.

Total RNA samples from hybridoma cells were isolated using a standardized protocol. Briefly, 1.4×10$^7$ hybridoma cells cultured in DMEM-10 medium with 10% FBS were washed with PBS, sedimented by centrifugation and lysed in TRIzol (Invitrogen). Samples were mixed with 20% chloroform and incubated at room temperature for three minutes and centrifuged at 10,000×g for fifteen minutes at 4° C. RNAs in the aqueous layer were removed and washed with 70% isopropanol. RNA was sedimented by centrifugation and washed with 75% diethylpyrocarbonate (DEPC)-ethanol. Pellets were dried and RNA dissolved in DEPC. cDNA was synthesized with the cDNA synthesis kit (Novagen) and PCR amplified using the PCR Reagent System (Stratagene), independent primers (5 pmol each) and a mouse variable heavy and light chain specific primer set (Novagen). PCR products were sequenced and analyzed using IMGT Vquest (available at imgt.cines.fr/IMGT_vquest).

Statistical Analysis.

Bacterial loads and number of abscesses in the experimental animal model for S. aureus infection were analyzed with the two-tailed Mann-Whitney test to measure statistical significance. Unpaired two-tailed Student's t-tests were performed to analyze the statistical significance of ELISA data, immunoblotting signals, and ex vivo blood survival data. All data were analyzed by Prism (GraphPad Software, Inc.) and P values less than 0.05 were deemed significant.

TABLE 7

(Variable Light chain CDR percent identity matrix)

| | | | | | | | | | | | | | |
|---|---|---|---|---|---|---|---|---|---|---|---|---|---|
| 1: | 5A10 | 100 | 29 | 29 | 29 | 41 | 41 | 41 | 69 | 100 | 41 | 41 | 41 | 35 |
| 2: | 8E2 | 29 | 100 | 17 | 56 | 28 | 28 | 28 | 25 | 29 | 28 | 28 | 28 | 28 |
| 3: | 3A6 | 29 | 17 | 100 | 22 | 32 | 32 | 32 | 31 | 29 | 32 | 32 | 32 | 32 |
| 4: | 7E2 | 29 | 56 | 22 | 100 | 28 | 28 | 28 | 19 | 29 | 28 | 28 | 28 | 28 |
| 5: | 3F6 | 41 | 28 | 32 | 28 | 100 | 100 | 100 | 38 | 41 | 100 | 95 | 100 | 91 |
| 6: | 1F10 | 41 | 28 | 32 | 28 | 100 | 100 | 100 | 38 | 41 | 100 | 95 | 100 | 91 |
| 7: | 6D11 | 41 | 28 | 32 | 28 | 100 | 100 | 100 | 38 | 41 | 100 | 95 | 100 | 91 |
| 8: | 3D11 | 69 | 25 | 31 | 19 | 38 | 38 | 38 | 100 | 69 | 38 | 38 | 38 | 31 |
| 9: | 2F2 | 100 | 29 | 29 | 29 | 41 | 41 | 41 | 69 | 100 | 41 | 41 | 41 | 35 |
| 10: | 4C1 | 41 | 28 | 32 | 28 | 100 | 100 | 100 | 38 | 41 | 100 | 95 | 100 | 91 |
| 11: | 6B2 | 41 | 28 | 32 | 28 | 95 | 95 | 95 | 38 | 41 | 95 | 100 | 95 | 86 |
| 12: | 2B8 | 41 | 28 | 32 | 28 | 100 | 100 | 100 | 38 | 41 | 100 | 95 | 100 | 91 |
| 13: | 4C5 | 35 | 28 | 32 | 28 | 91 | 91 | 91 | 31 | 35 | 91 | 86 | 91 | 100 |

TABLE 8

(Variable Heavy chain CDR percent identity matrix)

|    |      | 5A10 | 1B10 | 2C3 | 8E2 | 3A6 | 7E2 | 3F6 | 1F10 | 6D11 | 3D11 | 5A11 | 2F2 | 8D4 |
|----|------|------|------|-----|-----|-----|-----|-----|------|------|------|------|-----|-----|
| 1: | 5A10 | 100  | 97   | 97  | 42  | 24  | 27  | 38  | 32   | 32   | 40   | 45   | 38  | 26  |
| 2: | 1B10 | 97   | 100  | 100 | 45  | 24  | 31  | 41  | 28   | 28   | 40   | 48   | 41  | 30  |
| 3: | 2C3  | 97   | 100  | 100 | 45  | 24  | 31  | 41  | 28   | 28   | 40   | 48   | 41  | 30  |
| 4: | 8E2  | 42   | 45   | 45  | 100 | 33  | 38  | 33  | 40   | 40   | 53   | 28   | 25  | 30  |
| 5: | 3A6  | 24   | 24   | 24  | 33  | 100 | 62  | 19  | 30   | 30   | 33   | 29   | 14  | 24  |
| 6: | 7E2  | 27   | 31   | 31  | 38  | 62  | 100 | 24  | 32   | 32   | 32   | 31   | 24  | 26  |
| 7: | 3F6  | 38   | 41   | 41  | 33  | 19  | 24  | 100 | 17   | 17   | 28   | 30   | 24  | 27  |
| 8: | 1F10 | 32   | 28   | 28  | 40  | 30  | 32  | 17  | 100  | 100  | 36   | 32   | 25  | 33  |
| 9: | 6D11 | 32   | 28   | 28  | 40  | 30  | 32  | 17  | 100  | 100  | 36   | 32   | 25  | 33  |
| 10:| 3D11 | 40   | 40   | 40  | 53  | 33  | 32  | 28  | 36   | 36   | 100  | 32   | 22  | 35  |
| 11:| 5A11 | 45   | 48   | 48  | 28  | 29  | 31  | 30  | 32   | 32   | 32   | 100  | 41  | 30  |
| 12:| 2F2  | 38   | 41   | 41  | 25  | 14  | 24  | 24  | 25   | 25   | 22   | 41   | 100 | 9   |
| 13:| 8D4  | 26   | 30   | 30  | 30  | 24  | 26  | 27  | 33   | 33   | 35   | 30   | 9   | 100 |

TABLE 9

(Variable Light and Heavy chain CDR percent identity)

|    |      | 5A10 | 8E2 | 3A6 | 7E2 | 3F6 | 1F10 | 6D11 | 3D11 | 2F2 |
|----|------|------|-----|-----|-----|-----|------|------|------|-----|
| 1: | 5A10 | 100  | 38  | 26  | 28  | 39  | 33   | 33   | 54   | 61  |
| 2: | 8E2  | 38   | 100 | 26  | 45  | 31  | 33   | 33   | 46   | 27  |
| 3: | 3A6  | 26   | 26  | 100 | 44  | 26  | 30   | 30   | 32   | 21  |
| 4: | 7E2  | 28   | 45  | 44  | 100 | 25  | 29   | 29   | 29   | 26  |
| 5: | 3F6  | 39   | 31  | 26  | 25  | 100 | 57   | 57   | 33   | 30  |
| 6: | 1F10 | 33   | 33  | 30  | 29  | 57  | 100  | 100  | 38   | 34  |
| 7: | 6D11 | 33   | 33  | 30  | 29  | 57  | 100  | 100  | 38   | 34  |
| 8: | 3D11 | 54   | 46  | 32  | 29  | 33  | 38   | 38   | 100  | 44  |
| 9: | 2F2  | 61   | 27  | 21  | 26  | 30  | 34   | 34   | 44   | 100 |

TABLE 10

(Variable Light Chain CDR1 percent identity matrix)

|    |      | 5A10 | 8E2 | 3A6 | 7E2 | 3F6 | 1F10 | 6D11 | 3D11 | 2F2 | 4C1 | 6B2 | 2B8 | 4C5 |
|----|------|------|-----|-----|-----|-----|------|------|------|-----|-----|-----|-----|-----|
| 1: | 5A10 | 100  | 0   | 40  | 0   | 60  | 60   | 60   | 100  | 100 | 60  | 60  | 60  | 60  |
| 2: | 8E2  | 0    | 100 | 17  | 50  | 17  | 17   | 17   | 0    | 0   | 17  | 17  | 17  | 33  |
| 3: | 3A6  | 40   | 17  | 100 | 17  | 20  | 20   | 20   | 40   | 40  | 20  | 20  | 20  | 20  |
| 4: | 7E2  | 0    | 50  | 17  | 100 | 17  | 17   | 17   | 0    | 0   | 17  | 17  | 17  | 33  |
| 5: | 3F6  | 60   | 17  | 20  | 17  | 100 | 100  | 100  | 60   | 60  | 100 | 90  | 100 | 90  |
| 6: | 1F10 | 60   | 17  | 20  | 17  | 100 | 100  | 100  | 60   | 60  | 100 | 90  | 100 | 90  |
| 7: | 6D11 | 60   | 17  | 20  | 17  | 100 | 100  | 100  | 60   | 60  | 100 | 90  | 100 | 90  |
| 8: | 3D11 | 100  | 0   | 40  | 0   | 60  | 60   | 60   | 100  | 100 | 60  | 60  | 60  | 60  |
| 9: | 2F2  | 100  | 0   | 40  | 0   | 60  | 60   | 60   | 100  | 100 | 60  | 60  | 60  | 60  |
| 10:| 4C1  | 60   | 17  | 20  | 17  | 100 | 100  | 100  | 60   | 60  | 100 | 90  | 100 | 90  |
| 11:| 6B2  | 60   | 17  | 20  | 17  | 90  | 90   | 90   | 60   | 60  | 90  | 100 | 90  | 80  |
| 12:| 2B8  | 60   | 17  | 20  | 17  | 100 | 100  | 100  | 60   | 60  | 100 | 90  | 100 | 90  |
| 13:| 4C5  | 60   | 33  | 20  | 33  | 90  | 90   | 90   | 60   | 60  | 90  | 80  | 90  | 100 |

TABLE 11

(Variable Light Chain CDR2 percent identity matrix)

|    |      | 5A10 | 8E2 | 3A6 | 7E2 | 3F6 | 1F10 | 6D11 | 3D11 | 2F2 | 4C1 | 6B2 | 2B8 | 4C5 |
|----|------|------|-----|-----|-----|-----|------|------|------|-----|-----|-----|-----|-----|
| 1: | 5A10 | 100  | 0   | 33  | 0   | 33  | 33   | 33   | 33   | 100 | 33  | 33  | 33  | 33  |
| 2: | 8E2  | 0    | 100 | 0   | 67  | 33  | 33   | 33   | 0    | 0   | 33  | 33  | 33  | 33  |
| 3: | 3A6  | 33   | 0   | 100 | 0   | 33  | 33   | 33   | 33   | 33  | 33  | 33  | 33  | 33  |
| 4: | 7E2  | 0    | 67  | 0   | 100 | 33  | 33   | 33   | 0    | 0   | 33  | 33  | 33  | 33  |
| 5: | 3F6  | 33   | 33  | 33  | 33  | 100 | 100  | 100  | 33   | 33  | 100 | 100 | 100 | 100 |
| 6: | 1F10 | 33   | 33  | 33  | 33  | 100 | 100  | 100  | 33   | 33  | 100 | 100 | 100 | 100 |
| 7: | 6D11 | 33   | 33  | 33  | 33  | 100 | 100  | 100  | 33   | 33  | 100 | 100 | 100 | 100 |
| 8: | 3D11 | 33   | 0   | 33  | 0   | 33  | 33   | 33   | 100  | 33  | 33  | 33  | 33  | 33  |
| 9: | 2F2  | 100  | 0   | 33  | 0   | 33  | 33   | 33   | 33   | 100 | 33  | 33  | 33  | 33  |
| 10:| 4C1  | 33   | 33  | 33  | 33  | 100 | 100  | 100  | 33   | 33  | 100 | 100 | 100 | 100 |
| 11:| 6B2  | 33   | 33  | 33  | 33  | 100 | 100  | 100  | 33   | 33  | 100 | 100 | 100 | 100 |

TABLE 11-continued (Variable Light Chain CDR2 percent identity matrix)

|   |     | 5A10 | 8E2 | 3A6 | 7E2 | 3F6 | 1F10 | 6D11 | 3D11 | 2F2 | 4C1 | 6B2 | 2B8 | 4C5 |
|---|-----|------|-----|-----|-----|-----|------|------|------|-----|-----|-----|-----|-----|
| 12: | 2B8 | 33 | 33 | 33 | 33 | 100 | 100 | 100 | 33 | 33 | 100 | 100 | 100 | 100 |
| 13: | 4C5 | 33 | 33 | 33 | 33 | 100 | 100 | 100 | 33 | 33 | 100 | 100 | 100 | 100 |

TABLE 12

(Variable Light Chain CDR3 percent identity matrix)

|   |     | 5A10 | 8E2 | 3A6 | 7E2 | 3F6 | 1F10 | 6D11 | 3D11 | 2F2 | 4C1 | 6B2 | 2B8 | 4C5 |
|---|-----|------|-----|-----|-----|-----|------|------|------|-----|-----|-----|-----|-----|
| 1: | 5A10 | 100 | 25 | 33 | 50 | 44 | 44 | 44 | 88 | 100 | 44 | 44 | 44 | 44 |
| 2: | 8E2  | 25 | 100 | 25 | 56 | 25 | 25 | 25 | 25 | 25 | 25 | 25 | 25 | 25 |
| 3: | 3A6  | 33 | 25 | 100 | 25 | 44 | 44 | 44 | 38 | 33 | 44 | 44 | 44 | 44 |
| 4: | 7E2  | 50 | 56 | 25 | 100 | 25 | 25 | 25 | 50 | 50 | 25 | 25 | 25 | 25 |
| 5: | 3F6  | 44 | 25 | 44 | 25 | 100 | 100 | 100 | 50 | 44 | 100 | 100 | 100 | 89 |
| 6: | 1F10 | 44 | 25 | 44 | 25 | 100 | 100 | 100 | 50 | 44 | 100 | 100 | 100 | 89 |
| 7: | 6D11 | 44 | 25 | 44 | 25 | 100 | 100 | 100 | 50 | 44 | 100 | 100 | 100 | 89 |
| 8: | 3D11 | 88 | 25 | 38 | 50 | 50 | 50 | 50 | 100 | 88 | 50 | 50 | 50 | 50 |
| 9: | 2F2  | 100 | 25 | 33 | 50 | 44 | 44 | 44 | 88 | 100 | 44 | 44 | 44 | 44 |
| 10: | 4C1 | 44 | 25 | 44 | 25 | 100 | 100 | 100 | 50 | 44 | 100 | 100 | 100 | 89 |
| 11: | 6B2 | 44 | 25 | 44 | 25 | 100 | 100 | 100 | 50 | 44 | 100 | 100 | 100 | 89 |
| 12: | 2B8 | 44 | 25 | 44 | 25 | 100 | 100 | 100 | 50 | 44 | 100 | 100 | 100 | 89 |
| 13: | 4C5 | 44 | 25 | 44 | 25 | 89 | 89 | 89 | 50 | 44 | 89 | 89 | 89 | 100 |

TABLE 13

(Variable Heavy Chain CDR1 percent identity matrix)

|   |     | 5A10 | 8E2 | 3A6 | 7E2 | 3F6 | 1F10 | 6D11 | 3D11 | 2F2 | 1B10 | 2C3 | 5A11 | 8D4 |
|---|-----|------|-----|-----|-----|-----|------|------|------|-----|------|-----|------|-----|
| 1: | 5A10 | 100 | 38 | 38 | 38 | 38 | 62 | 62 | 38 | 50 | 88 | 88 | 62 | 38 |
| 2: | 8E2  | 38 | 100 | 75 | 88 | 38 | 50 | 50 | 62 | 38 | 50 | 50 | 50 | 50 |
| 3: | 3A6  | 38 | 75 | 100 | 88 | 25 | 50 | 50 | 62 | 25 | 38 | 38 | 50 | 38 |
| 4: | 7E2  | 38 | 88 | 88 | 100 | 38 | 50 | 50 | 62 | 38 | 50 | 50 | 62 | 50 |
| 5: | 3F6  | 38 | 38 | 25 | 38 | 100 | 25 | 25 | 25 | 38 | 50 | 50 | 50 | 38 |
| 6: | 1F10 | 62 | 50 | 50 | 50 | 25 | 100 | 100 | 50 | 25 | 50 | 50 | 38 | 50 |
| 7: | 6D11 | 62 | 50 | 50 | 50 | 25 | 100 | 100 | 50 | 25 | 50 | 50 | 38 | 50 |
| 8: | 3D11 | 38 | 62 | 62 | 62 | 25 | 50 | 50 | 100 | 38 | 38 | 38 | 50 | 38 |
| 9: | 2F2  | 50 | 38 | 25 | 38 | 38 | 25 | 25 | 38 | 100 | 62 | 62 | 62 | 25 |
| 10: | 1B10 | 88 | 50 | 38 | 50 | 50 | 50 | 50 | 38 | 62 | 100 | 100 | 75 | 50 |
| 11: | 2C3  | 88 | 50 | 38 | 50 | 50 | 50 | 50 | 38 | 62 | 100 | 100 | 75 | 50 |
| 12: | 5A11 | 62 | 50 | 50 | 62 | 50 | 38 | 38 | 50 | 62 | 75 | 75 | 100 | 38 |
| 13: | 8D4  | 38 | 50 | 38 | 50 | 38 | 50 | 50 | 38 | 25 | 50 | 50 | 38 | 100 |

TABLE 14

(Variable Heavy Chain CDR2 percent identity matrix)

|   |     | 5A10 | 8E2 | 3A6 | 7E2 | 3F6 | 1F10 | 6D11 | 3D11 | 2F2 | 1B10 | 2C3 | 5A11 | 8D4 |
|---|-----|------|-----|-----|-----|-----|------|------|------|-----|------|-----|------|-----|
| 1: | 5A10 | 100 | 25 | 12 | 25 | 25 | 25 | 25 | 20 | 62 | 100 | 100 | 75 | 20 |
| 2: | 8E2  | 25 | 100 | 0 | 12 | 22 | 50 | 50 | 40 | 12 | 25 | 25 | 25 | 20 |
| 3: | 3A6  | 12 | 0 | 100 | 62 | 12 | 25 | 25 | 40 | 12 | 12 | 12 | 12 | 20 |
| 4: | 7E2  | 25 | 12 | 62 | 100 | 12 | 38 | 38 | 40 | 12 | 25 | 25 | 12 | 20 |
| 5: | 3F6  | 25 | 22 | 12 | 12 | 100 | 25 | 25 | 0 | 38 | 25 | 25 | 12 | 0 |
| 6: | 1F10 | 25 | 50 | 25 | 38 | 25 | 100 | 100 | 40 | 25 | 25 | 25 | 38 | 40 |
| 7: | 6D11 | 25 | 50 | 25 | 38 | 25 | 100 | 100 | 40 | 25 | 25 | 25 | 38 | 40 |
| 8: | 3D11 | 20 | 40 | 40 | 40 | 0 | 40 | 40 | 100 | 20 | 20 | 20 | 20 | 33 |
| 9: | 2F2  | 62 | 12 | 12 | 12 | 38 | 25 | 25 | 20 | 100 | 62 | 62 | 50 | 0 |
| 10: | 1B10 | 100 | 25 | 12 | 25 | 25 | 25 | 25 | 20 | 62 | 100 | 100 | 75 | 20 |
| 11: | 2C3  | 100 | 25 | 12 | 25 | 25 | 25 | 25 | 20 | 62 | 100 | 100 | 75 | 20 |
| 12: | 5A11 | 75 | 25 | 12 | 12 | 12 | 38 | 38 | 20 | 50 | 75 | 75 | 100 | 60 |
| 13: | 8D4  | 20 | 20 | 20 | 20 | 0 | 40 | 40 | 33 | 0 | 20 | 20 | 60 | 100 |

TABLE 15

(Variable Heavy Chain CDR3 percent identity matrix)

|   | | 5A10 | 8E2 | 3A6 | 7E2 | 3F6 | 1F10 | 6D11 | 3D11 | 2F2 | 1B10 | 2C3 | 5A11 | 8D4 |
|---|---|---|---|---|---|---|---|---|---|---|---|---|---|---|
| 1: | 5A10 | 100 | 42 | 0 | 12 | 43 | 0 | 0 | 36 | 15 | 100 | 100 | 12 | 0 |
| 2: | 8E2 | 42 | 100 | 0 | 10 | 44 | 33 | 33 | 67 | 25 | 42 | 42 | 30 | 0 |
| 3: | 3A6 | 0 | 0 | 100 | 0 | 40 | 0 | 0 | 20 | 20 | 0 | 0 | 0 | 50 |
| 4: | 7E2 | 12 | 10 | 0 | 100 | 20 | 33 | 33 | 20 | 0 | 12 | 12 | 20 | 0 |
| 5: | 3F6 | 43 | 44 | 40 | 20 | 100 | 20 | 20 | 43 | 9 | 43 | 43 | 20 | 29 |
| 6: | 1F10 | 0 | 33 | 0 | 33 | 20 | 100 | 100 | 20 | 0 | 0 | 0 | 22 | 0 |
| 7: | 6D11 | 0 | 33 | 0 | 33 | 20 | 100 | 100 | 20 | 0 | 0 | 0 | 22 | 0 |
| 8: | 3D11 | 36 | 67 | 20 | 20 | 43 | 20 | 20 | 100 | 27 | 36 | 36 | 20 | 29 |
| 9: | 2F2 | 15 | 25 | 20 | 0 | 9 | 0 | 0 | 27 | 100 | 15 | 15 | 14 | 14 |
| 10: | 1B10 | 100 | 42 | 0 | 12 | 43 | 0 | 0 | 36 | 15 | 100 | 100 | 12 | 0 |
| 11: | 2C3 | 100 | 42 | 0 | 12 | 43 | 0 | 0 | 36 | 15 | 100 | 100 | 12 | 0 |
| 12: | 5A11 | 12 | 30 | 0 | 20 | 20 | 22 | 22 | 20 | 14 | 12 | 12 | 100 | 0 |
| 13: | 8D4 | 0 | 0 | 50 | 0 | 29 | 0 | 0 | 29 | 14 | 0 | 0 | 0 | 100 |

TABLE 16

List of antibodies in which the indicated CDR has 40% or greater sequence identity to the indicated reference antibody.

5A10 40% or greater identity with reference to 5A10:

| L | CDR1 | 3A6, 3F6, 1F10, 6D11, 3D11, 2F2, 4C1, 6B2, 2B8, 4C5 |
| L | CDR2 | 2F2 |
| L | CDR3 | 7E2, 3F6, 1F10, 6D11, 3D11, 2F2, 4C1, 6B2, 2B8, 4C5 |
| H | CDR1 | 1F10, 6D11, 2F2, 1B10, 2C3, 5A11 |
| H | CDR2 | 2F2, 1B10, 2C3, 5A11 |
| H | CDR3 | 8E2, 3F6, 1B10, 2C3 |

3F6 40% or greater identity with reference to 3F6:

| L | CDR1 | 5A10, 1F10, 6D11, 3D11, 2F2, 4C1, 6B2, 2B8, 4C5 |
| L | CDR2 | 1F10, 6D11, 4C1, 6B2, 2B8, 4C5 |
| L | CDR3 | 5A10, 3A6, 1F10, 6D11, 3D11, 2F2, 4C1, 6B2, 2B8, 4C5 |
| H | CDR1 | 1B10, 2C3, 5A11 |
| H | CDR2 | — |
| H | CDR3 | 5A10, 8E2, 3A6, 3D11, 1B10, 2C3 |

3D11 40% or greater identity with reference to 3D11:

| L | CDR1 | 5A10, 3A6, 3F6, 1F10, 6D11, 2F2, 4C1, 6B2, 2B8, 4C5 |
| L | CDR2 | — |
| L | CDR3 | 5A10, 7E2, 3F6, 1F10, 6D11, 2F2, 4C1, 6B2, 2B8, 4C5 |
| H | CDR1 | 8E2, 3A6, 7E2, 1F10, 6D11, 5A11 |
| H | CDR2 | 8E2, 3A6, 7E2, 1F10, 6D11 |
| H | CDR3 | 8E2, 3F6 |

TABLE 17

(Consensus sequences for the CDRs of antibodies with 40% or greater identity with respect to 3F6)

| Light Chain CDR1 | 100% | ESVEYSGASL (SEQ ID NO: 145) |
| | 90% | ESV[E, D]YSGASL (SEQ ID NO: 146) |
| | 60% | [E, —][S, —][V, —][E, —][Y, —]S[G, S][A, V]S[L, Y] (SEQ ID NO: 147) |
| | Overall consensus | [E, S]SV[E, D, S]Y[S, Y]GASL (SEQ ID NO: 148) |
| Light Chain CDR2 | 100% | AAS (SEQ ID NO: 149) |
| Light Chain CDR3 | 100% | QQSRKVPST (SEQ ID NO: 150) |
| | 89% | QQSRKVP[S, N]T (SEQ ID NO: 151) |
| | 50% | QQ[S, W][R, S][K, Y][V, P][P, —][S, F]T (SEQ ID NO: 152) |
| | 44% | [Q, S]Q[S, W, I][R, S, T][K, Y, S][V, Y]P[SS, P, W]T (SEQ ID NO: 153) |
| | Overall consensus | [Q, S]Q[S, W, I][R, S, T][K, S, Y][V, Y]P[S, P, W, F, N]T (SEQ ID NO: 154) |
| Heavy Chain CDR1 | 100% | GFTFNTNA (SEQ ID NO: 155) |
| | 50% | GFTF[N, S][T, N, D][N, Y][A, D, Y] (SEQ ID NO: 156) |
| | Overall consensus | GFTF[S, N][T, N, D][N, Y][A, D, Y] (SEQ ID NO: 157) |
| Heavy Chain CDR2 | 100% | IRSKSNNYAT (SEQ ID NO: 158) |
| Heavy Chain CDR3 | Overall consensus | RH[A, G][R, Y]G[V, G, N, A][T, F, R][E, L, A, Y][H, I, G][Y, T, F][D, T][Y, R, C, G][D, V, T][Y, G, F]Y[V, A]MDY (SEQ ID NO: 159) |

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,338,298
U.S. Pat. No. 4,366,241
U.S. Pat. No. 4,472,509
U.S. Pat. No. 4,472,509
U.S. Pat. No. 4,554,101
U.S. Pat. No. 4,684,611
U.S. Pat. No. 4,748,018
U.S. Pat. No. 4,879,236
U.S. Pat. No. 4,938,948
U.S. Pat. No. 4,938,948
U.S. Pat. No. 4,952,500
U.S. Pat. No. 5,021,236
U.S. Pat. No. 5,196,066
U.S. Pat. No. 5,262,357
U.S. Pat. No. 5,302,523
U.S. Pat. No. 5,310,687
U.S. Pat. No. 5,322,783
U.S. Pat. No. 5,384,253
U.S. Pat. No. 5,464,765
U.S. Pat. No. 5,505,928
U.S. Pat. No. 5,512,282
U.S. Pat. No. 5,538,877
U.S. Pat. No. 5,538,880
U.S. Pat. No. 5,548,066
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,648,240
U.S. Pat. No. 5,656,610
U.S. Pat. No. 5,690,807
U.S. Pat. No. 5,702,932
U.S. Pat. No. 5,736,524
U.S. Pat. No. 5,741,957
U.S. Pat. No. 5,750,172
U.S. Pat. No. 5,756,687
U.S. Pat. No. 5,780,448
U.S. Pat. No. 5,789,215
U.S. Pat. No. 5,801,234
U.S. Pat. No. 5,827,690
U.S. Pat. No. 5,840,846
U.S. Pat. No. 5,871,986
U.S. Pat. No. 5,945,100
U.S. Pat. No. 5,981,274
U.S. Pat. No. 5,990,479
U.S. Pat. No. 5,994,624
U.S. Pat. No. 6,008,341
U.S. Pat. No. 6,048,616
U.S. Pat. No. 6,091,001
U.S. Pat. No. 6,274,323
U.S. Pat. No. 6,288,214
U.S. Pat. No. 6,630,307
U.S. Pat. No. 6,651,655
U.S. Pat. No. 6,756,361
U.S. Pat. No. 6,770,278
U.S. Pat. No. 6,793,923
U.S. Pat. No. 6,936,258
U.S. Patent Ser. 61/103,196
U.S. Patent Ser. 61/166,432
U.S. Patent Ser. 61/170,779
U.S. Patent Publn. 2002/0169288
U.S. Patent Publn. 20050106660
U.S. Patent Publn. 20060058510
U.S. Patent Publn. 20060088908
U.S. Patent Publn. 20100285564
Atherton et al., *Biol. of Reproduction,* 32:155-171, 1985.
Atkins et al., *Mol. Immunol.,* 45:1600-1611, 2008.
Ausubel et al., In: *Current Protocols in Molecular Biology,* John, Wiley & Sons, Inc, New York, 1996.
Baba et al., *J. Bacteriol.,* 190:300-310, 2007.
Baba et al., *Lancet,* 359:1819-1827, 2002.
Barany and Merrifield, In: *The Peptides,* Gross and Meienhofer (Eds.), Academic Press, NY, 1-284, 1979.
Berberian, et al., *Blood* 78:175-179, 1991.
Berberian, et al *Science* 261:1588-1591, 1993.
Boucher and Corey, *Clin. Infect. Dis.,* 46(5):5344-349, 2008.
Burke et al., *J. Inf. Dis.,* 170:1110-1119, 1994.
Burman et al., *J. Biol. Chem.,* 283:17579-17593, 2008.
Campbell, In: *Monoclonal Antibody Technology, Laboratory Techniques in Biochemistry and Molecular Biology,* Burden and Von Knippenberg (Eds.), Elseview, Amsterdam, 13:71-74/75-83, 1984.
Carbonelli et al., *FEMS Microbiol. Lett.,* 177(1):75-82, 1999.
Cary et al., *Mol. Immunol.,* 36:769-776, 1999.
Chandler et al., *Proc. Natl. Acad. Sci. USA,* 94(8):3596-601, 1997.
Chen and Okayama, *Mol. Cell Biol.,* 7(8):2745-2752, 1987.
Cheng et al., *FASEB J.,* 23:3393-3404, 2009.
Cocea, *Biotechniques,* 23(5):814-816, 1997.
Cumber et al., *J. Immunology,* 149B:120-126, 1992.
de Bono et al., *J. Mol. Biol.,* 342(1):131-143, 2004.
DeDent et al., *Semin. Immunopathol.,* 34:317-333, 2012.
Dholakia et al., *J. Biol. Chem.,* 264, 20638-20642, 1989.
Diep, et al., *Lancet* 367:731-739, 2006.
Emorl and Gaynes, *Clin. Microbiol. Rev.,* 6:428-442, 1993.
Epitope Mapping Protocols In: *Methods in Molecular Biology,* Vol. 66, Morris (Ed.), 1996,
European Patent 0 216 846
European Patent 0 256 055
European Patent 0 323 997
European Patent Appln. 89303964.4
Fechheimer, et al., *Proc Natl. Acad. Sci. USA,* 84:8463-8467, 1987.
Fischetti, *Clin. Microbiol. Rev.,* 2:285-314, 1989.
Forsgren, et al., *Eur. J. Immunol.* 6:207-213, 1976.
Fraley et al., *Proc. Natl. Acad. Sci. USA,* 76:3348-3352, 1979.
Gefter et al., *Somatic Cell Genet.,* 3:231-236, 1977.
Goding, In: *Monoclonal Antibodies: Principles and Practice,* 2d ed., Academic Press, Orlando, Fla., pp 60-61, 71-74, 1986.
Goding, In: *Monoclonal Antibodies: Principles and Practice,* 2d ed., Academic Press, Orlando, Fla., pp 65, 66, 1986.
Goodyear and Silverman, *J. Exp. Med.,* 197:1125-1139, 2003.

Goodyear and Silverman. *Proc. Natl. Acad. Sci. USA* 101: 11392-11397, 2004.
Gopal, *Mol. Cell Biol.,* 5:1188-1190, 1985.
Graham and Van Der Eb, *Virology,* 52:456-467, 1973.
Graille, et al., *Proc. Nat. Acad. Sci. USA* 97:5399-5404, 2000.
Harland and Weintraub, *J. Cell Biol.,* 101(3):1094-1099, 1985.
Harlow et al., Antibodies: A Laboratory Manual, Cold Spring Harbor Laboratory, Cold Spring Harbor, N.Y., Chapter 8, 1988.
Haupt et al., *PloS Pathog.,* 4:e1000250, 2008.
Hollingshead et al., *Infect. Immun.,* 55:3237-3239, 1987.
Huang, et al., *J. Clin. Invest.* 89:1331-1343, 1992.
Jones and Fischetti, *J. Exp. Med.,* 167:1114-1123, 1988.
Jones et al., *J. Exp. Med.,* 164:1226-1238, 1986.
Kaeppler et al., *Plant Cell Rep.,* 8:415-418, 1990.
Kaneda et al., *Science,* 243:375-378, 1989.
Kato et al, *J. Biol. Chem.,* 266:3361-3364, 1991.
Kennedy et al., *Proc. Natl. Acad. Sci., USA,* 105(4):1327-1332, 2008.
Khatoon et al., *Ann. of Neurology,* 26, 210-219, 1989.
Kim et al., *FASEB J.,* 25:3605-3612, 2011.
Kim et al., *J. Exp. Med.,* 207:1863-1870, 2010a.
Kim et al., *Vaccine,* 28:6382-6392, 2010b.
Kim, et al., *Curr. Opin. Microbiol.* 15:92-99, 2012b.
Kim, et al., *Infect. Immun.* 80:EPub ahead of press. 2012a
King et al., *J. Biol. Chem.,* 269, 10210-10218, 1989.
Klevens et al., *JAMA,* 298:1763-1771, 2007.
Kohl et al., *Proc. Natl. Acad. Sci., USA,* 100(4):1700-1705, 2003.
Kohler and Milstein, *Eur. J Immunol.,* 6:511-519, 1976.
Kohler and Milstein, *Nature,* 256:495-497, 1975.
Kronvall, et al., *J. Immunol.* 105:1115-1123, 1970
Kyte and Doolittle, *J. Mol. Biol.,* 157(1):105-132, 1982.
Lancefield, *J. Exp. Med.,* 47:91-103, 1928.
Lancefield, *J Immunol.,* 89:307-313, 1962.
Lee, *Trends Microbiol.,* 4(4):162-166, 1996.
Levenson et al., *Hum. Gene Ther.,* 9(8):1233-1236, 1998.
Liu et al. *Cell Mol. Biol.,* 49(2):209-216, 2003.
Mazmanian, et al., *Science.* 285:760-763, 1999.
McCarthy and Lindsay, *BMC Microbiology,* 10:173, 2010.
Merrifield, *Science,* 232(4748):341-347, 1986.
Moks, et al., *Eur. J. Biochem.* 156:3577-3588, 1986.
Nicolau and Sene, *Biochim. Biophys. Acta,* 721:185-190, 1982.
Nicolau et al., *Methods Enzymol.,* 149:157-176, 1987.
Nimmerjahn and Ravetch, *Nat. Rev. Immunol.,* 8(1):34-47, 2008.
Omirulleh et al., *Plant Mol. Biol.,* 21(3):415-28, 1993.
O'Shannessy et al., *J. Immun. Meth.,* 99, 153-161, 1987.
Owens and Haley, *J. Biol. Chem.,* 259:14843-14848, 1987.
Pack et al., *Biochem.,* 31:1579-1584, 1992.
Perry, et al., *J Biol Chem.* 277:16241-16248, 2002.
PCT Appln. PCT/US11/42845
PCT Appln. WO 00/02523
PCT Appln. WO 00/12132
PCT Appln. WO 00/12689
PCT Appln. WO 00/15238
PCT Appln. WO 01/60852
PCT Appln. WO 2006/032472
PCT Appln. WO 2006/032475
PCT Appln. WO 2006/032500
PCT Appln. WO 2007/113222
PCT Appln. WO 2007/113223
PCT Appln. WO 2011/005341
PCT Appln. WO 94/09699
PCT Appln. WO 95/06128
PCT Appln. WO 98/57994
PCT Publn. WO 2006/056464
PCT Publn. WO 99/26299
Phillips et al., *Proc. Natl. Acad. Sci., USA,* 78:4689-4693, 1981.
Potrykus et al., *Mol. Gen. Genet.,* 199(2):169-177, 1985.
Potter and Haley, *Methods Enzymol,* 91:613-633, 1983.
Rippe, et al., *Mol. Cell Biol.,* 10:689-695, 1990.
Robbins, et al., *Pediatr. Infect. Dis. J.* 6:791-794, 1987.
Robbins, et al., *J. Infect. Dis.* 161:821-832, 1990.
Robbins et al., *Adv. Exp. Med. Biol.,* 397:169-182, 1996.
Sambrook et al., In: *Molecular cloning*, Cold Spring Harbor Laboratory Press, Cold Spring Harbor, N.Y., 2001.
Sasso, et al., *J. Immunol.* 142:2778-2783, 1989.
Scott et al., *J. Exp. Med.,* 164:1641-1651, 1986.
Silverman and Goodyear, *Nat. Rev. Immunol.,* 6:465-475, 2006.
Sjödahl, et al., *Eur. J. Biochem.* 73:343-351, 1977. Sjöquist, et al., *Eur. J. Biochem.* 29:572-578, 1972.
Skerra, *J. Biotechnol.,* 74(4):257-75, 2001.
Skerra, *J. Mol. Recogn.,* 13:167-187, 2000.
Smith et al., *Mol. Microbiol.,* 83:789-804, 2012.
Spellberg, et al., *Semin Immunopathol.* 34:335-348, 2012.
Stahlenheim, et al., *J. Immunol.* 103:467-473, 1970.
Stewart and Young, In: *Solid Phase Peptide Synthesis,* 2d. ed., Pierce Chemical Co., 1984.
Stranger-Jones et al., *Proc. Natl. Acad. Sci., USA,* 103: 16942-16947, 2006.
Tam et al., *J. Am. Chem. Soc.,* 105:6442, 1983.
Tigges et al., *J. Immunol.,* 156(10):3901-3910, 1996.
Ton-That et al., *Proc. Natl. Acad. Sci., USA,* 96:12424-12429, 1999.
Wong et al., *Gene,* 10:87-94, 1980.
Yoo et al., *J. Immunol. Methods,* 261(1-2):1-20, 2002.
Zhang et al., *Microbiology,* 144:985-991, 1998.
Zhang et al., *Microbiology,* 145:177-183, 1999.

What is claimed is:

1. A purified chimeric polypeptide comprising an amino acid sequence comprising CDR1, CDR2 and CDR3 of both the light and heavy chains of a 5A10 monoclonal antibody (SEQ ID NO: 16-18, 11-13, respectively), 8E2 monoclonal antibody (SEQ ID NO: 26-28, 21-23, respectively), 3F6 monoclonal antibody (SEQ ID NO: 56-58, 51-53, respectively), 1F10 monoclonal antibody (SEQ ID NO: 66-68, 61-63, respectively), 3D11 monoclonal antibody (SEQ ID NO: 86-88, 81-83, respectively) or 2F2 monoclonal antibody (SEQ ID NO: 101-103, 96-98, respectively), wherein the polypeptide is capable of specifically binding at least two Spa IgG binding domains A, B, C, D and E of a Staphylococcal protein A (SpA) polypeptide variant that lacks non-specific Ig-binding activity, and wherein each of CDR1, CDR2, and CDR3 have up to one amino acid substitution.

2. The polypeptide of claim 1, wherein the SpA polypeptide that lacks non-specific Ig-binding activity is $SpA_{KKAA}$.

3. The polypeptide of claim 1, wherein the polypeptide competes for binding of $SpA_{KKAA}$ polypeptide with the 5A10, 8E2, 3F6, 1F10, 3D11, 2F2, monoclonal antibody.

4. The polypeptide of claim 1, wherein the polypeptide has an association constant for the $SpA_{KKAA}$ polypeptide of between about 0.5 and $100\times10^9 M^{-1}$, 1.0 and $100\times10^9 M^{-1}$, or 2.0 and $100\times10^9 M^{-1}$ as measured by ELISA.

5. The polypeptide of claim 1, wherein the polypeptide is a single domain antibody.

6. The polypeptide of claim 1, wherein the polypeptide is a humanized monoclonal antibody.

7. The polypeptide of claim 1, wherein the polypeptide is recombinant.

8. The polypeptide of claim 1, wherein the recombinant polypeptide comprises six CDR domains from a SpA-binding antibody and a scaffold from a polypeptide selected from the group consisting of an immunoglobulin, a fibronectin, a lipocalin or a *S. aureus* protein Z.

9. The polypeptide of claim 1, wherein the purified polypeptide is operatively coupled to a second recombinant polypeptide that specifically binds to a second Staphylococcal protein.

10. The polypeptide of claim 1, wherein the polypeptide is a 5A10, 8E2, 3F6, 1F10, 3D11, 2F2, monoclonal antibody.

11. The polypeptide of claim 1, wherein the polypeptide is an antibody comprising (a) a heavy chain comprising said VH region, and a human hinge, CH1, CH2, and CH3 regions from an IgG1, IgG2, IgG3 or IgG4 subtype; and (b) a light chain comprising said VL region, and either a human kappa CL or human lambda CL.

12. A pharmaceutical composition comprising a purified chimeric polypeptide comprising CDR1, CDR2 and CDR3 of both the light and heavy chains of a 5A10 monoclonal antibody (SEQ ID NO: 16-18, 11-13, respectively), 8E2 monoclonal antibody (SEQ ID NO: 26-28, 21-23, respectively), 3F6 monoclonal antibody (SEQ ID NO: 56-58, 51-53, respectively), 1F10 monoclonal antibody (SEQ ID NO: 66-68, 61-63, respectively), 3D11 monoclonal antibody (SEQ ID NO: 86-88, 81-83, respectively) or 2F2 monoclonal antibody (SEQ ID NO: 101-103, 96-98, respectively), wherein the polypeptide is capable of specifically binding at least two Spa IgG binding domains A, B, C, D and E of a Staphylococcal protein A (SpA) polypeptide variant that lacks non-specific Ig-binding activity, and wherein each of CDR1, CDR2, and CDR3 have up to one amino acid substitution.

13. The pharmaceutical composition of claim 12, comprising a single unit dose of the purified polypeptide in a sealed container.

14. The pharmaceutical composition of claim 12, comprising at least a second anti-bacterial agent.

15. The pharmaceutical composition of claim 14, wherein the second anti-bacterial agent is an antibiotic, a Staphylococcal vaccine composition or a polypeptide that specifically binds to a second Staphylococcal protein.

16. The pharmaceutical composition of claim 12 further comprising one or more physiologically acceptable excipients.

* * * * *

SEQUENCE LISTING

```
<160> NUMBER OF SEQ ID NOS: 175

<210> SEQ ID NO 1
<211> LENGTH: 520
<212> TYPE: PRT
<213> ORGANISM: Staphylococcus aureus

<400> SEQUENCE: 1

Met Leu Thr Leu Gln Ile His Thr Gly Gly Ile Asn Leu Lys Lys Lys
1               5                   10                  15
```

```
Asn Ile Tyr Ser Ile Arg Lys Leu Gly Val Gly Ala Ser Val Thr
             20                  25                  30

Leu Gly Thr Leu Leu Ile Ser Gly Gly Val Thr Pro Ala Ala Asn Ala
         35                  40                  45

Ala Gln His Asp Glu Ala Gln Gln Asn Ala Phe Tyr Gln Val Leu Asn
     50                  55                  60

Met Pro Asn Leu Asn Ala Asp Gln Arg Asn Gly Phe Ile Gln Ser Leu
 65                  70                  75                  80

Lys Asp Asp Pro Ser Gln Ser Ala Asn Val Leu Gly Glu Ala Gln Lys
                 85                  90                  95

Leu Asn Asp Ser Gln Ala Pro Lys Ala Asp Ala Gln Gln Asn Asn Phe
             100                 105                 110

Asn Lys Asp Gln Gln Ser Ala Phe Tyr Glu Ile Leu Asn Met Pro Asn
         115                 120                 125

Leu Asn Glu Ala Gln Arg Asn Gly Phe Ile Gln Ser Leu Lys Asp Asp
     130                 135                 140

Pro Ser Gln Ser Thr Asn Val Leu Gly Glu Ala Lys Lys Leu Asn Glu
145                 150                 155                 160

Ser Gln Ala Pro Lys Ala Asp Asn Asn Phe Asn Lys Glu Gln Gln Asn
             165                 170                 175

Ala Phe Tyr Glu Ile Leu Asn Met Pro Asn Leu Asn Glu Glu Gln Arg
         180                 185                 190

Asn Gly Phe Ile Gln Ser Leu Lys Asp Asp Pro Ser Gln Ser Ala Asn
     195                 200                 205

Leu Leu Ser Glu Ala Lys Lys Leu Asn Glu Ser Gln Ala Pro Lys Ala
     210                 215                 220

Asp Asn Lys Phe Asn Lys Glu Gln Gln Asn Ala Phe Tyr Glu Ile Leu
225                 230                 235                 240

His Leu Pro Asn Leu Asn Glu Glu Gln Arg Asn Gly Phe Ile Gln Ser
             245                 250                 255

Leu Lys Asp Asp Pro Ser Gln Ser Ala Asn Leu Leu Ala Glu Ala Lys
             260                 265                 270

Lys Leu Asn Asp Ala Gln Ala Pro Lys Ala Asp Asn Lys Phe Asn Lys
     275                 280                 285

Glu Gln Gln Asn Ala Phe Tyr Glu Ile Leu His Leu Pro Asn Leu Thr
290                 295                 300

Glu Glu Gln Arg Asn Gly Phe Ile Gln Ser Leu Lys Asp Asp Pro Ser
305                 310                 315                 320

Val Ser Lys Glu Ile Leu Ala Glu Ala Lys Lys Leu Asn Asp Ala Gln
             325                 330                 335

Ala Pro Lys Glu Glu Asp Asn Asn Lys Pro Gly Lys Glu Asp Gly Asn
             340                 345                 350

Lys Pro Gly Lys Glu Asp Asn Asn Lys Pro Gly Lys Glu Asp Asn Lys
         355                 360                 365

Lys Pro Gly Lys Glu Asp Asn Asn Lys Pro Gly Lys Glu Asp Asn Asn
     370                 375                 380

Lys Pro Gly Lys Glu Asp Gly Asn Lys Pro Gly Lys Glu Asp Asn Lys
385                 390                 395                 400

Lys Pro Gly Lys Glu Asp Asn Asn Lys Pro Gly Lys Glu Asp Gly Asn
             405                 410                 415

Lys Pro Gly Lys Glu Asp Gly Asn Gly Val His Val Val Lys Pro Gly
             420                 425                 430

Asp Thr Val Asn Asp Ile Ala Lys Ala Asn Gly Thr Thr Ala Asp Lys
```

```
                435                 440                 445
Ile Ala Ala Asp Asn Lys Leu Ala Asp Lys Asn Met Ile Lys Pro Gly
    450                 455                 460
Gln Glu Leu Val Val Asp Lys Lys Gln Pro Ala Asn His Ala Asp Ala
465                 470                 475                 480
Asn Lys Ala Gln Ala Leu Pro Glu Thr Gly Glu Glu Asn Pro Phe Ile
                485                 490                 495
Gly Thr Thr Val Phe Gly Gly Leu Ser Leu Ala Leu Gly Ala Ala Leu
            500                 505                 510
Leu Ala Gly Arg Arg Arg Glu Leu
            515                 520

<210> SEQ ID NO 2
<211> LENGTH: 54
<212> TYPE: PRT
<213> ORGANISM: Staphyloccocus sp.

<400> SEQUENCE: 2

Gln Gln Asn Asn Phe Asn Lys Asp Gln Gln Ser Ala Phe Tyr Glu Ile
1               5                   10                  15
Leu Asn Met Pro Asn Leu Asn Glu Ala Gln Arg Asn Gly Phe Ile Gln
            20                  25                  30
Ser Leu Lys Asp Asp Pro Ser Gln Ser Thr Asn Val Leu Gly Glu Ala
        35                  40                  45
Lys Lys Leu Asn Glu Ser
    50

<210> SEQ ID NO 3
<211> LENGTH: 51
<212> TYPE: PRT
<213> ORGANISM: Staphylococcus sp.

<400> SEQUENCE: 3

Gln His Asp Glu Ala Gln Gln Asn Ala Phe Tyr Gln Val Leu Asn Met
1               5                   10                  15
Pro Asn Leu Asn Ala Asp Gln Arg Asn Gly Phe Ile Gln Ser Leu Lys
            20                  25                  30
Asp Asp Pro Ser Gln Ser Ala Asn Val Leu Gly Glu Ala Gln Lys Leu
        35                  40                  45
Asn Asp Ser
    50

<210> SEQ ID NO 4
<211> LENGTH: 52
<212> TYPE: PRT
<213> ORGANISM: Staphylococcus sp.

<400> SEQUENCE: 4

Asn Asn Phe Asn Lys Glu Gln Gln Asn Ala Phe Tyr Glu Ile Leu Asn
1               5                   10                  15
Met Pro Asn Leu Asn Glu Glu Gln Arg Asn Gly Phe Ile Gln Ser Leu
            20                  25                  30
Lys Asp Asp Pro Ser Gln Ser Ala Asn Leu Leu Ser Glu Ala Lys Lys
        35                  40                  45
Leu Asn Glu Ser
    50

<210> SEQ ID NO 5
```

```
<211> LENGTH: 52
<212> TYPE: PRT
<213> ORGANISM: Staphylococcus sp.

<400> SEQUENCE: 5

Asn Lys Phe Asn Lys Glu Gln Gln Asn Ala Phe Tyr Glu Ile Leu His
1               5                   10                  15

Leu Pro Asn Leu Thr Glu Glu Gln Arg Asn Gly Phe Ile Gln Ser Leu
            20                  25                  30

Lys Asp Asp Pro Ser Val Ser Lys Glu Ile Leu Ala Glu Ala Lys Lys
        35                  40                  45

Leu Asn Asp Ala
    50

<210> SEQ ID NO 6
<211> LENGTH: 52
<212> TYPE: PRT
<213> ORGANISM: Staphylococcus sp.

<400> SEQUENCE: 6

Asn Lys Phe Asn Lys Glu Gln Gln Asn Ala Phe Tyr Glu Ile Leu His
1               5                   10                  15

Leu Pro Asn Leu Asn Glu Glu Gln Arg Asn Gly Phe Ile Gln Ser Leu
            20                  25                  30

Lys Asp Asp Pro Ser Gln Ser Ala Asn Leu Leu Ala Glu Ala Lys Lys
        35                  40                  45

Leu Asn Asp Ala
    50

<210> SEQ ID NO 7
<211> LENGTH: 291
<212> TYPE: PRT
<213> ORGANISM: Staphylococcus sp.

<400> SEQUENCE: 7

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175
```

```
Asp Asn Lys Phe Asn Lys Glu Lys Asn Ala Phe Tyr Glu Ile Leu
            180                 185                 190
His Leu Pro Asn Leu Asn Glu Glu Gln Arg Asn Gly Phe Ile Gln Ser
        195                 200                 205
Leu Lys Ala Ala Pro Ser Gln Ser Ala Asn Leu Leu Ala Glu Ala Lys
    210                 215                 220
Lys Leu Asn Asp Ala Gln Ala Pro Lys Ala Asp Asn Lys Phe Asn Lys
225                 230                 235                 240
Glu Lys Lys Asn Ala Phe Tyr Glu Ile Leu His Leu Pro Asn Leu Thr
                245                 250                 255
Glu Glu Gln Arg Asn Gly Phe Ile Gln Ser Leu Lys Ala Ala Pro Ser
            260                 265                 270
Val Ser Lys Glu Ile Leu Ala Glu Ala Lys Lys Leu Asn Asp Ala Gln
        275                 280                 285
Ala Pro Lys
    290

<210> SEQ ID NO 8
<211> LENGTH: 57
<212> TYPE: DNA
<213> ORGANISM: Artificial Sequence
<220> FEATURE:
<223> OTHER INFORMATION: Synthetic primer

<400> SEQUENCE: 8
aaaaaagcta gctggtctca tcctcaattt gagaagacgc aacaaacttc aactaag        57

<210> SEQ ID NO 9
<211> LENGTH: 35
<212> TYPE: DNA
<213> ORGANISM: Artificial Sequence
<220> FEATURE:
<223> OTHER INFORMATION: Synthetic primer

<400> SEQUENCE: 9
aaaaaactcg agtttccaga atgataataa attac                                35

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Trp Ser His Pro Gln Phe Glu Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Gly Phe Ala Phe Ser Asn Tyr Asp
1               5

<210> SEQ ID NO 12
<211> LENGTH: 8
<212> TYPE: PRT
<213> ORGANISM: Artificial Sequence
```

-continued

<220> FEATURE:
<223> OTHER INFORMATION: Synthetic peptide

<400> SEQUENCE: 12

Ile Ser Ser Gly Gly Thr Tyr Pro
1               5

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide

<400> SEQUENCE: 13

Ala Arg Gly Gly Phe Leu Ile Thr Thr Arg Asp Tyr Tyr Ala Met Asp
1               5                   10                  15

Tyr

<210> SEQ ID NO 14
<211> LENGTH: 124
<212> TYPE: PRT
<213> ORGANISM: Artificial Sequence
<220> FEATURE:
<223> OTHER INFORMATION: Synthetic peptide

<400> SEQUENCE: 14

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Asn Tyr
            20                  25                  30

Asp Met Ser Trp Val Arg Gln Thr Pro Glu Lys Arg Leu Glu Trp Val
        35                  40                  45

Ala Thr Ile Ser Ser Gly Gly Thr Tyr Pro Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Leu Ser Ser Leu Arg Ser Glu Asp Thr Ala Leu Tyr Tyr Cys
                85                  90                  95

Ala Arg Gly Gly Phe Leu Ile Thr Thr Arg Asp Tyr Tyr Ala Met Asp
            100                 105                 110

Tyr Trp Gly Gln Gly Thr Ser Val Thr Val Ser Ser
        115                 120

<210> SEQ ID NO 15
<211> LENGTH: 373
<212> TYPE: DNA
<213> ORGANISM: Artificial Sequence
<220> FEATURE:
<223> OTHER INFORMATION: Synthetic primer

<400> SEQUENCE: 15
gaagtgaagc tggtggagtc tgggggaggc ttagtgaagc ctggagggtc cctgaaactc      60
tcctgtgcag cctctggatt cgctttcagt aactatgaca tgtcttgggt tcgccagact     120
ccggagaaga ggctgagtg gtcgcaacc attagtagtg gtggtactta cccctactat      180
ccagacagtg tgaagggccg tttcaccatc tccagagaca atgccaagaa caccctgtac     240
ctgcaattga gcagtctgag gtctgaggac acggccttgt attactgtgc aagaggggga     300 ttttgatta cgacacggga ttactatgct atggactact ggggtcaagg aacctcagtc     360
accgtctcct cag                                                            373

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide

<400> SEQUENCE: 16

Ser Ser Val Ser Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: Synthetic peptide

<400> SEQUENCE: 17

Asp Thr Ser
1

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide

<400> SEQUENCE: 18

Gln Gln Trp Ser Ser Tyr Pro Pro Thr
1               5

<210> SEQ ID NO 19
<211> LENGTH: 106
<212> TYPE: PRT
<213> ORGANISM: Artificial Sequence
<220> FEATURE:
<223> OTHER INFORMATION: Synthetic peptide

<400> SEQUENCE: 19

Thr Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Lys Pro Gly Ser Ser Pro Arg Leu Leu Ile Tyr
            35                  40                  45

Asp Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Ile Lys
            100                 105

<210> SEQ ID NO 20
<211> LENGTH: 319
<212> TYPE: DNA
<213> ORGANISM: Artificial Sequence
<220> FEATURE:
<223> OTHER INFORMATION: Synthetic primer

<400> SEQUENCE: 20

```
acaattgttc tcacccagtc tccagcaatc atgtctgcat ctccagggga gaaggtcacc    60
atgacctgca gtgccagctc aagtgtaagt tacatgtact ggtaccagca gaagccagga   120
tcctccccca gactcctgat ttatgacaca tccaacctgg cttctggagt ccctgttcgc   180
ttcagtggca gtgggtctgg gacctcttac tctctcacaa tcagccgaat ggaggctgaa   240
gatgctgcca cttattactg ccagcagtgg agtagttacc cacccacgtt cggagggggg   300
accaagctgg aaataaaac                                                319
```

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Gly Tyr Thr Phe Thr Glu Tyr Ser
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Phe Tyr Pro Gly Ser Gly Tyr Ile
1               5

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide

<400> SEQUENCE: 23

Arg His Gly Tyr Gly Asn Tyr Val Gly Tyr Ala Met Asp Tyr
1               5                   10

<210> SEQ ID NO 24
<211> LENGTH: 122
<212> TYPE: PRT
<213> ORGANISM: Artificial Sequence
<220> FEATURE:
<223> OTHER INFORMATION: Synthetic peptide

<400> SEQUENCE: 24

Lys Val Gln Leu Gln Gln Ser Gly Ala Gly Leu Val Lys Pro Gly Ala
1               5                   10                  15

Ser Val Lys Leu Ser Cys Lys Ala Ser Gly Tyr Thr Phe Thr Glu Tyr
            20                  25                  30

Ser Ile His Trp Val Lys Gln Ser Gly Gln Gly Leu Glu Trp Ile
        35                  40                  45

Gly Trp Phe Tyr Pro Gly Ser Gly Tyr Ile Lys Tyr Asn Glu Lys Phe
    50                  55                  60

Lys Asp Lys Ala Thr Leu Thr Ala Asp Lys Ser Ser Ser Thr Val Tyr
65                  70                  75                  80

Met Glu Phe Ser Arg Leu Thr Ser Glu Asp Ser Ala Val Tyr Phe Cys
            85                  90                  95

Ala Arg His Gly Tyr Gly Asn Tyr Val Gly Tyr Ala Met Asp Tyr Trp
        100                 105                 110

Gly Gln Gly Thr Ser Val Thr Val Ser Ser
        115                 120

<210> SEQ ID NO 25
<211> LENGTH: 367
<212> TYPE: DNA
<213> ORGANISM: Artificial Sequence
<220> FEATURE:
<223> OTHER INFORMATION: Synthetic primer

<400> SEQUENCE: 25
aaggtccagc tgcagcagtc tggagctggg ctggtgaaac ccggggcatc agtgaagctg     60
tcctgcaagg cttctggcta caccttcact gaatatagta tacactgggt aaaacagagc    120
tctggacagg tcttgagtg gattgggtgg ttttaccctg aagtggtta tataaagtac      180 aatgagaaat tcaaggacaa ggccacattg actgcggaca atcctccag cacagtctat     240 atggagttta gtagattgac atctgaagac tctgcggtct acttctgtgc aagacacgga    300
tatggtaact acgtggggta tgctatggac tactggggtc aaggaacctc agtcaccgtc    360
tcctcag                                                              367

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Glu Ile Ile Tyr Ser Tyr
1               5

<210> SEQ ID NO 27
<211> LENGTH: 3
<212> TYPE: PRT
<213> ORGANISM: Artificial Sequence
<220> FEATURE:
<223> OTHER INFORMATION: Synthetic peptide

<400> SEQUENCE: 27

Phe Ala Lys
1

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Gln His His Tyr Gly Thr Pro Tyr Thr
1               5

<210> SEQ ID NO 29
<211> LENGTH: 107
<212> TYPE: PRT
<213> ORGANISM: Artificial Sequence
<220> FEATURE:
<223> OTHER INFORMATION: Synthetic peptide

<400> SEQUENCE: 29

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Ile Ile Tyr Ser Tyr
            20                  25                  30

Leu Ala Trp Tyr Gln Gln Lys Gln Gly Lys Ser Pro Gln Leu Leu Val
        35                  40                  45

Tyr Phe Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ile Tyr Tyr Cys Gln His His Tyr Gly Thr Pro Tyr
                85                  90                  95

Thr Phe Gly Gly Gly Thr Lys Leu Glu Ile Lys
            100                 105
```

<210> SEQ ID NO 30
<211> LENGTH: 365
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t

<400> SEQUENCE: 30

```
aaggtccagc tgcaacagtc tggagctggg ctggtgaaac ccggggcatc agtgaagctg      60
tcctgcaagg cttctggcta caccttcact gaatatagta tacactgggt aaaacagagc     120
tctggacagg gtcttgagtg gattgggtgg ttttaccctg gaagtggtta tataaagtac     180
aatganaaat tcaaggacaa ggccacattg actgcggaca atcctccan cacagtctat     240
atggagttta gtagattgac atctgaagac tctgcggnct acttctgtgc aagacacgga     300
tatggtaact acgtggggta tgctatggac tactggggtc aaggaacctc aatcaccgtc     360
tcctc                                                                 365
```

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide

<400> SEQUENCE: 31

```
Gly Tyr Asn Phe Thr Asp Tyr Ser
1               5
```

<210> SEQ ID NO 32
<211> LENGTH: 8
<212> TYPE: PRT
<213> ORGANISM: Artificial Sequence
<220> FEATURE:

<223> OTHER INFORMATION: Synthetic peptide

<400> SEQUENCE: 32

Ile Asn Thr Glu Thr Ala Glu Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide

<400> SEQUENCE: 33

Ala His Phe Asp Cys
1               5

<210> SEQ ID NO 34
<211> LENGTH: 112
<212> TYPE: PRT
<213> ORGANISM: Artificial Sequence
<220> FEATURE:
<223> OTHER INFORMATION: Synthetic peptide

<400> SEQUENCE: 34

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Asn Phe Thr Asp Tyr
            20                  25                  30

Ser Met His Trp Val Lys Gln Ala Pro Gly Lys Gly Leu Lys Trp Val
        35                  40                  45

Gly Trp Ile Asn Thr Glu Thr Ala Glu Ser Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Ser Leu Lys Asp Glu Asp Thr Ala Thr Phe Phe Cys
                85                  90                  95

Ala His Phe Asp Cys Trp Gly Gln Gly Thr Thr Leu Thr Val Ser Ser
            100                 105                 110

<210> SEQ ID NO 35
<211> LENGTH: 336
<212> TYPE: DNA
<213> ORGANISM: Artificial Sequence
<220> FEATURE:
<223> OTHER INFORMATION: Synthetic primer

<400> SEQUENCE: 35
cagatccagt tggtgcagtc tggacctgag ctgaagaagc tggagagaca agtcaagatc      60
tcctgcaagg cttctggtta taatttcaca gactattcaa tgcactgggt gaagcaggct     120
ccaggaaagg gtttaaagtg ggtgggctgg ataaacactg agactgctga gtcaacatat     180
gcagatgact tcaagggacg gtttgccttc tctttggaaa cctctgccag cactgcctat     240
ttgcagatca acagcctcaa agatgaggac acggctacat tttctgtgc ccactttgac     300 tgttggggcc aaggcaccac tctcacagtc tcctca                              336

<210> SEQ ID NO 36
<211> LENGTH: 11
<212> TYPE: PRT
<213> ORGANISM: Artificial Sequence
<220> FEATURE:

<223> OTHER INFORMATION: Synthetic peptide

<400> SEQUENCE: 36

Gln Ser Leu Val His Ser Asn Gly Asn Thr Tyr
1               5                   10

<210> SEQ ID NO 37
<211> LENGTH: 3
<212> TYPE: PRT
<213> ORGANISM: Artificial Sequence
<220> FEATURE:
<223> OTHER INFORMATION: Synthetic peptide

<400> SEQUENCE: 37

Lys Val Ser
1

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Ser Gln Ile Thr Tyr Val Pro Trp Thr
1               5

<210> SEQ ID NO 39
<211> LENGTH: 112
<212> TYPE: PRT
<213> ORGANISM: Artificial Sequence
<220> FEATURE:
<223> OTHER INFORMATION: Synthetic peptide

<400> SEQUENCE: 39

Asp Val Val Met Thr Gln Ile Ser Leu Ser Leu Pro Val Thr Leu Gly
1               5                   10                  15

Asp Gln Ala Ser Ile Ser Cys Arg Ala Ser Gln Ser Leu Val His Ser
            20                  25                  30

Asn Gly Asn Thr Tyr Leu Asn Trp Tyr Leu Gln Lys Pro Gly Gln Ser
        35                  40                  45

Pro Lys Leu Leu Ile His Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ile
                85                  90                  95

Thr Tyr Val Pro Trp Thr Phe Gly Gly Gly Thr Lys Leu Glu Ile Lys
                100                 105                 110

<210> SEQ ID NO 40
<211> LENGTH: 337
<212> TYPE: DNA
<213> ORGANISM: Artificial Sequence
<220> FEATURE:
<223> OTHER INFORMATION: Synthetic primer

<400> SEQUENCE: 40
gatgttgtga tgacccaaat tcactctcc ctgcctgtca ctcttggaga tcaagcctcc      60
atctcttgca gagctagtca gagccttgta cacagtaatg gaaacaccta tttaaattgg     120
tacctgcaga agccaggcca gtctccaaag ctcctgatcc acaaagtctc caaccgattt     180

```
tctggggtcc cagacaggtt cagtggcagt ggatcaggga cagatttcac actcaagatc    240
agcagagtgg aggctgagga tctgggagtt tatttctgct ctcaaattac atatgttccg    300
tggacgttcg gtggaggcac caagctggaa atcaaac                              337
```

<210> SEQ ID NO 41
<211> LENGTH: 8
<212> TYPE: PRT
<213> ORGANISM: Artificial Sequence
<220> FEATURE:
<223> OTHER INFORMATION: Synthetic peptide

<400> SEQUENCE: 41

Gly Tyr Thr Phe Thr Asp Tyr Ser
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic peptide

<400> SEQUENCE: 42

Ile Asn Thr Ala Thr Gly Glu Pro
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide

<400> SEQUENCE: 43

Ala Pro Gln Leu Thr Gly Pro Phe Ala Tyr
1               5                   10

<210> SEQ ID NO 44
<211> LENGTH: 117
<212> TYPE: PRT
<213> ORGANISM: Artificial Sequence
<220> FEATURE:
<223> OTHER INFORMATION: Synthetic peptide

<400> SEQUENCE: 44

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Val His Trp Val Lys Gln Ala Pro Gly Lys Gly Leu Lys Trp Met
        35                  40                  45

Ala Trp Ile Asn Thr Ala Thr Gly Glu Pro Thr Phe Ala Asp Asp Phe
    50                  55                  60

Lys Gly Arg Phe Ala Phe Ser Leu Glu Thr Ser Ala Arg Thr Ala Tyr
65                  70                  75                  80

Leu Gln Ile Asn Asn Leu Lys Asn Glu Asp Thr Ala Thr Tyr Phe Cys
                85                  90                  95

Ala Pro Gln Leu Thr Gly Pro Phe Ala Tyr Trp Gly His Gly Thr Leu
            100                 105                 110

Val Thr Val Ser Ala
        115

<210> SEQ ID NO 45
<211> LENGTH: 351
<212> TYPE: DNA
<213> ORGANISM: Artificial Sequence
<220> FEATURE:
<223> OTHER INFORMATION: Synthetic primer

<400> SEQUENCE: 45

```
cagatccagt tggtacagtc tggacctgag ttgaagaagc ctggagagac agtcaagatc    60
tcctgcaagg cttctggtta taccttcaca gactattcag tgcactgggt gaagcaggct   120
ccaggaaagg gtttaaagtg gatggcctgg ataaacactg cgactggtga gccaacattt   180
gcagatgact tcaagggacg gtttgccttc tctttggaaa cctctgccag aactgcctat   240
ttgcagatca acaacctcaa aaatgaggac acggctacat atttctgtgc tccccagtta   300
actggcccctt tgcttactg gggccacggg actctggtca ctgtctctgc a            351
```

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide

<400> SEQUENCE: 46

Glu Asn Ile His Asn Tyr
1               5

<210> SEQ ID NO 47
<211> LENGTH: 3
<212> TYPE: PRT
<213> ORGANISM: Artificial Sequence
<220> FEATURE:
<223> OTHER INFORMATION: Synthetic peptide

<400> SEQUENCE: 47

Asn Ala Lys
1

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Gln His Ser Trp Ser Ile Pro Tyr Thr
1               5

<210> SEQ ID NO 49
<211> LENGTH: 107
<212> TYPE: PRT
<213> ORGANISM: Artificial Sequence
<220> FEATURE:
<223> OTHER INFORMATION: Synthetic peptide

<400> SEQUENCE: 49

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile His Asn Tyr
            20                  25                  30

Leu Ala Trp Tyr Gln Gln Lys Gln Gly Lys Ser Pro Gln Leu Leu Val

```
                 35                  40                  45
Tyr Asn Ala Lys Thr Leu Thr Asp Gly Val Pro Ser Arg Phe Ser Gly
         50                  55                  60
Ser Gly Ser Gly Thr Gln Phe Ser Leu Lys Ile Asn Ser Leu Gln Ala
 65                  70                  75                  80
Gly Asp Phe Gly Ser Tyr Tyr Cys Gln His Ser Trp Ser Ile Pro Tyr
                 85                  90                  95
Thr Phe Gly Gly Gly Thr Arg Leu Gln Ile Arg
            100                 105
```

<210> SEQ ID NO 50
<211> LENGTH: 322
<212> TYPE: DNA
<213> ORGANISM: Artificial Sequence
<220> FEATURE:
<223> OTHER INFORMATION: Synthetic primer

<400> SEQUENCE: 50

```
gacatccaga tgactcagtc tccagcctcc ctatctgcat ctgtgggaga aactgtcacc    60
atcacatgtc gagcaagtga gaatattcac aattatttag catggtatca gcagaaacag   120
ggaaaatctc ctcagctcct ggtctataat gcaaaaacct taacagatgg tgtgccatca   180
aggttcagtg gcagtggatc aggaacacaa ttttctctca aaatcaacag cctgcaggct   240
ggagattttg ggagttatta ctgtcaacat tcttggagta taccgtacac gtttggaggg   300
gggaccaggc tacaaataag ac                                            322
```

<210> SEQ ID NO 51
<211> LENGTH: 8
<212> TYPE: PRT
<213> ORGANISM: Artificial Sequence
<220> FEATURE:
<223> OTHER INFORMATION: Synthetic peptide

<400> SEQUENCE: 51

```
Gly Phe Thr Phe Asn Thr Asn Ala
  1               5
```

<210> SEQ ID NO 52
<211> LENGTH: 10
<212> TYPE: PRT
<213> ORGANISM: Artificial Sequence
<220> FEATURE:
<223> OTHER INFORMATION: Synthetic peptide

<400> SEQUENCE: 52

```
Ile Arg Ser Lys Ser Asn Asn Tyr Ala Thr
  1               5                  10
```

<210> SEQ ID NO 53
<211> LENGTH: 14
<212> TYPE: PRT
<213> ORGANISM: Artificial Sequence
<220> FEATURE:
<223> OTHER INFORMATION: Synthetic peptide

<400> SEQUENCE: 53

```
Val Thr Glu His Tyr Asp Tyr Asp Tyr Tyr Val Met Asp Tyr
  1               5                  10
```

<210> SEQ ID NO 54
<211> LENGTH: 123
<212> TYPE: PRT

<213> ORGANISM: Artificial Sequence
<220> FEATURE:
<223> OTHER INFORMATION: Synthetic peptide
<220> FEATURE:
<221> NAME/KEY: misc_feature
<222> LOCATION: (120)..(120)
<223> OTHER INFORMATION: Xaa can be any naturally occurring amino acid

<400> SEQUENCE: 54

```
Glu Val Gln Leu Val Glu Thr Gly Gly Gly Leu Val Gln Pro Lys Gly
1               5                  10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Ser Ile Ser Arg Asp Asp Ser Gln Asn Met
65                  70                  75                  80

Leu Ser Leu Gln Met Asn Asn Leu Lys Thr Glu Asp Thr Ala Ile Tyr
                85                  90                  95

Tyr Cys Val Thr Glu His Tyr Asp Tyr Asp Tyr Val Met Asp Tyr
            100                 105                 110

Trp Gly Gln Gly Thr Ser Val Xaa Ser Pro Gln
        115                 120
```

<210> SEQ ID NO 55
<211> LENGTH: 370
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (359)..(360)
<223> OTHER INFORMATION: n is a, c, g, or t

<400> SEQUENCE: 55

```
gaggtgcagc ttgttgagac tggtggagga ttggtgcagc ctaaagggtc attgaaactc      60
tcatgtgcag cctctggatt caccttcaat accaatgcca tgaactgggt ccgccaggct     120
ccaggaaagg gtttggaatg ggttgctcgc ataagaagta aaagtaataa ttatgcaaca     180
tattatgccg attcagtgaa agacaggttc tccatctcca gggatgattc acaaaacatg     240
ctctctctgc aaatgaacaa cttgaaaact gaggacacag ccatctatta ctgtgtgaca     300
gaacactatg attacgatta ctatgttatg gactactggg gtcaaggaac ctcagtcann     360
tctcctcagc                                                            370
```

<210> SEQ ID NO 56
<211> LENGTH: 10
<212> TYPE: PRT
<213> ORGANISM: Artificial Sequence
<220> FEATURE:
<223> OTHER INFORMATION: Synthetic peptide

<400> SEQUENCE: 56

```
Glu Ser Val Glu Tyr Ser Gly Ala Ser Leu
1               5                  10
```

<210> SEQ ID NO 57
<211> LENGTH: 3
<212> TYPE: PRT

```
<213> ORGANISM: Artificial Sequence
<220> FEATURE:
<223> OTHER INFORMATION: Synthetic peptide

<400> SEQUENCE: 57

Ala Ala Ser
1

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Gln Gln Ser Arg Lys Val Pro Ser Thr
1               5

<210> SEQ ID NO 59
<211> LENGTH: 110
<212> TYPE: PRT
<213> ORGANISM: Artificial Sequence
<220> FEATURE:
<223> OTHER INFORMATION: Synthetic peptide

<400> SEQUENCE: 59

Ile Val Leu Thr Gln Ser Pro Ala Ser Leu Ala Val Ser Leu Gly Gln
1               5                   10                  15

Arg Ala Thr Ile Ser Cys Arg Ala Ser Glu Ser Val Glu Tyr Ser Gly
            20                  25                  30

Ala Ser Leu Met Gln Trp Tyr Gln His Lys Pro Gly Gln Pro Pro Lys
        35                  40                  45

Leu Leu Ile Tyr Ala Ala Ser Asn Val Glu Ser Gly Val Pro Ala Arg
    50                  55                  60

Phe Ser Gly Ser Gly Ser Gly Thr Asp Phe Ser Leu Asn Ile His Pro
65                  70                  75                  80

Val Glu Glu Asp Asp Ile Ala Met Tyr Phe Cys Gln Gln Ser Arg Lys
                85                  90                  95

Val Pro Ser Thr Phe Gly Gly Gly Thr Lys Leu Glu Ile Lys
            100                 105                 110

<210> SEQ ID NO 60
<211> LENGTH: 331
<212> TYPE: DNA
<213> ORGANISM: Artificial Sequence
<220> FEATURE:
<223> OTHER INFORMATION: Synthetic primer

<400> SEQUENCE: 60
attgtgctca cccaatctcc agcttctttg gctgtgtctc ttgggcagag agccaccatc      60
tcctgcagag ccagtgaaag tgttgaatat tctggcgcaa gtttaatgca gtggtaccaa     120
cacaaaccag acagccacc caaactcctc atctatgctg catccaacgt agaatctggg      180
gtccctgcca ggtttagtgg cagtgggtct gggacagact tcagcctcaa catccatcct     240
gtggaggagg atgatattgc aatgtatttc tgtcagcaaa gtaggaaggt tccttccacg     300
ttcggagggg ggaccaagct ggaaataaaa c                                    331

<210> SEQ ID NO 61
<211> LENGTH: 8
<212> TYPE: PRT
```

```
<213> ORGANISM: Artificial Sequence
<220> FEATURE:
<223> OTHER INFORMATION: Synthetic peptide

<400> SEQUENCE: 61

Gly Asn Ala Phe Thr Asn Tyr Leu
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide

<400> SEQUENCE: 62

Ile Asn Pro Gly Ser Gly Ile Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Ser Gly Ser Ala Asn Trp Phe Ala Tyr
1               5

<210> SEQ ID NO 64
<211> LENGTH: 116
<212> TYPE: PRT
<213> ORGANISM: Artificial Sequence
<220> FEATURE:
<223> OTHER INFORMATION: Synthetic peptide

<400> SEQUENCE: 64

Lys Glu Leu Ile Ser Ser Lys Ser Glu Glu Lys Trp Pro Gly Thr
1               5                   10                  15

Ser Val Lys Val Ser Cys Lys Ala Ser Gly Asn Ala Phe Thr Asn Tyr
                20                  25                  30

Leu Ile Glu Trp Ile Lys Gln Arg Pro Gly Gln Gly Leu Glu Trp Ile
            35                  40                  45

Gly Val Ile Asn Pro Gly Ser Gly Ile Thr Asn Tyr Asn Glu Lys Phe
        50                  55                  60

Lys Gly Lys Ala Thr Leu Thr Ala Asp Lys Ser Ser Asn Thr Ala Tyr
65                  70                  75                  80

Met Gln Leu Ser Ser Leu Ser Ser Asp Asp Ser Ala Val Tyr Phe Cys
                85                  90                  95

Ser Gly Ser Ala Asn Trp Phe Ala Tyr Trp Gly Gln Gly Thr Leu Val
            100                 105                 110

Thr Val Ser Ala
        115

<210> SEQ ID NO 65
<211> LENGTH: 348
<212> TYPE: DNA
<213> ORGANISM: Artificial Sequence
<220> FEATURE:
<223> OTHER INFORMATION: Synthetic primer

<400> SEQUENCE: 65
```

```
aaggaactca tcagttccaa atctgaagaa gagaaatggc ctgggacttc agtgaaggtg    60
tcctgcaagg cttctggaaa cgccttcact aattatttaa tagagtggat aaaacagagg   120
cctggacagg gccttgagtg gattggagtg attaatcctg aagtggaat actaactac     180 aatgagaagt tcaagggcaa ggcaacactg actgcagaca atcctccaa cactgcctac    240 atgcagctca gcagcctgtc atctgatgac tctgcggtct atttctgttc aggatcggcc   300
aactggtttg cttactgggg ccagggggact ctggtcaccg tctctgca               348
```

```
<210> SEQ ID NO 66
<211> LENGTH: 10
<212> TYPE: PRT
<213> ORGANISM: Artificial Sequence
<220> FEATURE:
<223> OTHER INFORMATION: Synthetic peptide

<400> SEQUENCE: 66

Glu Ser Val Glu Tyr Ser Gly Ala Ser Leu
1               5                   10

<210> SEQ ID NO 67
<211> LENGTH: 3
<212> TYPE: PRT
<213> ORGANISM: Artificial Sequence
<220> FEATURE:
<223> OTHER INFORMATION: Synthetic peptide

<400> SEQUENCE: 67

Ala Ala Ser
1

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

Gln Gln Ser Arg Lys Val Pro Ser Thr
1               5

<210> SEQ ID NO 69
<211> LENGTH: 111
<212> TYPE: PRT
<213> ORGANISM: Artificial Sequence
<220> FEATURE:
<223> OTHER INFORMATION: Synthetic peptide

<400> SEQUENCE: 69

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Ser
            20                  25                  30

Gly Ala Ser Leu Met Gln Trp Tyr Gln His Lys Pro Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95
```

Lys Val Pro Ser Thr Phe Gly Gly Gly Thr Lys Leu Glu Ile Lys
              100                 105                 110

<210> SEQ ID NO 70
<211> LENGTH: 334
<212> TYPE: DNA
<213> ORGANISM: Artificial Sequence
<220> FEATURE:
<223> OTHER INFORMATION: Synthetic primer

<400> SEQUENCE: 70
gacattgtgc tcacccaatc tccagcttct ttggctgtgt ctcttgggca gagagccacc    60
atctcctgca gagccagtga aagtgttgaa tattctggcg caagtttaat gcagtggtac   120
caacacaaac caggacagcc acccaaactc ctcatctatg ctgcatccaa cgtagaatct   180
ggggtccctg ccaggtttag tggcagtggg tctgggacag acttcagcct caacatccat   240
cctgtggagg aggatgatat tgcaatgtat ttctgtcagc aaagtaggaa ggttccttcc   300
acgttcggag gggggaccaa gctggaaata aaac                               334

<210> SEQ ID NO 71
<211> LENGTH: 8
<212> TYPE: PRT
<213> ORGANISM: Artificial Sequence
<220> FEATURE:
<223> OTHER INFORMATION: Synthetic peptide

<400> SEQUENCE: 71

Gly Asn Ala Phe Thr Asn Tyr Leu
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide

<400> SEQUENCE: 72

Ile Asn Pro Gly Ser Gly Ile Thr
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Ser Gly Ser Ala Asn Trp Phe Ala Tyr
1               5

<210> SEQ ID NO 74
<211> LENGTH: 116
<212> TYPE: PRT
<213> ORGANISM: Artificial Sequence
<220> FEATURE:
<223> OTHER INFORMATION: Synthetic peptide

<400> SEQUENCE: 74

Gln Val Gln Leu Gln Gln Ser Gly Ala Glu Leu Val Arg Pro Gly Thr
1               5                   10                  15

Ser Val Lys Val Ser Cys Lys Ala Ser Gly Asn Ala Phe Thr Asn Tyr
            20                  25                  30

-continued

Leu Ile Glu Trp Ile Lys Gln Arg Pro Gly Gln Gly Leu Glu Trp Ile
            35                  40                  45

Gly Val Ile Asn Pro Gly Ser Gly Ile Thr Asn Tyr Asn Glu Lys Phe
 50                  55                  60

Lys Gly Lys Ala Thr Leu Thr Ala Asp Lys Ser Ser Asn Thr Ala Tyr
 65                  70                  75                  80

Met Gln Leu Ser Ser Leu Ser Ser Asp Asp Ser Ala Val Tyr Phe Cys
                85                  90                  95

Ser Gly Ser Ala Asn Trp Phe Ala Tyr Trp Gly Gln Gly Thr Leu Val
            100                 105                 110

Thr Val Ser Ala
        115

<210> SEQ ID NO 75
<211> LENGTH: 348
<212> TYPE: DNA
<213> ORGANISM: Artificial Sequence
<220> FEATURE:
<223> OTHER INFORMATION: Synthetic primer

<400> SEQUENCE: 75
caggtccagc tgcagcagtc tggagctgaa ctggtaaggc ctgggacttc agtgaaggtg      60
tcctgcaagg cttctggaaa cgccttcact aattatttaa tagagtggat aaaacagagg     120
cctggacagg gccttgagtg gattggagtg attaatcctg gaagtggaat tactaactac     180
aatgagaagt tcaagggcaa ggcaacactg actgcagaca atcctccaa cactgcctac      240 atgcagctca gcagcctgtc atctgatgac tctgcggtct atttctgttc aggatcggcc     300
aactggtttg cttactgggg ccaagggact ctggtcactg tctctgca                  348

<210> SEQ ID NO 76
<211> LENGTH: 10
<212> TYPE: PRT
<213> ORGANISM: Artificial Sequence
<220> FEATURE:
<223> OTHER INFORMATION: Synthetic peptide

<400> SEQUENCE: 76

Glu Ser Val Glu Tyr Ser Gly Ala Ser Leu
1               5                   10

<210> SEQ ID NO 77
<211> LENGTH: 3
<212> TYPE: PRT
<213> ORGANISM: Artificial Sequence
<220> FEATURE:
<223> OTHER INFORMATION: Synthetic peptide

<400> SEQUENCE: 77

Ala Ala Ser
1

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide

<400> SEQUENCE: 78

Gln Gln Ser Arg Lys Val Pro Ser Thr
1               5

<210> SEQ ID NO 79
<211> LENGTH: 111
<212> TYPE: PRT
<213> ORGANISM: Artificial Sequence
<220> FEATURE:
<223> OTHER INFORMATION: Synthetic peptide

<400> SEQUENCE: 79

Asp Ile Val Leu Thr Gln Ser Pro Ala Ser Leu Ala Val Ser Leu Gly
1               5                   10                  15

Gln Arg Ala Ser Ile Ser Cys Arg Ala Ser Glu Ser Val Glu Tyr Ser
            20                  25                  30

Gly Ala Ser Leu Met Gln Trp Tyr Gln His Lys Pro Gly Gln Pro Pro
        35                  40                  45

Lys Leu Leu Ile Tyr Ala Ala Ser Asn Val Glu Ser Gly Val Pro Val
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Ser Thr Phe Gly Gly Gly Thr Lys Leu Glu Ile Lys
            100                 105                 110

<210> SEQ ID NO 80
<211> LENGTH: 334
<212> TYPE: DNA
<213> ORGANISM: Artificial Sequence
<220> FEATURE:
<223> OTHER INFORMATION: Synthetic primer

<400> SEQUENCE: 80
gacattgtgc tcacccaatc tccagcttct ttggctgtgt ctcttgggca gagagccagc      60
atctcctgca gagccagtga aagtgttgaa tattcaggcg caagtttaat gcagtggtac     120
caacacaaac caggacagcc acccaaactc ctcatctatg ctgcatccaa cgtagaatct     180
ggggtccctg tcaggtttag tggcagtggg tctgggacag acttcagcct caacatccat     240
cctgtggagg aggatgatat tgcaatgtat ttctgtcagc aaagtaggaa ggttccctct     300
acgttcggag gggggaccaa gctggaaata aaac                                 334

<210> SEQ ID NO 81
<211> LENGTH: 8
<212> TYPE: PRT
<213> ORGANISM: Artificial Sequence
<220> FEATURE:
<223> OTHER INFORMATION: Synthetic peptide

<400> SEQUENCE: 81

Gly Tyr Ser Phe Thr Ser Tyr Tyr
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic peptide

<400> SEQUENCE: 82

Ile Asp Pro Phe Asn Gly Gly Thr
1               5

<210> SEQ ID NO 83
<211> LENGTH: 14
<212> TYPE: PRT
<213> ORGANISM: Artificial Sequence
<220> FEATURE:
<223> OTHER INFORMATION: Synthetic peptide

<400> SEQUENCE: 83

Ala Arg Tyr Gly Tyr Asp Gly Thr Phe Tyr Ala Met Asp Tyr
1               5                   10

<210> SEQ ID NO 84
<211> LENGTH: 116
<212> TYPE: PRT
<213> ORGANISM: Artificial Sequence
<220> FEATURE:
<223> OTHER INFORMATION: Synthetic peptide

<400> SEQUENCE: 84

Gln Ser Gly Pro Glu Leu Met Lys Pro Gly Ala Ser Val Lys Ile Ser
1               5                   10                  15

Cys Lys Ala Ser Gly Tyr Ser Phe Thr Ser Tyr Tyr Met His Trp Val
            20                  25                  30

Lys Gln Ser His Gly Lys Ser Leu Glu Trp Ile Gly Tyr Ile Asp Pro
        35                  40                  45

Phe Asn Gly Gly Thr Ser Tyr Asn Gln Lys Phe Lys Gly Lys Ala Thr
    50                  55                  60

Leu Thr Val Asp Lys Ser Ser Ser Thr Ala Tyr Met His Leu Ser Ser
65                  70                  75                  80

Leu Thr Ser Glu Asp Ser Ala Val Tyr Tyr Cys Ala Arg Tyr Gly Tyr
                85                  90                  95

Asp Gly Thr Phe Tyr Ala Met Asp Tyr Trp Gly Gln Gly Thr Ser Val
            100                 105                 110

Thr Val Ser Ser
        115

<210> SEQ ID NO 85
<211> LENGTH: 255
<212> TYPE: DNA
<213> ORGANISM: Artificial Sequence
<220> FEATURE:
<223> OTHER INFORMATION: Synthetic primer

<400> SEQUENCE: 85
cagtctggac ctgagctgat gaagcctggg gcttcagtga agatatcctg caaggcttct      60
ggttactcat tcactagcta ctacatgcac tgggtgaagc agagccatgg aaagagcctt     120
gagtggattg gatatattga tcctttcaat ggtggtacta gctacaacca gaaattcaag     180
ggcaaggcca cattgactgt agacaaatct tccagcacag cctacatgca tctcagcagc     240
ctgacatctg aggac                                                     255

<210> SEQ ID NO 86
<211> LENGTH: 5
<212> TYPE: PRT
<213> ORGANISM: Artificial Sequence
<220> FEATURE:
<223> OTHER INFORMATION: Synthetic peptide

<400> SEQUENCE: 86

Ser Ser Val Ser Tyr

<210> SEQ ID NO 87
<211> LENGTH: 3
<212> TYPE: PRT
<213> ORGANISM: Artificial Sequence
<220> FEATURE:
<223> OTHER INFORMATION: Synthetic peptide

<400> SEQUENCE: 87

Glu Ile Ser
1

<210> SEQ ID NO 88
<211> LENGTH: 8
<212> TYPE: PRT
<213> ORGANISM: Artificial Sequence
<220> FEATURE:
<223> OTHER INFORMATION: Synthetic peptide

<400> SEQUENCE: 88

Gln Gln Trp Ser Tyr Pro Phe Thr
1               5

<210> SEQ ID NO 89
<211> LENGTH: 105
<212> TYPE: PRT
<213> ORGANISM: Artificial Sequence
<220> FEATURE:
<223> OTHER INFORMATION: Synthetic peptide

<400> SEQUENCE: 89

Arg Ile Val Leu Thr Gln Ser Pro Ala Ile Thr Ala Ala Ser Leu Gly
1               5                   10                  15

Gln Lys Val Thr Ile Thr Cys Ser Ala Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Ser Tyr Pro Phe Thr Phe
                85                  90                  95

Gly Ser Gly Thr Lys Leu Glu Ile Lys
            100                 105

<210> SEQ ID NO 90
<211> LENGTH: 316
<212> TYPE: DNA
<213> ORGANISM: Artificial Sequence
<220> FEATURE:
<223> OTHER INFORMATION: Synthetic primer

<400> SEQUENCE: 90
agaattgtgc tcactcagtc tccagccatc acagctgcat ctctggggca aaaggtcacc      60
atcacctgca gtgccagctc aagtgtaagt tacatgcact ggtaccaaca gaagtcaggc     120
acctccccca aaccatggat ttatgaaata tccaaactgg cttctggagt cccagctcgc     180
ttcagtggca gtgggtctgg gacctcttac tctctcacaa tcagcagcat ggaggctgaa     240
gatgctgcca tttattactg ccagcagtgg agttatccat tcacgttcgg ctcggggaca     300
aagttggaaa taaaac                                           316

<210> SEQ ID NO 91
<211> LENGTH: 8
<212> TYPE: PRT
<213> ORGANISM: Artificial Sequence
<220> FEATURE:
<223> OTHER INFORMATION: Synthetic peptide

<400> SEQUENCE: 91

Gly Phe Thr Phe Ser Asp Tyr Tyr
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic peptide

<400> SEQUENCE: 92

Ile Ser Asp Gly Gly Thr Tyr Thr
1               5

<210> SEQ ID NO 93
<211> LENGTH: 15
<212> TYPE: PRT
<213> ORGANISM: Artificial Sequence
<220> FEATURE:
<223> OTHER INFORMATION: Synthetic peptide

<400> SEQUENCE: 93

Ala Arg Asp Arg Asp Asp Tyr Asp Glu Gly Pro Tyr Phe Asp Tyr
1               5                   10                  15

<210> SEQ ID NO 94
<211> LENGTH: 122
<212> TYPE: PRT
<213> ORGANISM: Artificial Sequence
<220> FEATURE:
<223> OTHER INFORMATION: Synthetic peptide

<400> SEQUENCE: 94

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Thr Ile Ser Asp Gly Gly Thr Tyr Thr Tyr Tyr Pro Asp Ser Val
        50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Asp Arg Asp Asp Tyr Asp Glu Gly Pro Tyr Phe Asp Tyr Trp
            100                 105                 110

Gly Gln Gly Thr Thr Leu Thr Val Ser Ser
            115                 120

<210> SEQ ID NO 95
<211> LENGTH: 367
<212> TYPE: DNA

<213> ORGANISM: Artificial Sequence
<220> FEATURE:
<223> OTHER INFORMATION: Synthetic primer

<400> SEQUENCE: 95

```
gaagtgcagc tggtggagtc tgggggaggc ttagtgaagc ctggagggtc cctgaaactc      60
tcctgtgcag cctctggatt cactttcagt gactattaca tgtattgggt tcgccagaca     120
ccggaaaaga ggctggagtg ggtcgcaacc attagtgatg gtggtactta cacctactat     180
ccagacagtg tgaaggggcg attcaccatc tccagagaca atgccaagaa caacctgtac     240
ctgcaaatga gcagtctgaa gtctgaggac acagccatgt tactgtgc aagagatcgg       300
gatgattacg acgaggggcc ctactttgac tactggggcc aaggcaccac tctcacagtc     360
tcctcag                                                                367
```

<210> SEQ ID NO 96
<211> LENGTH: 8
<212> TYPE: PRT
<213> ORGANISM: Artificial Sequence
<220> FEATURE:
<223> OTHER INFORMATION: Synthetic peptide

<400> SEQUENCE: 96

Arg Phe Thr Phe Ser Ser Tyr Val
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic peptide

<400> SEQUENCE: 97

Ile Gly Ser Gly Gly Thr Thr Tyr
1               5

<210> SEQ ID NO 98
<211> LENGTH: 13
<212> TYPE: PRT
<213> ORGANISM: Artificial Sequence
<220> FEATURE:
<223> OTHER INFORMATION: Synthetic peptide

<400> SEQUENCE: 98

Arg Gly Arg Gly Tyr Gly Phe Ala Trp Tyr Phe Asp Val
1               5                   10

<210> SEQ ID NO 99
<211> LENGTH: 119
<212> TYPE: PRT
<213> ORGANISM: Artificial Sequence
<220> FEATURE:
<223> OTHER INFORMATION: Synthetic peptide

<400> SEQUENCE: 99

Val Lys Leu Val Glu Ser Gly Gly Asp Leu Val Lys Pro Gly Gly Ser
1               5                   10                  15

Leu Lys Leu Ser Cys Ala Ala Ser Arg Phe Thr Phe Ser Ser Tyr Val
            20                  25                  30

Met Ser Trp Val Arg Gln Thr Pro Glu Lys Arg Leu Glu Trp Val Ala
        35                  40                  45

Ser Ile Gly Ser Gly Gly Thr Thr Tyr Tyr Pro Asp Thr Val Lys Gly

```
                50                  55                  60
Arg Phe Thr Ile Ser Arg Asp Asn Ala Arg Asn Ile Leu Tyr Leu Gln
 65                  70                  75                  80

Met Ser Ser Leu Arg Ser Asp Asp Thr Ala Met Tyr Tyr Cys Thr Arg
                 85                  90                  95

Gly Arg Gly Tyr Gly Phe Ala Trp Tyr Phe Asp Val Trp Gly Ala Gly
            100                 105                 110

Thr Thr Val Thr Val Ser Ser
            115

<210> SEQ ID NO 100
<211> LENGTH: 359
<212> TYPE: DNA
<213> ORGANISM: Artificial Sequence
<220> FEATURE:
<223> OTHER INFORMATION: Synthetic primer

<400> SEQUENCE: 100
agtgaagctg gtggagtctg ggggagactt agtgaagcct ggagggtccc tgaaactctc       60
ctgtgcagcc tctcgattca ctttcagtag ctatgtcatg tcttgggttc gccagactcc      120
agagaagagg ctggagtggg tcgcatccat tggtagtggt ggtaccacct actatccaga      180
caccgtgaag ggccgattca ccatctccag agataatgcc agaaacatcc tgtacctgca      240
aatgagcagt ctgaggtctg atgacacggc catgtattac tgtacaagag ccgaggtta       300 tggtttcgcc tggtacttcg atgtctgggg cgcagggacc acggtcaccg tctcctcag      359

<210> SEQ ID NO 101
<211> LENGTH: 5
<212> TYPE: PRT
<213> ORGANISM: Artificial Sequence
<220> FEATURE:
<223> OTHER INFORMATION: Synthetic peptide

<400> SEQUENCE: 101

Ser Ser Val Ser Tyr
1               5

<210> SEQ ID NO 102
<211> LENGTH: 3
<212> TYPE: PRT
<213> ORGANISM: Artificial Sequence
<220> FEATURE:
<223> OTHER INFORMATION: Synthetic peptide

<400> SEQUENCE: 102

Asp Thr Ser
1

<210> SEQ ID NO 103
<211> LENGTH: 9
<212> TYPE: PRT
<213> ORGANISM: Artificial Sequence
<220> FEATURE:
<223> OTHER INFORMATION: Synthetic peptide

<400> SEQUENCE: 103

Gln Gln Trp Ser Ser Tyr Pro Pro Thr
1               5

<210> SEQ ID NO 104
<211> LENGTH: 106
<212> TYPE: PRT
```

<213> ORGANISM: Artificial Sequence
<220> FEATURE:
<223> OTHER INFORMATION: Synthetic peptide

<400> SEQUENCE: 104

```
Thr Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gly Gly Thr Lys Leu Glu Ile Lys
            100                 105
```

<210> SEQ ID NO 105
<211> LENGTH: 319
<212> TYPE: DNA
<213> ORGANISM: Artificial Sequence
<220> FEATURE:
<223> OTHER INFORMATION: Synthetic primer

<400> SEQUENCE: 105

```
acaattgttc tcacccagtc tccagcaatc atgtctgcat ctccagggga gaaggtcacc      60
atgacctgca gtgccagctc aagtgtaagt tacatgtact ggtaccagca gaagccagga     120
tcctccccca gactcctgat ttatgacaca tccaacctgg cttctggagt ccctgttcgc     180
ttcagtggca gtgggtctgg gacctcttac tctctcacaa tcagccgaat ggaggctgaa     240
gatgctgcca cttattactg ccagcagtgg agtagttacc cacccacgtt cggagggggg     300
accaagctgg aaataaaac                                                   319
```

<210> SEQ ID NO 106
<211> LENGTH: 10
<212> TYPE: PRT
<213> ORGANISM: Artificial Sequence
<220> FEATURE:
<223> OTHER INFORMATION: Synthetic peptide

<400> SEQUENCE: 106

```
Glu Ser Val Glu Tyr Ser Gly Ala Ser Leu
1               5                   10
```

<210> SEQ ID NO 107
<211> LENGTH: 3
<212> TYPE: PRT
<213> ORGANISM: Artificial Sequence
<220> FEATURE:
<223> OTHER INFORMATION: Synthetic peptide

<400> SEQUENCE: 107

```
Ala Ala Ser
1
```

<210> SEQ ID NO 108
<211> LENGTH: 9
<212> TYPE: PRT

<213> ORGANISM: Artificial Sequence
<220> FEATURE:
<223> OTHER INFORMATION: Synthetic peptide

<400> SEQUENCE: 108

Gln Gln Ser Arg Lys Val Pro Ser Thr
1               5

<210> SEQ ID NO 109
<211> LENGTH: 109
<212> TYPE: PRT
<213> ORGANISM: Artificial Sequence
<220> FEATURE:
<223> OTHER INFORMATION: Synthetic peptide

<400> SEQUENCE: 109

Val Leu Thr Gln Ser Pro Ala Ser Leu Ala Val Ser Leu Gly Gln Arg
1               5                   10                  15

Ala Thr Ile Ser Cys Arg Ala Ser Glu Ser Val Glu Tyr Ser Gly Ala
            20                  25                  30

Ser Leu Met Gln Trp Tyr Gln His Lys Pro Gly Gln Pro Pro Lys Leu
        35                  40                  45

Leu Ile Tyr Ala Ala Ser Asn Val Glu Ser Gly Val Pro Ala Arg Phe
    50                  55                  60

Ser Gly Ser Gly Ser Gly Thr Asp Phe Ser Leu Asn Ile His Pro Val
65                  70                  75                  80

Glu Glu Asp Asp Ile Ala Met Tyr Phe Cys Gln Gln Ser Arg Lys Val
                85                  90                  95

Pro Ser Thr Phe Gly Gly Gly Thr Lys Leu Glu Ile Lys
            100                 105

<210> SEQ ID NO 110
<211> LENGTH: 329
<212> TYPE: DNA
<213> ORGANISM: Artificial Sequence
<220> FEATURE:
<223> OTHER INFORMATION: Synthetic primer

<400> SEQUENCE: 110
tgtgctcacc caatctccag cttctttggc tgtgtctctt gggcagagag ccaccatctc    60
ctgcagagcc agtgaaagtg ttgaatattc tggcgcaagt ttaatgcagt ggtaccaaca   120
caaaccagga cagccaccca aactcctcat ctatgctgca tccaacgtag aatctggggt   180
ccctgccagg tttagtggca gtgggtctgg gacagacttc agcctcaaca tccatcctgt   240
ggaggaggat gatattgcaa tgtatttctg tcagcaaagt aggaaggttc cttccacgtt   300
cggagggggg accaagctgg aaataaaac                                     329

<210> SEQ ID NO 111
<211> LENGTH: 8
<212> TYPE: PRT
<213> ORGANISM: Artificial Sequence
<220> FEATURE:
<223> OTHER INFORMATION: Synthetic peptide

<400> SEQUENCE: 111

Gly Ser Thr Phe Thr Asn His His
1               5

<210> SEQ ID NO 112
<211> LENGTH: 8
<212> TYPE: PRT

```
<213> ORGANISM: Artificial Sequence
<220> FEATURE:
<223> OTHER INFORMATION: Synthetic peptide

<400> SEQUENCE: 112

Leu Asn Pro Tyr Asn Asp Tyr Thr
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic peptide

<400> SEQUENCE: 113

Ala Thr Ile Thr Phe Asp Ser
1               5

<210> SEQ ID NO 114
<211> LENGTH: 106
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (105)..(105)
<223> OTHER INFORMATION: Xaa can be any naturally occurring amino acid

<400> SEQUENCE: 114

Gln Val Gln Leu Gln Gln Ser Gly Ala Glu Leu Val Arg Pro Gly Ala
1               5                   10                  15

Ser Val Lys Ile Ser Cys Lys Ala Phe Gly Ser Thr Phe Thr Asn His
                20                  25                  30

His Ile Asn Trp Val Lys Gln Arg Pro Gly Gln Gly Leu Asp Trp Ile
            35                  40                  45

Gly Tyr Leu Asn Pro Tyr Asn Asp Tyr Thr Asn Tyr Asn Gln Lys Phe
        50                  55                  60

Lys Gly Lys Ala Thr Leu Thr Ile Asp Lys Ser Ser Ser Thr Ala Tyr
65                  70                  75                  80

Leu Glu Leu Ser Ser Leu Thr Ser Glu Asp Ser Ala Val Tyr Tyr Cys
                85                  90                  95

Ala Thr Ile Thr Phe Asp Ser Gln Xaa Gln
            100                 105

<210> SEQ ID NO 115
<211> LENGTH: 320
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (314)..(315)
<223> OTHER INFORMATION: n is a, c, g, or t

<400> SEQUENCE: 115
caggtccagc tgcagcagtc tggggctgag ctggtgaggc ctggggcctc agtgaagatt      60
tcctgcaagg cttttggctc caccttcaca aaccatcata taaattgggt gaagcagagg     120
cctggacagg gcctggactg gattggatat cttaatcctt ataatgatta tactaactac     180
aaccagaagt tcaagggcaa ggccacattg actatagaca atcctccag cacagcctat     240
```

```
ctggagctta gcagcctgac atctgaggac tctgcagtgt attactgtgc aaccataact      300
tttgacagcc aggnncaagg                                                  320
```

<210> SEQ ID NO 116
<211> LENGTH: 8
<212> TYPE: PRT
<213> ORGANISM: Artificial Sequence
<220> FEATURE:
<223> OTHER INFORMATION: Synthetic peptide

<400> SEQUENCE: 116

Gly Phe Thr Phe Ser Asn Tyr Asp
1               5

<210> SEQ ID NO 117
<211> LENGTH: 8
<212> TYPE: PRT
<213> ORGANISM: Artificial Sequence
<220> FEATURE:
<223> OTHER INFORMATION: Synthetic peptide

<400> SEQUENCE: 117

Ile Ser Ser Gly Gly Thr Tyr Pro
1               5

<210> SEQ ID NO 118
<211> LENGTH: 17
<212> TYPE: PRT
<213> ORGANISM: Artificial Sequence
<220> FEATURE:
<223> OTHER INFORMATION: Synthetic peptide

<400> SEQUENCE: 118

Ala Arg Gly Gly Phe Leu Ile Thr Thr Arg Asp Tyr Tyr Ala Met Asp
1               5                   10                  15

Tyr

<210> SEQ ID NO 119
<211> LENGTH: 124
<212> TYPE: PRT
<213> ORGANISM: Artificial Sequence
<220> FEATURE:
<223> OTHER INFORMATION: Synthetic peptide

<400> SEQUENCE: 119

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
                20                  25                  30

Asp Met Ser Trp Val Arg Gln Thr Pro Glu Lys Arg Leu Glu Arg Val
            35                  40                  45

Ala Thr Ile Ser Ser Gly Gly Thr Tyr Pro Tyr Tyr Pro Asp Ser Val
        50                  55                  60

Lys Gly Arg Phe Thr Ile Ser Arg Asp Asn Ala Glu Asn Thr Leu Tyr
65                  70                  75                  80

Leu Gln Leu Ser Ser Leu Arg Ser Glu Asp Thr Ala Leu Tyr Tyr Cys
                85                  90                  95

Ala Arg Gly Gly Phe Leu Ile Thr Thr Arg Asp Tyr Tyr Ala Met Asp
            100                 105                 110

Tyr Trp Gly Gln Gly Thr Ser Val Thr Val Ser Ser
        115                 120

<210> SEQ ID NO 120
<211> LENGTH: 372
<212> TYPE: DNA
<213> ORGANISM: Artificial Sequence
<220> FEATURE:
<223> OTHER INFORMATION: Synthetic primer

<400> SEQUENCE: 120

```
gaagtgaaac tggtggagtc tgggggaggc ttagtgaagc ctggagggtc cctgaaactc      60
tcctgtgcag cctctggatt cactttcagt aactatgaca tgtcttgggt tcgccagact     120
ccggagaaga ggctggagcg ggtcgcaacc attagtagtg gtggtactta cccctactat     180
ccagacagtg tgaagggccg tttcaccatc tccagagaca atgccgagaa caccctgtac     240
ctgcaattga gcagtctgag gtctgaggac acggccctgt attactgtgc aagagggggga    300 tttttgatta cgacacggga ctactatgct atggactact ggggtcaagg aacctcagtc     360
accgtctcct ca                                                         372
```

<210> SEQ ID NO 121
<211> LENGTH: 10
<212> TYPE: PRT
<213> ORGANISM: Artificial Sequence
<220> FEATURE:
<223> OTHER INFORMATION: Synthetic peptide

<400> SEQUENCE: 121

Glu Ser Val Asp Tyr Ser Gly Ala Ser Leu
1               5                   10

<210> SEQ ID NO 122
<211> LENGTH: 3
<212> TYPE: PRT
<213> ORGANISM: Artificial Sequence
<220> FEATURE:
<223> OTHER INFORMATION: Synthetic peptide

<400> SEQUENCE: 122

Ala Ala Ser
1

<210> SEQ ID NO 123
<211> LENGTH: 9
<212> TYPE: PRT
<213> ORGANISM: Artificial Sequence
<220> FEATURE:
<223> OTHER INFORMATION: Synthetic peptide

<400> SEQUENCE: 123

Gln Gln Ser Arg Lys Val Pro Ser Thr
1               5

<210> SEQ ID NO 124
<211> LENGTH: 111
<212> TYPE: PRT
<213> ORGANISM: Artificial Sequence
<220> FEATURE:
<223> OTHER INFORMATION: Synthetic peptide

<400> SEQUENCE: 124

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Tyr Ser
            20                  25                  30

Gly Ala Ser Leu Met Gln Trp Tyr Gln His Lys Pro Gly Gln Pro Pro
            35                  40                  45

Arg Leu Leu Ile Tyr Ala Ala Ser Asn Val Glu Ser Gly Val Pro Ala
 50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Arg
                 85                  90                  95

Lys Val Pro Ser Thr Phe Gly Gly Gly Thr Lys Leu Glu Ile Lys
            100                 105                 110

<210> SEQ ID NO 125
<211> LENGTH: 334
<212> TYPE: DNA
<213> ORGANISM: Artificial Sequence
<220> FEATURE:
<223> OTHER INFORMATION: Synthetic primer

<400> SEQUENCE: 125
gacattgtgc tcacccaatc tccagcttct ttggctgtgt ctcttgggca gagagccacc      60
atctcctgca gagccagtga aagtgttgat tattctggcg caagtttaat gcagtggtac     120
caacacaaac caggacagcc acccagactc ctcatctatg ctgcatccaa cgtagaatct     180
ggggtccctg ccaggtttag tggcagtggg tctgggacag acttcagcct caacatccat     240
cctgtggagg aggatgatat tgcaatgtat ttctgtcagc aaagtaggaa ggttccttcc     300
acgttcggag gggggaccaa gctggaaata aaac                                 334

<210> SEQ ID NO 126
<211> LENGTH: 10
<212> TYPE: PRT
<213> ORGANISM: Artificial Sequence
<220> FEATURE:
<223> OTHER INFORMATION: Synthetic peptide

<400> SEQUENCE: 126

Glu Ser Val Glu Tyr Ser Gly Ala Ser Leu
 1               5                  10

<210> SEQ ID NO 127
<211> LENGTH: 3
<212> TYPE: PRT
<213> ORGANISM: Artificial Sequence
<220> FEATURE:
<223> OTHER INFORMATION: Synthetic peptide

<400> SEQUENCE: 127

Ala Ala Ser
 1

<210> SEQ ID NO 128
<211> LENGTH: 9
<212> TYPE: PRT
<213> ORGANISM: Artificial Sequence
<220> FEATURE:
<223> OTHER INFORMATION: Synthetic peptide

<400> SEQUENCE: 128

Gln Gln Ser Arg Lys Val Pro Ser Thr
 1               5

<210> SEQ ID NO 129
<211> LENGTH: 102

```
<212> TYPE: PRT
<213> ORGANISM: Artificial Sequence
<220> FEATURE:
<223> OTHER INFORMATION: Synthetic peptide

<400> SEQUENCE: 129

Phe Phe Gly Val Ser Leu Gly Gln Arg Ala Ser Ile Ser Cys Arg Ala
1               5                   10                  15

Ser Glu Ser Val Glu Tyr Ser Gly Ala Ser Leu Ile Gln Trp Tyr Gln
            20                  25                  30

His Lys Pro Gly Gln Pro Pro Lys Leu Leu Ile Tyr Ala Ala Ser Asn
        35                  40                  45

Val Glu Ser Gly Val Pro Val Arg Phe Ser Gly Ser Gly Ser Gly Thr
    50                  55                  60

Asp Phe Ser Leu Asn Ile His Pro Val Glu Glu Asp Asp Ile Ala Met
65                  70                  75                  80

Tyr Phe Cys Gln Gln Ser Arg Lys Val Pro Ser Thr Phe Gly Gly Gly
                85                  90                  95

Thr Lys Leu Glu Ile Lys
            100

<210> SEQ ID NO 130
<211> LENGTH: 255
<212> TYPE: DNA
<213> ORGANISM: Artificial Sequence
<220> FEATURE:
<223> OTHER INFORMATION: Synthetic primer

<400> SEQUENCE: 130
cttctttggt gtgtctcttg ggcagagagc cagcatctcc tgcagagcca gtgaaagtgt      60
tgaatattca ggcgcaagtt taatacagtg gtaccaacac aaaccaggac agccacccaa     120
actcctcatc tatgctgcat ccaacgtaga atctggggtc cctgtcaggt ttagtggcag     180
tgggtctggg acagacttca gcctcaacat ccatcctgtg gaggaggatg atattgcaat     240
gtatttctgt cagca                                                     255

<210> SEQ ID NO 131
<211> LENGTH: 8
<212> TYPE: PRT
<213> ORGANISM: Artificial Sequence
<220> FEATURE:
<223> OTHER INFORMATION: Synthetic peptide

<400> SEQUENCE: 131

Gly Phe Thr Phe Ser Asn Tyr Asp
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic peptide

<400> SEQUENCE: 132

Ile Ser Ser Gly Gly Thr Tyr Pro
1               5

<210> SEQ ID NO 133
<211> LENGTH: 17
<212> TYPE: PRT
<213> ORGANISM: Artificial Sequence
```

<220> FEATURE:
<223> OTHER INFORMATION: Synthetic peptide

<400> SEQUENCE: 133

Ala Arg Gly Gly Phe Leu Ile Thr Thr Arg Asp Tyr Tyr Ala Met Asp
1               5                   10                  15

Tyr

<210> SEQ ID NO 134
<211> LENGTH: 124
<212> TYPE: PRT
<213> ORGANISM: Artificial Sequence
<220> FEATURE:
<223> OTHER INFORMATION: Synthetic peptide

<400> SEQUENCE: 134

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
            20                  25                  30

Asp Met Ser Trp Val Arg Gln Thr Pro Glu Lys Arg Leu Glu Trp Val
        35                  40                  45

Ala Thr Ile Ser Ser Gly Gly Thr Tyr Pro Tyr Tyr Pro Asp Ser Val
    50                  55                  60

Lys Gly Arg Phe Thr Ile Ser Arg Asp Asn Ala Glu Asn Thr Leu Tyr
65                  70                  75                  80

Leu Gln Leu Ser Ser Leu Arg Ser Glu Asp Thr Ala Leu Tyr Tyr Cys
                85                  90                  95

Ala Arg Gly Gly Phe Leu Ile Thr Thr Arg Asp Tyr Tyr Ala Met Asp
            100                 105                 110

Tyr Trp Gly Gln Gly Thr Ser Val Thr Val Ser Ser
        115                 120

<210> SEQ ID NO 135
<211> LENGTH: 373
<212> TYPE: DNA
<213> ORGANISM: Artificial Sequence
<220> FEATURE:
<223> OTHER INFORMATION: Synthetic primer

<400> SEQUENCE: 135
gaagtgaaac tggtggagtc tgggggaggc ttagtgaagc ctggagggtc cctgaaactc      60
tcctgtgcag cctctggatt cactttcagt aactatgaca tgtcttgggt tcgccagact     120
ccggagaaga ggctggagtg ggtcgcaacc attagtagtg gtggtactta ccctactat     180 ccagacagtg tgaagggccg tttcaccatc tccagagaca atgccgagaa caccctgtac     240
ctgcaattga gcagtctgag gtctgaggac acggccctgt attactgtgc aagaggggga     300 ttttgatta cgacacggga ctactatgct atggactact ggggtcaagg aacctcagtc     360
accgtctcct cag                                                        373

<210> SEQ ID NO 136
<211> LENGTH: 10
<212> TYPE: PRT
<213> ORGANISM: Artificial Sequence
<220> FEATURE:
<223> OTHER INFORMATION: Synthetic peptide

<400> SEQUENCE: 136

Glu Ser Val Glu Tyr Tyr Gly Ala Ser Leu

<210> SEQ ID NO 137
<211> LENGTH: 3
<212> TYPE: PRT
<213> ORGANISM: Artificial Sequence
<220> FEATURE:
<223> OTHER INFORMATION: Synthetic peptide

<400> SEQUENCE: 137

Ala Ala Ser
1

<210> SEQ ID NO 138
<211> LENGTH: 9
<212> TYPE: PRT
<213> ORGANISM: Artificial Sequence
<220> FEATURE:
<223> OTHER INFORMATION: Synthetic peptide

<400> SEQUENCE: 138

Gln Gln Ser Arg Lys Val Pro Asn Thr
1               5

<210> SEQ ID NO 139
<211> LENGTH: 111
<212> TYPE: PRT
<213> ORGANISM: Artificial Sequence
<220> FEATURE:
<223> OTHER INFORMATION: Synthetic peptide

<400> SEQUENCE: 139

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Tyr Tyr
            20                  25                  30

Gly Ala Ser Leu Met Gln Trp Tyr Gln Gln Lys Ser Gly Gln Pro Pro
        35                  40                  45

Lys Leu Leu Ile Tyr Ala Ala Ser Asn Val Glu Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Asn Thr Phe Gly Gly Gly Thr Lys Leu Glu Ile Lys
            100                 105                 110

<210> SEQ ID NO 140
<211> LENGTH: 334
<212> TYPE: DNA
<213> ORGANISM: Artificial Sequence
<220> FEATURE:
<223> OTHER INFORMATION: Synthetic primer

<400> SEQUENCE: 140
gacattgtgc tcacccaatc tccagcttct ttggctgtgt ctctagggca gagagccacc      60
atctcctgca gagccagtga agtgttgaa tattatggcg caagtttaat gcagtggtac      120
caacagaaat caggacagcc acccaaactc ctcatctatg ctgcatccaa cgtagaatct     180
ggggtccctg ccaggtttag tggcagtggg tctgggacag acttcagcct caacatccac     240
cctgtggagg aggatgatat tgcaatgtat ttctgtcagc aaagtaggaa ggttccgaac     300
acgttcggag gggggaccaa gctggaaata aaac                                    334

<210> SEQ ID NO 141
<211> LENGTH: 5
<212> TYPE: PRT
<213> ORGANISM: Artificial Sequence
<220> FEATURE:
<223> OTHER INFORMATION: Synthetic peptide

<400> SEQUENCE: 141

Ser Ser Val Ser Tyr
1               5

<210> SEQ ID NO 142
<211> LENGTH: 3
<212> TYPE: PRT
<213> ORGANISM: Artificial Sequence
<220> FEATURE:
<223> OTHER INFORMATION: Synthetic peptide

<400> SEQUENCE: 142

Glu Thr Ser
1

<210> SEQ ID NO 143
<211> LENGTH: 8
<212> TYPE: PRT
<213> ORGANISM: Artificial Sequence
<220> FEATURE:
<223> OTHER INFORMATION: Synthetic peptide

<400> SEQUENCE: 143

Gln Gln Trp Ser Tyr Pro Phe Thr
1               5

<210> SEQ ID NO 144
<211> LENGTH: 105
<212> TYPE: PRT
<213> ORGANISM: Artificial Sequence
<220> FEATURE:
<223> OTHER INFORMATION: Synthetic peptide

<400> SEQUENCE: 144

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Val Ser Tyr Met
            20                  25                  30

His Trp Tyr His Gln Lys Ser Gly Thr Ser Pro Lys Pro Trp Ile Tyr
        35                  40                  45

Glu Thr Ser Lys Leu Ala Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Gln Trp Ser Tyr Pro Phe Thr Phe
                85                  90                  95

Gly Ser Gly Thr Lys Leu Glu Ile Lys
            100                 105

<210> SEQ ID NO 145
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 145

His Cys Ala His Pro Ser Pro Ala Ser Leu Ala Val Ser Leu Gly Gln
1               5                   10                  15

Arg Ala Ser Ile Ser Cys Arg Ala Ser Glu Ser Val Glu Tyr Ser Gly
            20                  25                  30

Ala Ser Leu Met Gln Trp Tyr Gln His Lys Pro Gly Gln Pro Pro Lys
        35                  40                  45

Leu Leu Ile Tyr Ala Ala Ser Asn Val Glu Ser Gly Val Pro Val Arg
50                  55                  60

Phe Ser Gly Ser Gly Ser Gly Thr Asp Phe Ser Leu Asn Ile His Pro
65                  70                  75                  80

Val Glu Glu Asp Asp Ile Ala Met Tyr Phe Cys Gln Gln Ser Arg Lys
                85                  90                  95

Val Pro Ser Thr Phe Gly Gly Gly Thr Lys Leu Glu Ile Lys
            100                 105                 110

<210> SEQ ID NO 146
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 146

Cys Ser Pro Ser Pro Ala Ser Leu Ala Val Ser Leu Gly Gln Arg Ala
1               5                   10                  15

Thr Ile Ser Cys Arg Ala Ser Glu Ser Val Glu Tyr Ser Gly Ala Ser
            20                  25                  30

Leu Met Gln Trp Tyr Gln His Lys Pro Gly Gln Pro Pro Lys Leu Leu
        35                  40                  45

Ile Tyr Ala Ala Ser Asn Val Glu Ser Gly Val Pro Ala Arg Phe Ser
50                  55                  60

Gly Ser Gly Ser Gly Thr Asp Phe Ser Leu Asn Ile His Pro Val Glu
65                  70                  75                  80

Glu Asp Asp Ile Ala Met Tyr Phe Cys Gln Gln Ser Arg Lys Val Pro
                85                  90                  95

Ser Thr Phe Gly Gly Gly Thr Lys Leu Glu Ile Lys
            100                 105

<210> SEQ ID NO 147
<211> LENGTH: 108
<212> TYPE: PRT
<213> ORGANISM: Artificial Sequence
<220> FEATURE:
<223> OTHER INFORMATION: Synthetic Peptide

<400> SEQUENCE: 147

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Thr Asp Gly Val Pro Ser Arg Phe Ser Gly
50                  55                  60

Ser Gly Ser Gly Thr Gln Phe Ser Leu Lys Ile Asn Ser Leu Gln Ala
65                  70                  75                  80

Gly Asp Phe Gly Ser Tyr Tyr Cys Gln His Ser Trp Ser Ile Pro Tyr
                85                  90                  95

Thr Phe Gly Gly Gly Thr Arg Leu Gln Ile Arg Arg
            100                 105

<210> SEQ ID NO 148
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 148

Ala Gln His Asp Glu Ala Lys Lys Asn Ala Phe Tyr Gln Val Leu Asn
1               5                   10                  15

Met Pro Asn Leu Asn Ala
            20

<210> SEQ ID NO 149
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 149

Asn Met Pro Asn Leu Asn Ala Asp Gln Arg Asn Gly Phe Ile Gln Ser
1               5                   10                  15

Leu Lys Ala Ala Pro Ser Gln
            20

<210> SEQ ID NO 150
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 150

Ala Ala Pro Ser Gln Ser Ala Asn Val Leu Gly Glu Ala Gln Lys Leu
1               5                   10                  15

Asn Asp Ser Gln Ala Pro Lys
            20

<210> SEQ ID NO 151
<211> LENGTH: 38
<212> TYPE: PRT
<213> ORGANISM: Artificial Sequence
<220> FEATURE:
<223> OTHER INFORMATION: Synthetic Peptide

<400> SEQUENCE: 151

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln
        35

<210> SEQ ID NO 152
<211> LENGTH: 41
<212> TYPE: PRT
<213> ORGANISM: Artificial Sequence -continued

```
<220> FEATURE:
<223> OTHER INFORMATION: Synthetic Peptide

<400> SEQUENCE: 152

Asn Met Pro Asn Leu Asn Ala Asp Gln Arg Asn Gly Phe Ile Gln Ser
1               5                   10                  15

Leu Lys Ala Ala Pro Ser Gln Ser Ala Asn Val Leu Gly Glu Ala Gln
            20                  25                  30

Lys Leu Asn Asp Ser Gln Ala Pro Lys
        35                  40

<210> SEQ ID NO 153
<211> LENGTH: 56
<212> TYPE: PRT
<213> ORGANISM: Artificial Sequence
<220> FEATURE:
<223> OTHER INFORMATION: Synthetic Peptide

<400> SEQUENCE: 153

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 154
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 154

Ser Ser Val Ser Tyr
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 155

Gln Gln Trp Ser Ser Tyr Pro Pro Thr
1               5

<210> SEQ ID NO 156
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 156

Glu Ser Val Glu Tyr Ser Gly Ala Ser Leu
1               5                   10

<210> SEQ ID NO 157
<211> LENGTH: 9
<212> TYPE: PRT
```

<213> ORGANISM: Artificial Sequence
<220> FEATURE:
<223> OTHER INFORMATION: Synthetic Peptide

<400> SEQUENCE: 157

Gln Gln Ser Arg Lys Val Pro Ser Thr
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 158

Gln Gln Trp Ser Tyr Pro Phe Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 159

Phe Tyr Pro Gly Ser Gly Tyr Ile Ala
1               5

<210> SEQ ID NO 160
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: X is Glu or Asp

<400> SEQUENCE: 160

Glu Ser Val Xaa Tyr Ser Gly Ala Ser Leu
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is Glu or absent
<220> FEATURE:
<221> NAME/KEY: MISC_FEATURE
<222> LOCATION: (2)..(2)
<223> OTHER INFORMATION: X is Ser or absent
<220> FEATURE:
<221> NAME/KEY: MISC_FEATURE
<222> LOCATION: (3)..(3)
<223> OTHER INFORMATION: X is Val or absent
<220> FEATURE:
<221> NAME/KEY: MISC_FEATURE
<222> LOCATION: (4)..(4)
<223> OTHER INFORMATION: X is Glu or absent
<220> FEATURE:
<221> NAME/KEY: MISC_FEATURE
<222> LOCATION: (5)..(5)
<223> OTHER INFORMATION: X is Tyr or absent

```
<220> FEATURE:
<221> NAME/KEY: MISC_FEATURE
<222> LOCATION: (7)..(7)
<223> OTHER INFORMATION: X is Gly or Ser
<220> FEATURE:
<221> NAME/KEY: MISC_FEATURE
<222> LOCATION: (8)..(8)
<223> OTHER INFORMATION: X is Ala or Val
<220> FEATURE:
<221> NAME/KEY: MISC_FEATURE
<222> LOCATION: (10)..(10)
<223> OTHER INFORMATION: X is Leu or Tyr

<400> SEQUENCE: 161

Xaa Xaa Xaa Xaa Xaa Ser Xaa Xaa Ser Xaa
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is Glu or Ser
<220> FEATURE:
<221> NAME/KEY: MISC_FEATURE
<222> LOCATION: (4)..(4)
<223> OTHER INFORMATION: X is Glu, Asp, or Ser
<220> FEATURE:
<221> NAME/KEY: MISC_FEATURE
<222> LOCATION: (6)..(6)
<223> OTHER INFORMATION: X is Ser or Tyr

<400> SEQUENCE: 162

Xaa Ser Val Xaa Tyr Xaa Gly Ala Ser Leu
1               5                   10

<210> SEQ ID NO 163
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (8)..(8)
<223> OTHER INFORMATION: X is Ser or Asn

<400> SEQUENCE: 163

Gln Gln Ser Arg Lys Val Pro Xaa Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: X is Ser or Trp
<220> FEATURE:
<221> NAME/KEY: MISC_FEATURE
<222> LOCATION: (4)..(4)
<223> OTHER INFORMATION: X is Arg or Ser
<220> FEATURE:
<221> NAME/KEY: MISC_FEATURE
<222> LOCATION: (5)..(5)
<223> OTHER INFORMATION: X is Lys or Tyr
```

```
<220> FEATURE:
<221> NAME/KEY: MISC_FEATURE
<222> LOCATION: (6)..(6)
<223> OTHER INFORMATION: X is Val or Pro
<220> FEATURE:
<221> NAME/KEY: MISC_FEATURE
<222> LOCATION: (7)..(7)
<223> OTHER INFORMATION: X is Pro or absent
<220> FEATURE:
<221> NAME/KEY: MISC_FEATURE
<222> LOCATION: (8)..(8)
<223> OTHER INFORMATION: X is Ser or Phe

<400> SEQUENCE: 164

Gln Gln Xaa Xaa Xaa Xaa Xaa Xaa Thr
1               5

<210> SEQ ID NO 165
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is Gln or Ser
<220> FEATURE:
<221> NAME/KEY: MISC_FEATURE
<222> LOCATION: (3)..(3)
<223> OTHER INFORMATION: X is Ser, Trp or Iso
<220> FEATURE:
<221> NAME/KEY: MISC_FEATURE
<222> LOCATION: (4)..(4)
<223> OTHER INFORMATION: X is Arg, Ser or Thr
<220> FEATURE:
<221> NAME/KEY: MISC_FEATURE
<222> LOCATION: (5)..(5)
<223> OTHER INFORMATION: X is Lys, Tyr, or Ser
<220> FEATURE:
<221> NAME/KEY: MISC_FEATURE
<222> LOCATION: (6)..(6)
<223> OTHER INFORMATION: X is Val or Tyr
<220> FEATURE:
<221> NAME/KEY: MISC_FEATURE
<222> LOCATION: (8)..(8)
<223> OTHER INFORMATION: X is Ser, Pro or Trp

<400> SEQUENCE: 165

Xaa Gln Xaa Xaa Xaa Xaa Pro Xaa Thr
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is Gln or Ser
<220> FEATURE:
<221> NAME/KEY: MISC_FEATURE
<222> LOCATION: (3)..(3)
<223> OTHER INFORMATION: X is Ser, Trp or Iso
<220> FEATURE:
<221> NAME/KEY: MISC_FEATURE
<222> LOCATION: (4)..(4)
<223> OTHER INFORMATION: X is Arg, Ser or Thr
<220> FEATURE:
<221> NAME/KEY: MISC_FEATURE
<222> LOCATION: (5)..(5)
<223> OTHER INFORMATION: X is Lys, Ser or Tyr
<220> FEATURE:
```

```
<221> NAME/KEY: MISC_FEATURE
<222> LOCATION: (6)..(6)
<223> OTHER INFORMATION: X is Val or Tyr
<220> FEATURE:
<221> NAME/KEY: MISC_FEATURE
<222> LOCATION: (8)..(8)
<223> OTHER INFORMATION: X is Ser, Pro, Trp, Phe, or Asn

<400> SEQUENCE: 166

Xaa Gln Xaa Xaa Xaa Xaa Pro Xaa Thr
1               5

<210> SEQ ID NO 167
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (5)..(5)
<223> OTHER INFORMATION: X is Asn or Ser
<220> FEATURE:
<221> NAME/KEY: MISC_FEATURE
<222> LOCATION: (6)..(6)
<223> OTHER INFORMATION: X is Thr, Asn, or Asp
<220> FEATURE:
<221> NAME/KEY: MISC_FEATURE
<222> LOCATION: (7)..(7)
<223> OTHER INFORMATION: X is Asn or Tyr
<220> FEATURE:
<221> NAME/KEY: MISC_FEATURE
<222> LOCATION: (8)..(8)
<223> OTHER INFORMATION: X is Ala, Asp or Tyr

<400> SEQUENCE: 167

Gly Phe Thr Phe Xaa Xaa Xaa Xaa
1               5

<210> SEQ ID NO 168
<211> LENGTH: 19
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: X is Ala or Gly
<220> FEATURE:
<221> NAME/KEY: MISC_FEATURE
<222> LOCATION: (4)..(4)
<223> OTHER INFORMATION: X is Arg or Tyr
<220> FEATURE:
<221> NAME/KEY: MISC_FEATURE
<222> LOCATION: (6)..(6)
<223> OTHER INFORMATION: X is Val, Gly, Asn, or Ala
<220> FEATURE:
<221> NAME/KEY: MISC_FEATURE
<222> LOCATION: (7)..(7)
<223> OTHER INFORMATION: X is Thr, Phe, or Arg
<220> FEATURE:
<221> NAME/KEY: MISC_FEATURE
<222> LOCATION: (8)..(8)
<223> OTHER INFORMATION: X is Glu, Leu, Ala, or Tyr
<220> FEATURE:
<221> NAME/KEY: MISC_FEATURE
<222> LOCATION: (9)..(9)
<223> OTHER INFORMATION: X is His, Iso or Gly
<220> FEATURE:
<221> NAME/KEY: MISC_FEATURE
<222> LOCATION: (10)..(10)
<223> OTHER INFORMATION: X is Tyr, Thr, or Phe
<220> FEATURE:
<221> NAME/KEY: MISC_FEATURE
```

```
<222> LOCATION: (11)..(11)
<223> OTHER INFORMATION: X is Asp or Thr
<220> FEATURE:
<221> NAME/KEY: MISC_FEATURE
<222> LOCATION: (12)..(12)
<223> OTHER INFORMATION: X is Tyr, Arg, Cys, or Gly
<220> FEATURE:
<221> NAME/KEY: MISC_FEATURE
<222> LOCATION: (13)..(13)
<223> OTHER INFORMATION: X is Asp, Val or Thr
<220> FEATURE:
<221> NAME/KEY: MISC_FEATURE
<222> LOCATION: (14)..(14)
<223> OTHER INFORMATION: X is Tyr, Gly or Phe
<220> FEATURE:
<221> NAME/KEY: MISC_FEATURE
<222> LOCATION: (16)..(16)
<223> OTHER INFORMATION: X is Val or Ala

<400> SEQUENCE: 168

Arg His Xaa Xaa Gly Xaa Xaa Xaa Xaa Xaa Xaa Xaa Xaa Tyr Xaa
1               5                   10                  15

Met Asp Tyr

<210> SEQ ID NO 169
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 169

His Asp Glu Ala Gln Gln Asn Ala Phe Tyr Gln Val Leu Asn Met Pro
1               5                   10                  15

Asn Leu Asn Ala Asp Gln Arg Asn Gly Phe Ile Gln Ser Leu Lys Asp
                20                  25                  30

Asp Pro Ser Gln Ser Ala Asn Val Leu Gly Glu Ala Gln Lys Leu Asn
        35                  40                  45

Asp Ser Gln Ala Pro Lys
        50

<210> SEQ ID NO 170
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 170

Phe Asn Lys Asp Gln Gln Ser Ala Phe Tyr Glu Ile Leu Asn Met Pro
1               5                   10                  15

Asn Leu Asn Glu Ala Gln Arg Asn Gly Phe Ile Gln Ser Leu Lys Asp
                20                  25                  30

Asp Pro Ser Gln Ser Thr Asn Val Leu Gly Glu Ala Lys Lys Leu Asn
        35                  40                  45

Glu Ser Gln Ala Pro Lys
        50

<210> SEQ ID NO 171
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 171
```

Phe Asn Lys Glu Gln Gln Asn Ala Phe Tyr Glu Ile Leu Asn Met Pro
1               5                   10                  15

Asn Leu Asn Glu Glu Gln Arg Asn Gly Phe Ile Gln Ser Leu Lys Asp
            20                  25                  30

Asp Pro Ser Gln Ser Ala Asn Leu Leu Ser Glu Ala Lys Lys Leu Asn
        35                  40                  45

Glu Ser Gln Ala Pro Lys
    50

<210> SEQ ID NO 172
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 172

Phe Asn Lys Glu Gln Gln Asn Ala Phe Tyr Glu Ile Leu His Leu Pro
1               5                   10                  15

Asn Leu Asn Glu Glu Gln Arg Asn Gly Phe Ile Gln Ser Leu Lys Asp
            20                  25                  30

Asp Pro Ser Gln Ser Ala Asn Leu Leu Ala Glu Ala Lys Lys Leu Asn
        35                  40                  45

Asp Ala Gln Ala Pro Lys
    50

<210> SEQ ID NO 173
<211> LENGTH: 54
<212> TYPE: PRT
<213> ORGANISM: Artificial Sequence
<220> FEATURE:
<223> OTHER INFORMATION: Synthetic Peptide

<400> SEQUENCE: 173

Phe Asn Lys Glu Gln Gln Asn Ala Phe Tyr Glu Ile Leu His Leu Pro
1               5                   10                  15

Asn Leu Thr Glu Glu Gln Arg Asn Gly Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50

<210> SEQ ID NO 174
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 174

Lys Lys Ala Ala
1

<210> SEQ ID NO 175
<211> LENGTH: 4
<212> TYPE: PRT
<213> ORGANISM: Artificial Sequence -continued

```
<220> FEATURE:
<223> OTHER INFORMATION: Synthetic Peptide

<400> SEQUENCE: 175

Gly Gly Ser Ser
1
```

UNITED STATES PATENT AND TRADEMARK OFFICE
CERTIFICATE OF CORRECTION

| | | |
|---|---|---|
| PATENT NO. | : 10,047,149 B2 | Page 1 of 1 |
| APPLICATION NO. | : 15/377050 | |
| DATED | : August 14, 2018 | |
| INVENTOR(S) | : Schneewind et al. | |

It is certified that error appears in the above-identified patent and that said Letters Patent is hereby corrected as shown below:

In the Specification

On Column 1, at Line 15, the paragraph should read as follows:
-- This invention was made with government support under grant numbers AI092711, AI057153, AI052474 awarded by the National Institutes of Health. The government has certain rights in the invention. --

Signed and Sealed this
Twelfth Day of September, 2023

Katherine Kelly Vidal
*Director of the United States Patent and Trademark Office*